(12) United States Patent
Cho et al.

(10) Patent No.: US 8,637,558 B2
(45) Date of Patent: Jan. 28, 2014

(54) THIAZOLIDINEDIONE DERIVATIVE AND USE THEREOF

(75) Inventors: Hoon Cho, Gwangju (KR); Ying Wu, Gwangju (KR); Cheol-Hee Choi, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 150 days.

(21) Appl. No.: 13/142,924

(22) PCT Filed: Dec. 30, 2009

(86) PCT No.: PCT/KR2009/007995
§ 371 (c)(1),
(2), (4) Date: Jun. 30, 2011

(87) PCT Pub. No.: WO2010/077101
PCT Pub. Date: Jul. 8, 2010

(65) Prior Publication Data
US 2011/0269954 A1    Nov. 3, 2011

(30) Foreign Application Priority Data

Dec. 30, 2008  (KR) .................. 10-2008-0136921
Jun. 22, 2009  (KR) .................. 10-2009-0055326

(51) Int. Cl.
*A61K 31/426*    (2006.01)
*C07D 277/34*    (2006.01)

(52) U.S. Cl.
USPC .......................................... 514/369; 548/182

(58) Field of Classification Search
USPC .......................................... 548/182; 514/369
See application file for complete search history.

(56) References Cited

PUBLICATIONS

Pizzuti, G. Gazzetta Chimica Italiana (1911), 40(II), 236-41.*

* cited by examiner

*Primary Examiner* — Kahsay Habte
(74) *Attorney, Agent, or Firm* — Joseph Hyosuk Kim; JHK Law

(57) ABSTRACT

The present invention relates to novel thiazolidinedione derivatives expressed by the following formula (I) and the uses thereof. More specifically, the present invention relates to novel thiazolidinedione derivatives expressed by the following formula (I) and a pharmaceutical composition comprising the same. The novel thiazolidinedione derivatives of formula (I) according to the present invention can be effectively used for the prevention or treatment of cardiovascular disease, gastrointestinal disease and renal disease by inhibiting the activity of 15-hydroxyprostaglandin dehydrogenase (15-PGDH) that decomposes prostaglandins as well as useful for the prevention of hair loss and the stimulation of hair growth, and osteogenic stimulation and wound healing.

7 Claims, No Drawings

THIAZOLIDINEDIONE DERIVATIVE AND USE THEREOF

FIELD OF THE INVENTION

The present invention relates to novel thiazolidinedione derivatives and the use thereof, specifically to novel thiazolidinedione derivatives and a pharmaceutical composition comprising the same.

BACKGROUND OF THE INVENTION

Prostaglandins are fatty acid derivatives composed of 20 carbon atoms with a 5-carbon ring. The name prostaglandin is derived from the prostate gland because the Swedish physiologist Ulf von Euler who first isolated prostaglandins in 1935 believed that they were secreted from the prostate gland. Now, it is known that they are ubiquitously found in mammalian tissues and metabolized rapidly after being synthesized from polyunsaturated fatty acids. Depending on the types thereof, the prostaglandins can stimulate the constriction of smooth muscle, or increase or decrease blood pressure or blood coagulation in some animals as well as promote ion transport across the membrane, stimulate inflammation and inhibit cardiovascular diseases and viral infection.

Meanwhile, prostaglandins and their homologues have short effective lives because they are chemically unstable and metabolized rapidly in vivo. It is not only because the active forms of prostaglandins and their homologues have hydroxyl and carboxyl groups, which are rapidly inactivated by enzymes, but also because their molecular weights are so low that they can be easily eliminated and excreted from the body (Narumiya S. et. al, 1999, *Physiol. Rev.,* 79(4), 1193-1226).

Such chemical instability and short effective life of prostaglandins and their homologues have severely restricted their use for the treatment of respiratory, genitourinary, neurotic, endocrine and cardiovascular diseases.

In order to solve the above problems, therefore, extensive studies have been conducted to develop a pharmaceutically acceptable formulation of prostaglandins and their homologues, which can provide an improved stability, various methods of administration, an increased activity and a longer effective life. For example, Korean Patent No. 598,660 discloses 5-thia-ω-substituted phenyl-prostaglandin E derivatives, which are capable of binding strongly to prostaglandin receptors to produce an excellent activity; Korean Patent No. 850,133 discloses prostaglandin nitrooxy-derivatives having an improved pharmacological activity and enhanced tolerability; and Korean Laid-open Patent Publication No. 2001-0023839 discloses aromatic $C_{16}$-$C_{20}$-substituted tetrahydroprostaglandins useful as FP agonists.

Meanwhile, the first step of the fast in vivo metabolism of prostaglandins, which results in their short physiological activity, is oxidation in which prostaglandins are inactivated by $NAD^+$ dependent 15-hydroxyprostaglandin dehydrogenase (15-PGDH) (Ensor, C. M, & Tai, H. H., 1995, *J. Lipid Mediator Cell Signalling* 12:313-319).

15-PGDH, which was first extracted and isolated from placenta, lung and kidney, is localized in mammalian tissues (Krook M et. al., 1990, *Biochemistry,* 29, 738-743). Since 15-hydroxyprostaglandin dehydrogenase (15-PGDH) is an enzyme that degrades prostaglandins, a large amount of prostaglandins are found in the tissues that do not express 15-PGDH. 15-PGDH oxidizes prostaglandin compounds containing a hydroxy group at the C-15 position to convert them into 15-ketoprostaglandins, thereby rendering these compounds biologically inactive (Tai H H et. al., 2002, *Adv Exp Med Biol,* 507, 245250).

According to the recent research results, it has been suggested that 15-PGDH plays a potential role in the carcinogenesis. The expression of 15-PGDH was found to be dramatically induced in the human prostate cancer cells treated by androgens as well as in the tumors derived from nude mice injected with human prostate cancer cells (M. Tong., 2000, *Biochem. Biophys. Res. Commun.,* 276, 77~81). Based on the above, many researchers expected that the suppression or the reduction of 15-PGDH expression could lead to the inhibition of carcinogenesis.

Accordingly, various researches for 15-PGDH inhibitors have been in progress, among which cyclooxygenase inhibitors, flavonoids, phytophenolic compounds and peroxisome proliferator-activated receptor γ (PPAR γ) were found to be effective in inhibiting 15-PGDH.

Under the circumstances, the present inventors have endeavored to develop a novel compound capable of inhibiting 15-PGDH and have found that novel thiazolidinedione derivatives having an excellent 15-PGDH inhibitory activity are effective in the stimulation of hair growth, the alleviation of cardiovascular diseases, gastrointestinal disorders and renal disorders, osteogenesis and wound healing.

SUMMARY OF THE INVENTION

It is, therefore, an object of the present invention to provide novel thiazolidinedione derivatives.

Another object of the present invention is to provide a pharmaceutical composition for inhibiting hair loss and stimulating hair growth containing the above derivative as an active ingredient.

Still another object of the present invention is to provide a pharmaceutical composition for the prevention or the treatment of cardiovascular disease containing the above derivative as an active ingredient.

A further object of the present invention is to provide a pharmaceutical composition for the prevention or the treatment of gastrointestinal disease containing the above derivative as an active ingredient.

A still further object of the present invention is to provide a pharmaceutical composition for the prevention or the treatment of renal disease containing the above derivative as an active ingredient.

Another object of the present invention is to provide a pharmaceutical composition for osteogenesis containing the above derivative as an active ingredient.

Still another object of the present invention is to provide a pharmaceutical composition for wound healing containing the above derivative as an active ingredient.

In order to accomplish the above objects, there is provided novel thiazolidinedione derivatives.

According to the present invention, a pharmaceutical composition for inhibiting hair loss and stimulating hair growth containing the above derivative as an active ingredient is provided.

Further, there is provided a pharmaceutical composition for the prevention or the treatment of cardiovascular disease containing the above derivative as an active ingredient.

Further, there is provided a pharmaceutical composition for the prevention or the treatment of gastrointestinal disease containing the above derivative as an active ingredient.

There is also provided a pharmaceutical composition for the prevention or the treatment of renal disease containing the above derivative as an active ingredient.

Also, there is provided a pharmaceutical composition for osteogenesis containing the above derivative as an active ingredient.

Furthermore, there is provided a pharmaceutical composition for wound healing containing the above derivative as an active ingredient.

Novel thioazolidinedione derivatives according to the present invention, which show an excellent inhibitory activity against 15-hydroxyprostaglandin dehydrogenase, are effective in the prevention or the treatment of cardiovascular diseases, gastrointestinal diseases and renal diseases that are associated with 15-PGDH. Further, they are useful for the inhibition of hair loss and the stimulation of hair growth, the promotion of osteogenesis and wound healing.

DETAILED DESCRIPTION OF THE PREFERRED EMBODIMENTS

In the present invention, novel thiazolidinedione derivatives expressed by the following formula (I) are provided:

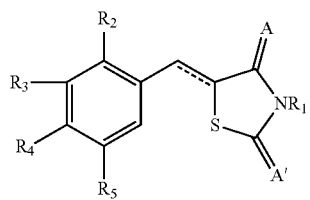

Wherein, A and A' are each independently O or S; $R^1$ is hydrogen or $CH_2CH_2OH$; $R_2$, $R_3$, $R_4$ and $R_5$ may be each independently selected from hydrogen, nitro, amine, alkoxy, alkyl, trifluoromethyl, carboxyl, halogen or

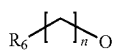

where said

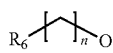

may bind to the C3- or C4-position of the benzene ring; R6 may be selected from the group consisting of hydrogen, methyl, ethyl, unsubstituted or substituted (hetero)cycloalkyl, (hetero)cycloalkenyl or (hetero)aryl; the dotted line indicates a single or a double bond; and n may be an integer from 0 to 5.

Further, in the above formula, in case that $R_3$ is

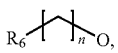

$R_2$, $R_4$ and $R_5$ may be each independently selected from the group consisting of H, $NO_2$, $NH_2$, $CH_3$, Cl, Br, F, COOH, $CF_3$, $CH_3O$ and $CH_3CH_2O$; and in the case that $R_4$ is

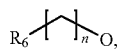

$R_2$, $R_3$ and $R_5$ may be each independently selected from the group consisting of H, $NO_2$, $NH_2$, $CH_3$, Cl, Br, F, COOH, $CF_3$, $CH_3O$ and $CH_3CH_2O$.

The definitions of the terms used for describing the derivatives of the above formula (I) according to the present invention will be explained below. Unless otherwise indicated for a specific case individually or as a part of a genus group, the following definitions are intended to apply uniformly throughout the specification and claims.

The term "alkyl" refers to an unsubstituted or substituted straight or branched hydrocarbon group having 1 to 20 carbon atoms, preferably 1 to 7 carbon atoms. Representatives of unsubstituted alkyl group include methyl, ethyl, propyl, isopropyl, n-butyl, t-butyl, isobutyl, pentyl, hexyl, isohexyl, heptyl, 4,4-dimethylpentyl, octyl and the like. The examples of substituted alkyl group include, but are not limited to alkyl groups substituted by at least one selected from the group consisting of halo, hydroxy, cycloalkyl, alkanoyl, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, aryl, alkenyl, alkynyl, aralkoxy, guanidino, indolyl, imidazolyl, furyl, thienyl, thiazolyl, pyrrolidnyl, pyridyl, pyrimidyl, piperidyl and morphonyl.

The term "halogen" refers to fluoro, chloro, bromo and iodo.

The term "alkenyl" refers to any alkyl groups having at least two carbon atoms, preferably 2 to 4 carbon atoms, and containing a double bond.

The term "aryl" refers to a monocyclic or bicyclic aromatic hydrocarbon group having 6 to 12 carbon atoms in its ring, for example, phenyl, naphthyl, tetrahydronaphthyl, biphenyl and diphenyl, each of which can be optionally substituted by 1 to 4 substituents such as alkyl, halo, hydroxy, alkoxy, acyl, alkanoyloxy, optionally substituted amino, thiol, alkylthio, nitro, cyano, carboxy, carboxyalkyl, alkoxycarbonyl, carbamoyl, alkylthiono, sulfonyl, sulfonamido, heterocyclyl and the like.

The term "cycloalkyl" refers to a monocyclic, bicyclic or tricyclic hydrocarbon group having 3 to 12 carbon atoms, which may be optionally substituted by at least one substituent, for example, by alkyl, halo, oxo, hydroxy, alkoxy, alkanoyl, acylamino, carbamoyl, alkylamino, dialkylamino, thiol, alkylthio, nitro, cyano, carboxy, carboxyalkyl, alkoxycarbonyl, sulfonyl, sulfonamido, sulfamoyl, heterocyclyl, etc.

The term "heterocyclo" refers to an optionally substituted saturated or unsaturated aromatic or non-aromatic cyclic group having at least one heteroatom in the ring containing at least one carbon atom. Each ring of the heterocyclic group(s) may have one, two or three heteroatoms selected from nitrogen atom, oxygen atom and sulfur atom. The heterocyclic group may bind to either a heteroatom or a carbon atom.

Preferred embodiments of the novel thiazolidinedione derivatives expressed by the above formula (I) include those prepared in Examples 1 to 130 of the specification.

Further, according to the present invention, there are provided salts, preferably, pharmaceutically acceptable salts of the thiazolidinedione derivatives expressed by the above formula (I). The "pharmaceutically acceptable salts" as used herein indicates the salts suitable for use in contact with the tissues of humans and lower animals without undue toxicity, irritation and side effects, etc. within the scope of sound medical judgment. Such pharmaceutically acceptable salts have been well known in the art (S. M. Berge et al., 1977, *J. Parmaceutical Sciences*, 66:1). During the final isolation, purification and synthesis of the derivatives according to the present invention, the salts can be prepared in situ or by being separately reacted with an inorganic or organic base. The derivatives according to the present invention, if they contain an acidic group, can react with bases to form salts, which include, but are not limited to alkali metal salts such as lithium salts, sodium salts and potassium salts; alkaline earth metal salts such as barium salts or calcium salts; other metal salts such as magnesium salts; salts with organic bases such as dicyclohexylamine; and salts with basic amino acids such as lysine or arginine. Further, in case that the derivatives in accordance with the present invention contain a basic group within the molecule, they can form acid addition salts, which include, but are not limited to salts with inorganic acids, preferably, halogenated hydroacid such as hydrofluoric acid, hydrobromic acid, hydroiodic acid or hydrochloric acid, nitric acid, carbonic acid, sulfuric acid or phosphoric acid; salts with lower alkyl-sulfonic acids such as methanesulfonic acid, trifluoromethanesulfonic acid or ethanesulfonic acid; salts with benzenesulfonic acid or p-toluenesulfonic acid; salts with organic carboxylic acids such as acetic acid, fumaric acid, tartaric acid, oxalic acid, maleic acid, malic acid, succinic acid or citric acid; and salts with amino acids such as glutamic acid or aspartic acid.

In addition, the present invention provides novel thiazolidinedione derivatives expressed by formula (I) in the form of hydrates or solvates (J. M. Keith, 2004, *Trahedron Letters*, 45(13), 2739-2742).

Novel thiazolidinedione derivatives in accordance with the present invention can be isolated from nature or chemically synthesized from thiazolidinedione compounds known in the art. Generally, a compound having a substituent to be substituted at the 5-position of a thioazolidinedione is reacted in a suitable reaction solvent to afford a intermediate product, which is then reacted with 2,4-thiazolidinedione in a suitable reaction solvent to obtain the derivative according to the subject invention.

Any reaction solvent can be used in the above preparation process as long as it is not involved in the reaction. For example, the reaction solvent includes ethers such as diethyl ether, tetrahydrofuran and dioxan; halogenized hydrocarbons such as dichloromethane and chloroform; amines such as pyridine, piperidine and triethylamine; alkylketons such as acetone, methylethylketone and methylisobutyl; alcohols such as methanol, ethanol and propanol; non-protonic polar solvent such as N,N-dimethylformamide, N,N-dimethylacetamide, acetonitrile, dimethylsulfoxide and hexamethyl phosphoric acid triamide. Among non-reactive organic solvents that are ordinarily used in the organic synthesis, preferable solvents are those from which water generated in the reaction can be removed by a Dean-Stark trap. The examples of such solvents include, but are not limited to benzene, toluene, xylene and the like. The reaction product thus obtained may be isolated and purified by condensation, extraction and the like, which is ordinarily conducted in the field of the organic synthesis, if desired, by silica gel column chromatography.

Further, the present invention includes any modifications for the preparation method of novel thiazolidinedione derivatives. In this connection, any intermediate product obtainable from any step of the preparation method can be used as a starting material in the other steps. Such starting material can be formed in situ under certain reaction conditions. Reaction reagents can also be used in the form of their salts or optical isomers.

Depending on the kinds of the substituents to be used in the preparation of the derivatives, and the intermediate product and the preparation method selected, novel thiazolidinedione derivatives according to the present invention can be in the form of any possible isomers such as substantially pure geometrical(cis or trans) isomers, optical isomers(enantiomers) and racemates, which are all included within the scope of the present invention.

Meanwhile, novel thiazolidinedione derivatives of the present invention expressed by formula (I) are characterized by a suppressive or inhibitory activity against 15-hydroxy prostaglandin dehydrogenase (15-PGDH).

The activated level of 15-PGDH can be confirmed by determining the amount of NADH because 15-PGDH reduces NAD+ into NADH, thereby catalyzing oxidation of prostaglandins to inactivated 15-ketoprostaglandin.

In one experimental example, therefore, the amount of NADH generated was determined in the cells treated by novel thiazolidinedione derivatives according to the present invention, in order to identify the suppressive or inhibitory activity of the derivatives against 15-hydroxy prostaglandin dehydrogenase (15-PGDH).

As a result, the present inventors confirmed that novel thiazolidinedione derivatives of the present invention produce an inhibitory activity against 15-hydroxy prostaglandin dehydrogenase (15-PGDH) (see Experimental Example 1).

Accordingly, it has been discovered by the present inventors that novel thiazolidinedione derivatives according to the present invention as 15-PGDH inhibitors can be used for the prevention or the treatment of diseases that are associated with 15-PGDH.

Meanwhile, it has been known that prostaglandins play an important role in hair growth; specifically, internal storage of various types ($A_2$, $F_{2a}$, $E_2$) of prostaglandins in the various compartments of hair follicles or their adjacent skin environments was shown to be essential in maintaining and increasing hair density (Colombe L et. al, 2007, *Exp. Dermatol*, 16(9), 762-9). However, it has been reported that an enzyme specifically involved in the degradation of prostaglandins is present in the hair follicle dermal papillae, which is crucial compartments for hair survival; the enzyme, 15-PGDH, inactivates prostaglandins, especially, $PGF_{2a}$ and $PGE_2$, to cause scalp damage and alopecia (Michelet J F et. al., 2008, *Exp. Dermatol*, 17(10), 821-8).

Thus, novel thiazolidinedione derivatives according to the present invention, which have a suppressive or inhibitory activity against 15-PGDH that degrades prostaglandins, can improve scalp damage, prevent alopecia and promote hair growth.

Consequently, the present invention provides a pharmaceutical composition for the prevention of alopecia and the promotion of hair growth containing the novel thiazolidinedione derivative according to the present invention as an active ingredient.

The term "alopecia" as used herein indicates the general condition of hair follicles showing partial or general permanent hair loss. The targets of alopecia or hair growth can be human keratin fibers, especially, hair, eyebrow, eyelashes, mustache, beard and the like.

Further, the present invention provides a pharmaceutical composition for the prevention or the treatment of cardiovascular disease containing the novel thiazolidinedione derivative according to the present invention as an active ingredient.

Prostaglandins including prostaglandin homologues produced in the body have been known to maintain the proper action of the blood vessel wall, especially to contribute to vasodilation for blood flow, preventing platelet aggregation and modulating the proliferation of smooth muscle that surrounds blood vessel walls (Yan. Cheng et. al., 2006, *J. Clin., Invest*). In addition, the inhibition of prostaglandins production or the loss of their activity causes the degeneration of the endothelium in the blood vessel walls, platelet aggregation and the dysfunction of cellular mechanism in the smooth muscle, which leads to cardiovascular diseases. Among others, the production of prostaglandins in blood vessels was shown to be decreased in hypertension patients (Tang E H, 2008, *Cardiovasc Res.*, 78(1), 130-8).

Accordingly, novel derivatives according to the present invention, which have a suppressive or inhibitory activity against 15-PGDH that degrades prostaglandins, can store and activate prostaglandins such as $PGE_2$ so as to prevent or treat cardiovascular diseases.

The term "cardiovascular disease(s)" as used herein includes those caused by hypercholesterolemia, which is defined as an abnormally high level of Low Density Lipoprotein cholesterol ("LDL-cholesterol"), cholesterol and triglyceride in the blood, as well as those caused by the degeneration of the endothelium in blood vessel walls, platelet aggregation or the dysfunction of cellular mechanism in smooth muscle. Examples of the cardiovascular diseases include, but are not limited to arteriosclerosis, hypertension, angina, hyperlipidemia, myocardial infarction and heart failure.

Further, the present invention provides a pharmaceutical composition for the prevention or the treatment of gastrointestinal diseases containing the novel thiazolidinedione derivative according to the present invention as an active ingredient.

Gastritis and gastric ulcer, representatives of the gastrointestinal diseases, are defined as the conditions where gastrointestinal mucus membrane is digested by gastric acid to form ulcer. In the stomach walls generally consisting of mucosa, submucosa, muscle layer and serosa, gastric ulcer even damages submucosa and muscle layer, while gastritis damages mucosa only.

Although the mobility rates of gastritis and gastric ulcer are relatively high, the causes thereof have not been clarified yet. Until now, they are known to be caused by an imbalance between aggressive factors and defensive factors, that is, the increase in aggressive factors such as the increase in gastric acid or pepsin secretion, or the decrease in defensive factors such as structural or morphological deficit of the gastric mucus membrane, the decrease in mucus and bicarbonate ion secretion, the decrease in prostaglandin production, or the like.

Currently available therapeutic agents for gastritis and gastric ulcer comprise various drugs for strengthening the defensive factors such as an antacid, which does not affect, gastric acid secretion but neutralizes gastric acid that has been already produced, an inhibitor of gastric acid secretion, a promoter of prostaglandin secretion, and a coating agent for stomach walls. Especially, prostaglandins are known to be essential in maintaining the mechanism for protecting and defending gastric mucus membrane (Wallace J L., 2008, *Physiol Rev.*, 88(4), 1547-65, S. J. Konturek et al., 2005, *Journal of Physiology and Pharmacology*, 56(5), 5~31).

In view of the above, since novel thiazolidinedione derivatives according to the present invention show a suppressive or inhibitory activity against 15-PGDH, which degrades prostaglandins that protect gastric mucus membrane, they can be effective for the prevention or the treatment of gastrointestinal diseases, inter alia, gastritis and gastric ulcer.

In the kidney, prostaglandins modulate renal blood flow and may serve to regulate urine formation by both renovascular and tubular effects. In clinical studies, $PGE_1$ has been used to improve creatinine clearance in patients with chronic renal disease, to prevent graft rejection and cyclosporine toxicity in renal transplant patients, to reduce the urinary albumin excretion rate and N-acetyl-beta-D-glucosaminidase levels in patients with diabetic nephropathy (see Porter, Am., 1989, *J. Cardiol.*, 64: 22E-26E). In addition, U.S. Pat. No. 5,807,895 discloses a method of preventing renal dysfunction by intravenous administration of prostaglandins such as $PGE_1$, $PGE_2$ and $PGI_2$. Furthermore, it has been reported that prostaglandins serve as vasodilators in the kidney, and, thus, the inhibition of prostaglandin production in the kidney results in renal dysfunction (Hao. C M, 2008, *Annu Rev Physiol*, 70, 357~77).

Thus, novel derivatives according to the present invention, which have a suppressive or inhibitory activity against 15-PGDH that degrades prostaglandins, may be effective in the prevention or the treatment of renal diseases that are associated with renal dysfunction.

The term "renal dysfunction" as used herein includes such manifestations as follows: lower than normal creatinine clearance, lower than normal free water clearance, higher than normal blood urea, nitrogen, potassium and/or creatinine levels, altered activity of kidney enzymes such as gamma glutamyl synthetase, alanine phosphatidase, N-acetyl-beta-D-glucosaminidase, or beta-w-microglobulin; and increase over normal levels of macroalbuminuria.

Therefore, the present invention provides a pharmaceutical composition for the prevention or the treatment of renal disease containing the novel thiazolidine derivative according to the present invention as an active ingredient.

As discussed in the above, novel thiazolidine derivatives according to the present invention serve as 15-PGDH inhibitors and may be useful for the prevention of alopecia and the promotion of hair growth as well as the prevention or the treatment of cardiovascular, gastrointestinal and renal diseases by inhibiting prostaglandin degradation.

Meanwhile, prostaglandins including $PGE_1$, $PGE_2$ and $PGF_{2a}$ were shown to stimulate bone resorption and bone formation to increase the volume and the strength of the bone (H. Kawaguchi et. al., *Clinical Orthop. Rel. Res.*, 313, 1995, 36~46; J. Keller et. al., *Eur. Jr. Exp. Musculoskeletal Res.*, 1, 1992, 8692).

Considering that 15-PGDH inhibits the activities of prostaglandins as mentioned in the above, the inhibition of 15-PGDH activity may lead to the promotion of bone resorption and bone formation that are inhibited by 15-PGDH.

Thus, novel thiazolidinedione derivatives according to the present invention can be effective for the promotion of bone resorption and bone formation by inhibiting 15-PGDH activity.

Based on the above, the present invention provides a pharmaceutical composition for osteogenesis containing the novel thiazolidinedione derivative according to the present invention as an active ingredient.

Further, novel thiazolidinedione derivatives according to the present invention are effective for wound healing.

Among various prostaglandins, $PGE_2$ is known to serve as a mediator for wound healing. Therefore, when skin is injured by wounds or burns, the inhibition of 15-PGDH activity can produce the treatment effect of the wounds or the burns by $PGE_2$.

In view of the above, since novel thiazolidinedione derivatives according to the present invention, which produce an excellent inhibitory activity against 15-PGDH, can treat wounds or burns, the present invention provides a pharmaceutical composition for wound healing containing the novel thiazolidinedione derivative according to the present invention as an active ingredient.

The term "15-PGDH inhibitor" as used herein includes a compound capable of inhibiting or decreasing the activity of 15-PGDH enzyme, or inhibiting, decreasing or retarding any reaction catalyzed by the enzyme but specifically means derivatives having formula (I).

A pharmaceutical composition containing the derivative having formula (I) according to the present invention as an active ingredient may be manufactured by mixing the derivative with a pharmaceutically acceptable carrier(s) or an excipient(s) or diluting the derivative with a diluent(s) in accordance with conventional methods. The pharmaceutical composition may further contain fillers, anti-cohesives, lubricants, wetting agents, flavoring agents, emulsifying agents, preservatives and the like. The pharmaceutical composition according to the present invention may be formulated into a suitable formulation in accordance with the methods known to those skilled in the art so that it can provide an immediate, controlled or sustained release of the derivative after being administered into a mammal.

The pharmaceutical composition according to the present invention may be formulated into a parenteral or oral dosage form. The solid dosage form for oral administration may be manufactured by adding excipient, if necessary, together with binder, disintegrants, lubricants, coloring agents, and/or flavoring agents, to a derivative according to the present invention and shaping the resulting mixture into the form of tablets, sugar-coated pills, granules, powder or capsules. The additives that can be added in the composition according to the present invention may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, polyethylene glycol, etc. may be used as a lubricant according to the present invention; and sucrose, bitter orange peel, citric acid, tartaric acid, etc. may be used as a flavoring agent according to the present invention.

The compounds of the present invention may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

The compounds of the present invention may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

The compounds of the present invention may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The compounds of the present invention may also be incorporated into ointments in accordance with conventional methods. In this case, bases, stabilizing agents, moisturizing agents, preservatives and the like that are ordinarily used in the manufacture of ointments may be added to the compounds of the present invention. Examples of the bases include liquid paraffin, white vaseline, white wax, octyl dodecyl alcohol and paraffin. Examples of the preservatives include methyl para-oxybenzoate, ethyl para-oxybenzoate and propyl para-oxybenzoate.

The pharmaceutical composition according to the present invention may be formulated into various dosage forms as discussed above and then administered through various routes including an oral, transdermal, subcutaneous, intravenous or intramuscular route.

The term "pharmaceutically effective amount" as used herein refers to an amount of the compound sufficient to treat or improve alopecia, cardiovascular disease, gastrointestinal disease and renal disease. The pharmaceutically effective amount of the compound will be appropriately determined depending on the kind and the severity of the disease to be treated, age, sex, body weight and the physical condition of the patients to be treated, administration route, duration of therapy and the like. Generally, the effective amount of the compound may be in the range of about 1 to 1,000 mg in the oral administration, about 0.1 to 500 mg in the intravenous administration, about 5 to 1,000 mg in the rectal administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation of the present invention may be administered once a day or several times a day with a divided dose.

The present invention will now be described in more detail with reference to the following examples. However, these examples are given by way of illustration only not of limitation.

BEST MODE FOR CARRYING OUT THE INVENTION

Synthesis of the Derivatives According to the Present Invention

In the following examples, prostaglandin ($PGE_2$), $NAD^+$, NADH, glutathione sepharose 4B, DTT, sodium dodecyl sulfate(SDS), EDTA and reduced glutathione used in the experiments for determining the activity of the derivatives according to the present invention were purchased from Sigma, U.S.A. The cDNA of human 15-PGDH was cloned from human placental cDNA library. UV spectra and NMR spectra were obtained using an UV-VIS Spectrophotometer from Shimadzu Corporation and an JEOL JNM-LA 300 spectrometer from JEOL, Tokyo, Japan, respectively.

Example 1

Preparation of Derivative 1 According to the Present Invention

Derivative 1 having the following formula was prepared as follows.

[Formula of Derivative 1]

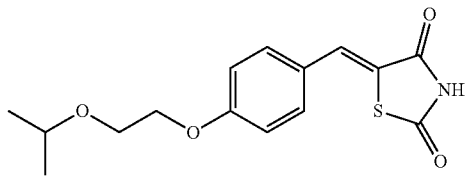

Step 1: To a solution of 2-isopropoxyethanol (600 mg, 5.76 mmol), p-hydroxybenzaldehyde (0.78 g, 6.34 mM) and triphenylphosphine in THF (20 ml) (1.6 g, 6.1 mmol), diethyl azodicarboxylate (40% in toluene) was added at 0° C. over 10 minutes while stirring. Then, the mixture was stirred at room temperature for 18 hours until the initial reaction product of 2-isopropoxyethanol and p-hydroxybenzaldehyde disappeared. The resulting solution was concentrated and purified by silica gel chromatography (hexane:ethylacetate=5:1) to obtain 4-(2-isopropoxyethoxy)benzaldehyde as yellow oil (0.98 g, yield: 82%).

$^1$H NMR (300 MHz, CDCl$_3$): δ 9.87 (s, 1H), 7.82 (d, J=9 Hz, 2H), 6.97 (d, J=9 Hz, 2H), 4.19 (t, J=9.9 Hz, 2H), 3.81 (t, J=10.2 Hz, 2H), 3.63-3.75 (m, J=24.3 Hz, 1H), 1.20 (d, J=0.36 Hz, 6H)

Step 2: 4-(2-isopropoxyethoxy)benzaldehyde obtained in step (0.98 g, 4.71 mmol) and 2,4-thiazolidinedione (0.55 g, 4.71 mmol) were dissolved in 20 ml of toluene, piperidine (0.23 ml, 2.36 mmol) and acetic acid (0.13 ml, 2.36 mmol) were subsequently added thereto, and the resulting solution was heated overnight under reflux in a Dean-Stark water trap. Then, the mixture thus obtained was cooled and filtered. The precipitate was washed with ether or hexane and dried to afford Derivative 1 having the above formula, (5-(4-(2-isopropoxyethoxy)benzylidene)thiazolidine-2,4-dione) (1.26 g, yield: 87.5%) as yellow solid.

$^1$H NMR (300 MHz, CDCl$_3$): δ 8.04 (s, 1H), 7.805 (s, 1H), 7.432 (d, J=9 Hz, 2H), 7.022 (d, J=9 Hz, 2H), 4.19 (t, J=9.6 Hz, 2H), 3.84 (t, J=9.6 Hz, 2H), 3.65-3.76 (m, J=24.6 Hz, 1H), 1.24 (d, J=6 Hz, 6H)

Example 2

Preparation of Derivative 2 According to the Present Invention

Derivative 2 having the following formula was prepared as follows.

[Formula of Derivative 2]

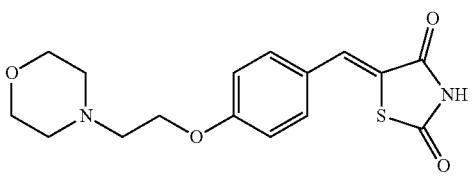

To dried dimethylformamide (20 ml) solution in which 4-(2-hydroxyethyl)morpholine (1 g, 7.62 mmol) was dissolved, sodium hydride (201.2 mg, 8.38 mmol) was slowly added under nitrogen at room temperature. The mixture was stirred for 30 minutes at room temperature, and 4-fluorobenzaldehyde (1.1 g, 8.86 mmol) in dried dimethylformamide (5 ml) was added over 10 minutes. The reaction mixture was stirred at room temperature for 18 hours until the initial reaction product disappeared. Subsequently, 20 ml of ice water was added to the resulting mixture, and the mixture was extracted with ethyl acetate and water. The organic layer was washed with water several times, dried over anhydrous magnesium sulfate, filtered and solvent-evaporated. The residual oil was purified by silica gel column chromatography (hexane:ethyl acetate=5:1) to afford the intermediate compound 4-(2-(morpholinoethoxy)benzaldehyde (1.42 g, 79%).

$^1$H NMR (300 MHz, CDCl$_3$) δ 10.17 (s, 1H), 7.85 (d, J=8.7 Hz, 2H), 7.00 (d, J=8.7 Hz, 2H), 4.19 (t, J=11.4 Hz, 2H), 3.74 (t, J=9.0 Hz, 4H), 2.83 (t, J=11.4 Hz, 2H), 2.59 (t, J=9 Hz, 4H)

Derivative 2 having the above formula, (5-(4-(2-morpholinoethoxy)benzylidene)thiazolidine-2,4-dione) was prepared from 4-(2-(morpholinoethoxy)benzaldehyde (1 g, 4.3 mmol) prepared in the above and 2,4-thiazolidinedione (504 mg, 4.3 mmol) in accordance with Step 2 of Example 1 (yield: 90%).

$^1$H NMR (300 MHz, DMSO-d6): δ 8.14 (s, 1H), 7.705 (s, 1H), 7.544 (d, J=8.7 Hz, 2H), 7.104 (d, J=8.7 Hz, 2H), 4.15 (t, J=11.4 Hz, 2H), 3.57 (m, J=9.0 Hz, 8H), 2.722 (t, J=11.4 Hz, 2H)

Example 3

Preparation of Derivative 3 According to the Present Invention

Derivative 3 having the following formula was prepared as follows.

[Formula of Derivative 3]

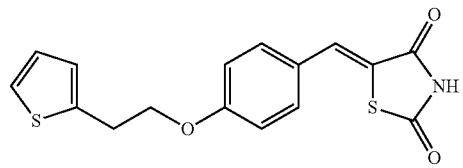

First, the intermediate, 4-(2-thiophene ethoxy)benzaldehyde, was prepared in accordance with the same method as described in Step 1 of Example 1, except that 2-thiophene ethanol was added in place of 2-isopropoxyethanol (yield: 94%).

$^1$H NMR (300 MHz, CDCl$_3$): δ 9.89 (s, 1H), 7.85 (d, J=10.2 Hz, 2H), 7.20 (dd, J=1.2, 1.2 Hz, 1H), 7.03 (d, J=10.2 Hz, 2H), 6.92-6.98 (m, J=16.2 Hz, 2H), 4.30 (t, J=12.5 Hz, 2H), 3.37 (t, J=12.5 Hz, 2H)

Then, Derivative 3 having the above formula, 5-(4-(2-(thiophen-2-yl)ethoxy)benzylidene)thiazolidine-2,4-dione, was obtained in accordance with the same method as described in Step 2 of Example 1, except that 4-(2-isopropoxyethoxy)benzaldehyde was replaced by the intermediate prepared in the above (yield: 90%).

$^1$H NMR (300 MHz, DMSO-d6): δ 8.12 (s, 1H), 7.73 (s, 1H), 7.558 (d, J=8.7 Hz, 2H), 7.354 (dd, J=1.2, 1.2 Hz, 1H), 7.12 (d, J=8.7 Hz, 2H), 6.942-6.973 (m, J=9.3 Hz, 2H), 4.28 (t, J=12.6 Hz, 2H), 3.285 (t, J=12.5 Hz, 2H)

Example 4

Preparation of Derivative 4 According to the Present Invention

Derivative 4 having the following formula was prepared as follows.

[Formula of Derivative 4]

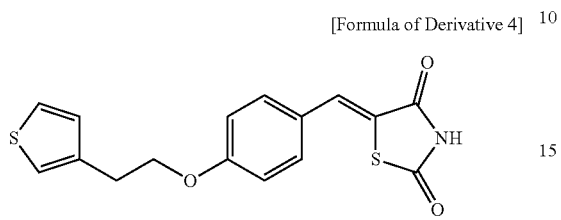

The intermediate, 4-(2-(thiophen-3-yl)ethoxy)benzaldehyde was prepared in accordance with the same method as described in Step 1 of Example 1, except that 3-thiophene ethanol was added in place of 2-isopropoxyethanol (yield: 94%).

$^1$H NMR (300 MHz, CDCl$_3$): δ 9.89 (s, 1H), 7.86 (d, J=13.8 Hz, 2H), 7.03 (d, J=13.8 Hz, 2H), 4.20 (t, J=10.5 Hz, 2H), 3.20 (dd, J=10.2, 10.2 Hz, 8H), 3.04 (t, J=10.5 Hz, 2H)

Then, Derivative 4 having the above formula, 5-(4-(2-(thiophen-3-yl)ethoxy)benzylidene)thiazolidine-2,4-dione, was obtained in accordance with the same method as described in Step 2 of Example 1, except that 4-(2-isopropoxyethoxy)benzaldehyde was replaced by the intermediate prepared in the above (yield: 90%).

$^1$H NMR (300 MHz, DMSO-d6): δ 8.12 (s, 1H), 7.69 (s, 1H), 7.556 (d, J=11.7 Hz, 2H), 7.45 (d, J=3 Hz, 3 Hz, 1H), 7.305 (s, 1H), 7.11 (d, J=11.7 Hz, 2H), 4.28 (t, J=13.8 Hz, 2H), 3.07 (t, J=13.8 Hz, 2H)

Example 5

Preparation of Derivative 5 According to the Present Invention

Derivative 5 having the following formula was prepared as follows.

[Formula of Derivative 5]

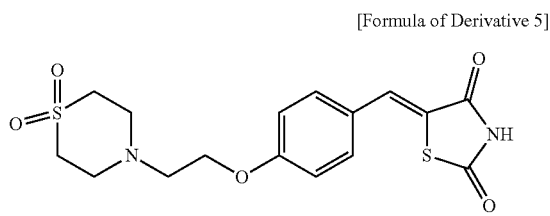 [SMILES: O=C1NC(=O)/C(=C/c2ccc(OCCN3CCS(=O)(=O)CC3)cc2)S1]

The intermediate, 4-(2-thiomorpholine-1,1-dioxideethoxy)benzaldehyde, was prepared in accordance with the same method as described in Step 1 of Example 1, except that 2-thiomorpholine-1,1-dioxide ethanol was added in place of 2-isopropoxyethanol (yield: 95%).

$^1$H NMR (300 MHz, CDCl3): δ 9.90 (s, 1H), 7.87 (d, J=13.8 Hz, 2H), 7.03 (d, J=13.8 Hz, 2H), 4.20 (t, J=10.5 Hz, 2H), 3.20 (dd, J=10.2, 10.2 Hz, 8H), 3.04 (t, J=10.5 Hz, 2H)

Then, Derivative 5 having the above formula, 5-[4-(2-thiomorpholine-1,1-dioxideethoxy)benzylidene]thiazolidine-2,4-dione was prepared in accordance with the same method as described in Step 2 of Example 1, except that 4-(2-isopropoxyethoxy)benzaldehyde was replaced by the intermediate obtained in the above (yield: 96%)

$^1$H NMR (300 MHz, DMSO-d6): δ 8.19 (s, 1H), 7.73 (s, 1H), 7.56 (d, J=8.7 Hz, 2H), 7.11 (d, J=8.7 Hz, 2H), 4.169 (t, J=10.8 Hz, 2H), 3.086 (dd, J=10.2, 10.2 Hz, 8H), 2.945 (t, J=10.8 Hz, 2H)

Example 6

Preparation of Derivative 6 According to the Present Invention

Derivative 6 having the following formula was prepared as follows.

[Formula of Derivative 6]

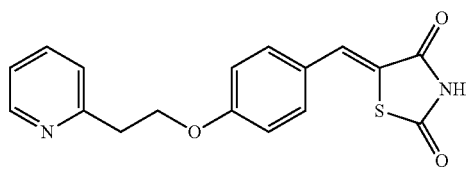

The intermediate, 4-(2-(pyridin-2-yl)ethoxy)benzaldehyde, was prepared in accordance with the same method as described in Step 1 of Example 1, except that 2-pyridine ethanol was added in place of 2-isopropoxyethanol (yield: 85%).

$^1$H NMR (300 MHz, DMSO-d6): δ 9.86 (s, 1H), 8.572 (d, J=4.5 Hz, 1H), 7.834 (d, J=8.7 Hz, 2H), 7.64 (d, J=1.8 Hz, 1H), 7.199 (m, J=13.2 Hz, 1H), 7.278 (m, J=4.8 Hz, 1H), 7.025 (d, J=8.7 Hz, 2H), 4.489 (t, J=13.5 Hz, 2H), 3.32 (t, J=13.5 Hz, 2H)

Then, Derivative 6 having the above formula, 5-(4-(2-(pyridin-2-yl)ethoxy)benzylidene)thiazolidine-2,4-dione, was obtained in accordance with the same method as described in Step 2 of Example 1, except that 4-(2-isopropoxyethoxy)benzaldehyde was replaced by the above intermediate compound (yield: 90%).

$^1$H NMR (300 MHz, DMSO-d6): δ 10.36 (s, 1H), 8.452 (d, J=4.8 Hz, 1H), 7.783 (s, 1H), 7.719 (t, J=17.4 Hz, 1H), 7.488 (d, J=8.4 Hz, 2H), 7.277 (d, J=7.11, 1H), 7.232 (m, J=12.6 Hz, 1H), 4.169 (t, J=14.7 Hz, 2H), 3.048 (t, J=14.7 Hz, 2H)

Example 7

Preparation of Derivative 7 According to the Present Invention

Derivative 7 having the following formula was prepared as follows.

[Formula of Derivative 7]

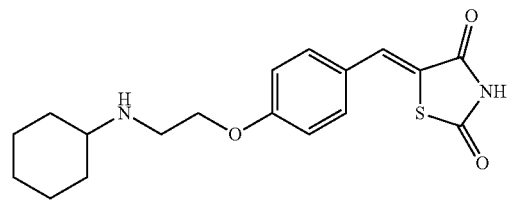

The intermediate, 4-(2-cyclohexylamino)ethoxybenzaldehyde was prepared in accordance with the same method as described in Example 2, except that N-cyclohexyl ethanolamine was added in place of 4-(2-hydroxyethyl)morpholine (yield: 79%).

¹H NMR (300 MHz, CDCl3): δ 9.81 (s, 1H), 7.772 (d, J=8.7 Hz, 2H), 6.953 (d, J=8.7 Hz, 2H), 4.108 (t, J=10.5 Hz, 2H) 3.013 (t, J=10.5 Hz, 2H), 2.072 (s, 1H). 2.470 (m, J=20.4 Hz, 1H), 2.072 (s, 1H), 1.838-1.148 (m, 10H)

Then, Derivative 7 having the above formula, 5-(4-(2-(cyclohexylamino)ethoxy)benzylidene)thiazolidine-2,4-dione was obtained in accordance with the same method as described in Step 2 of Example 1, except that 4-(2-isopropoxyethoxy)benzaldehyde was replaced by the above intermediate compound (yield: 82%).

¹H NMR (300 MHz, DMSO-d6): δ 7.504 (d, J=8.7 Hz, 2H), 7.310 (s, 1H), 7.069 (d, J=8.7 Hz, 2H), 4.244 (t, J=9.9 Hz, 2H), 3.299 (t, J=9.9 Hz, 2H), 3.017 (s, 1H), 2.284 (s, 1H), 2.071 (s, 2H) 1.894 (s, 2H), 1.61 (d, J=11.7 Hz), 1.304 (m, 5H)

Example 8

Preparation of Derivative 8 According to the Present Invention

Derivative 8 having the following formula was prepared as follows.

[Formula of Derivative 8]

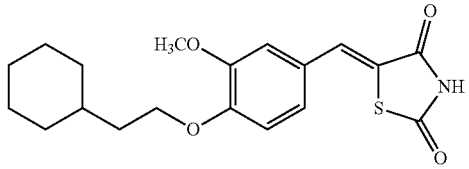

The intermediate, 4-(2-cyclohexylethoxy)-3-methoxybenzaldehyde was prepared in accordance with the same method as described in Example 2, except that cyclohexylethanol and 4-fluoro-m-anisadehyde were added in place of 4-(2-hydroxyethyl)morpholine and 4-fluorobenzaldehyde, respectively (yield: 85%).

¹H NMR (300 MHz, CDCl3): δ 9.774 (s, 1H), 7.383 (s, 1H), 7.365 (d, J=11.7 Hz, 1H), 6.912 (d, J=11.7 Hz, 1H), 4.096 (t, J=9.9 Hz, 2H), 3.846 (s, 3H), 1.617-1.755 (m, 8H), 1.388-1.46 (m, 1H), 1.146-1.258 (m, 2H), 0.87-0.978 (m, 2H)

Then, Derivative 8 having the above formula, 5-(4-(2-cyclohexylethoxy)-3-methoxybenzylidene)thiazolidine-2,4-dione was obtained in accordance with the same method as described in Step 2 of Example 1, except that 4-(2-isopropoxyethoxy)benzaldehyde was replaced by the above intermediate compound (yield: 89%).

¹H NMR (300 MHz, DMSO-d6): δ 8.221 (s, 1H), 7.728 (s, 1H), 7.028 (d, J=10.2 Hz, 2H), 6.924 (d, J=10.2 Hz, 2H), 6.895 (s, 1H), 4.074 (t, J=14.4 Hz, 2H), 3.846 (s, 1H), 1.716 (t, J=14.4 Hz, 2H), 1.620 (m, 1H), 1.434-1.515 (m, 4H), 1.078-1.214 (m, 4H), 0.867-0.976 (m, 2H)

Example 9

Preparation of Derivative 9 According to the Present Invention

Derivative 9 having the following formula was prepared as follows.

[Formula of Derivative 9]

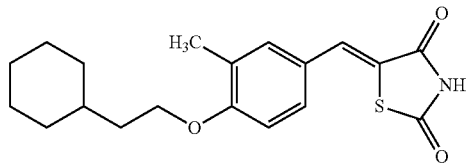

The intermediate product was prepared in accordance with the same method as described in Example 1, except that cyclohexylethanol and 4-hydroxy-3-methylbenzaldehyde were added in place of 2-isopropoxyethanol and p-hydroxybenzaldehyde, respectively (yield: 89%).

¹H NMR (300 MHz, CDCl3): δ 9.845 (s, 1H), 7.707 (d, J=8.7 Hz, 2H), 7.678 (s, 1H), 6.89 (d, J=8.7 Hz, 2H), 4.111 (t, J=13.2 Hz, 2H), 2.259 (s, 3H), 1.749 (t, J=13.2 Hz, 2H) 1.493-1.585 (m, 5H), 1.217-1.325 (m, 5H), 1.009-1.048 (m, 1H)

Then, Derivative 9 having the above formula, 5-(4-(2-cyclohexylethoxy)-3-methylbenzylidene)thiazolidine-2,4-dione was obtained in accordance with the same method as described in Step 2 of Example 1, except that 4-(2-isopropoxyethoxy)benzaldehyde was replaced by the intermediate product obtained in the above (yield: 92%).

¹H NMR (300 MHz, DMSO-d6): δ 8.20 (s, 1H), 7.783 (s, 1H), 7.087 (d, J=8.7 Hz, 2H), 7.058 (s, 1H), 6.788 (d, J=8.7 Hz, 2H), 4.023 (t, J=14.7 Hz, 2H), 1.739 (t, J=14.7 Hz, 2H), 1.577 (m, 1H), 1.213-1.284 (m, 2H), 0.965-1.044 (m, 4H), 0.826-0.880 (m, 4H)

Example 10

Preparation of Derivative 10 According to the Present Invention

Derivative 10 having the following formula was prepared as follows.

[Formula of Derivative 10]

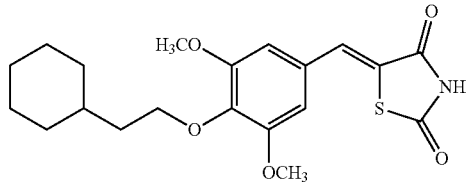

The intermediate product was prepared in accordance with the same method as described in Step 1 of Example 1, except that cyclohexylethanol and syringaldehyde were added in place of 2-isopropoxyethanol and p-hydroxybenzaldehyde, respectively (yield: 90%).

¹H NMR (300 MHz, CDCl3): 9.904 (s, 1H), 7.273 (s, 2H), 4.129 (t, J=13.2 Hz, 2H), 3.914 (s, 6H), 1.646 (t, J=13.2 Hz, 2H), 1.424-1.781 (m, 3H), 1.095-1.169 (m, 4H), 0.882-0.989 (m, 4H)

Then, Derivative 10 having the above formula, 5-(4-(2-cyclohexylethoxy)-3,5-dimethoxybenzylidene)thiazolidine-2,4-dione was obtained in accordance with the same method as described in Step 2 of Example 1, except that 4-(2-isopropoxyethoxy)benzaldehyde was replaced by the intermediate product obtained in the above (yield: 92%).

$^1$H NMR (300 MHz, DMSO-d6): δ 8.623 (s, 1H), 7.781 (s, 1H), 6.768 (s, 2H), 4.10 (t, J=13.5 Hz, 2H), 3.887 (s, 6H), 2.176 (s, 1H), 1.620 (t, J=13.5 Hz, 2H), 1.505-1.738 (m, 2H), 1.096-1.325 (m, 4H), 0.884-0.951 (m, 4H)

Example 11

Preparation of Derivative 11 According to the Present Invention

Derivative 11 having the following formula was prepared as follows.

[Formula of Derivative 11]

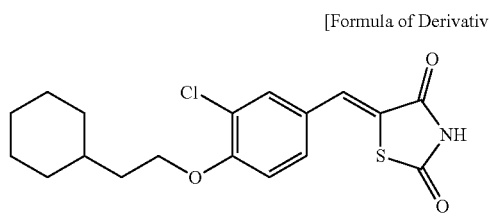

The intermediate product was prepared in accordance with the same method as described in Step 1 of Example 1, except that cyclohexylethanol and 3-chloro-4-hydroxybenzaldehyde were added in place of 2-isopropoxyethanol and p-hydroxybenzaldehyde, respectively (yield: 89%)

$^1$H NMR (300 MHz, CDCl3): δ 9.859 (s, 1H), 7.906 (s, 1H), 7.759 (d, J=8.4 Hz, 2H), 7.034 (d, J=8.4 Hz, 2H), 4.158 (t, J=13.5 Hz, 2H), 1.815 (t, J=13.5 Hz, 2H), 1.698-1.892 (m, 2H), 1.483-1.659 (m, 1H), 1.184-1.350 (m, 4H), 0.896-1.152 (m, 4H)

Then, Derivative 11 having the above formula, 5-(3-chloro-4-(2-cyclohexylethoxy)benzylidene)thiazolidine-2,4-dione, was obtained in accordance with the same method as described in Step 2 of Example 1, except that 4-(2-isopropoxyethoxy)benzaldehyde was replaced by the intermediate compound obtained in the above (yield: 90%).

$^1$H NMR (300 MHz, DMSO-d6): δ 8.19 (s, 1H), 7.738 (s, 1H), 7.522 (s, 1H), 7.386 (d, J=10.5 Hz, 1H), 7.012 (d, J=10.5 Hz, 1H), 4.155 (t, J=13.2 Hz, 2H), 1.800 (t, J=13.2 Hz, 2H), 1.657-1.800 (m, 4H), 1.500-1.606 (m, 1H), 1.151-1.335 (m, 4H), 0.854-1.052 (m, 2H)

Example 12

Preparation of Derivative 12 According to the Present Invention

Derivative 12 having the following formula was prepared as follows.

[Formula of Derivative 12]

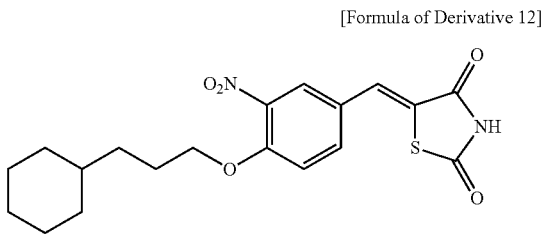 [SMILES: O=C1NC(=O)/C(=C/c2ccc(OCCCC3CCCCC3)c([N+](=O)[O-])c2)S1]

The intermediate product was prepared in accordance with the same method as described in Example 1, except that cyclohexylethanol and 3-chloro-4-hydroxybenzaldehyde were added in place of 2-isopropoxyethanol and p-hydroxybenzaldehyde, respectively (yield: 82%).

$^1$H NMR (300 MHz, CDCl3): δ 9.858 (s, 1H), 8.271 (s, 1H), 7.679 (d, J=8.7 Hz, 2H), 7.145 (d, J=8.7 Hz, 2H), 4.118 (t, J=13.2 Hz, 2H), 4.063 (d, J=6.9 Hz, 1H), 3.579 (t, J=13.8 Hz, 4H), 0.762-1.977 (m, 10H)

Then, Derivative 12 having the above formula, 5-(4-(3-cyclohexylpropoxy)-3-nitrobenzylidene)thiazolidine-2,4-dione, was obtained in accordance with the same method as described in Step 2 of Example 1, except that 4-(2-isopropoxyethoxy)benzaldehyde was replaced by the intermediate product obtained in the above (yield: 90%).

$^1$H NMR (300 MHz, DMSO-d6): δ 8.043 (s, 1H), 7.716 (s, 1H), 7.399 (d, J=11.1 Hz, 1H), 7.262 (s, 1H), 7.041 (d, J=11.1 Hz, 1H), 4.563 (dd, J=12.6, 1H), 4.048-4.087 (t, J=11.7 Hz, 2H), 4.029-4.179 (m, 1H), 1.631-1.889 (m, 8H), 1.159-1.389 (m, 2H), 1.236-1.284 (t, J=14.4 Hz, 2H), 0.840-0.961 (m, 2H)

Example 13

Preparation of Derivative 13 According to the Present Invention

Derivative 13 having the following formula was prepared as follows.

[Formula of Derivative 13]

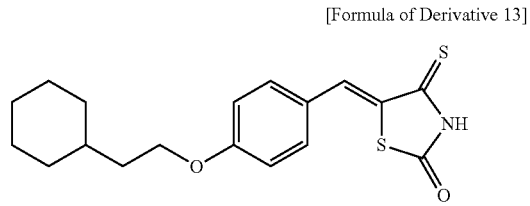 [SMILES: O=C1NC(=S)/C(=C/c2ccc(OCCC3CCCCC3)cc2)S1]

The intermediate, 4-(2-cyclohexylethoxy)benzaldehyde was prepared in accordance with the same method as described in Example 2, except that cyclohexylethanol was added in place of 4-(2-hydroxyethyl)morpholine (yield: 83%).

$^1$H NMR (300 MHz, CDCl3): δ 9.879 (s, 1H), 7.849 (d, J=13.8 Hz, 2H), 7.014 (d, J=13.8 Hz, 2H), 4.134 (t, J=13.2 Hz, 2H), 1.745 (t, J=13.2 Hz, 2H), 1.474-1.745 (m, 6H), 1.047-1.247 (m, 3H), 0.875-0.930 (m, 2H)

Then, Derivative 13 having the above formula, 5-(4-(2-cyclohexylethoxy)benzylidene)-4-thioxothiazolidin-2-one, was obtained in accordance with the same method as described in Step 2 of Example 1, except that 4-(2-isopropoxyethoxy)benzaldehyde and 2,4-thiazolidinedione were replaced by the intermediate product obtained in the above and rhodanine, respectively (yield: 82%).

$^1$H NMR (300 MHz, DMSO-d6): δ 7.758 (s, 1H), 7.499 (d, J=14.7 Hz, 2H), 6.970 (d, J=14.7 Hz, 2H), 4.036 (t, J=11.7 Hz, 2H), 3.575 (s, 1H), 1.704 (t, J=11.7 Hz, 2H), 1.565-1.756 (m, 5H), 1.434-1.528 (m, 1H), 1.103-1.260 (m, 3H), 0.907-1.029 (m, 2H)

Example 14

Preparation of Derivative 14 According to the Present Invention

Derivative 14 having the following formula was prepared as follows.

[Formula of Derivative 14]

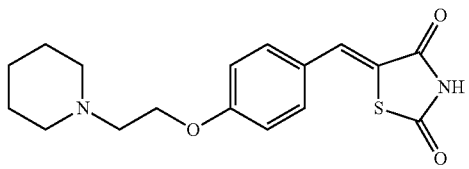

The intermediate, 4-(2-piperidin-1-yl)ethoxy)benzaldehyde, was prepared in accordance with the same method as described in Example 2, except that 1-piperidine ethanol was added in place of 4-(2-hydroxyethyl)morpholine (yield: 83%).

$^1$H NMR (300 MHz, CDCl3): δ 9.880 (s, 1H), 7.839 (d, J=8.7 Hz, 2H), 7.013 (d, J=8.7 Hz, 2H), 4.223 (t, J=11.7 Hz, 2H), 2.828 (t, J=11.7 Hz, 2H), 2.544 (t, J=10.5 Hz, 4H), 1.583-1.657 (m, 4H), 1.418-1.494 (m, 2H), 1.256-1.303 (m, 1H)

Then, Derivative 14 having the above formula, 5-(4-(2-(piperidin-1-yl)ethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 82%).

$^1$H NMR (300 MHz, DMSO-d6): δ 7.522 (s, 1H), 7.411 (d, J=10.2 Hz, 2H), 6.967 (d, J=10.2 Hz, 2H), 4.096 (t, J=11.1 Hz, 2H), 2.814 (t, J=11.1 Hz, 2H), 2.379 (m, 4H), 1.410-1.513 (m, 5H), 1.291-1.307 (m, 2H)

Example 15

Preparation of Derivative 15 According to the Present Invention

Derivative 15 having the following formula was prepared as follows.

[Formula of Derivative 15]

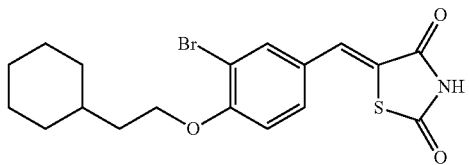 [SMILES: O=C1NC(=O)/C(=C/c2ccc(OCCC3CCCCC3)c(Cl)c2)S1]

The intermediate, 3-bromo-4-(2-cyclohexylethoxy)benzaldehyde, was prepared in accordance with the same method as described in Step 1 of Example 1, except that cyclohexylethanol and 3-bromo-4-hydroxybenzaldehyde were added in place of 2-isopropoxyethanol and p-hydroxybenzaldehyde, respectively (yield: 89%).

$^1$H NMR (300 MHz, CDCl3): δ 9.831 (s, 1H), 8.077 (s, 1H), 7.808 (d, J=8.4 Hz, 2H), 6.995 (d, J=8.4 Hz, 2H), 4.223 (t, J=14.4 Hz, 2H), 1.650-1.811 (m, 7H), 1.468-1.627 (m, 1H), 1.142-1.296 (m, 3H), 0.947-1.111 (m, 2H)

Then, Derivative 15 having the above formula, 5-(3-bromo-4-(2-cyclohexylethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).

$^1$H NMR (300 MHz, DMSO-d6): δ 12.576 (s, 1H), 7.841 (s, 1H), 7.833 (s, 1H), 7.570 (d, J=10.8 Hz, 1H), 7.284 (d, J=10.8 Hz, 1H), 4.174 (t, J=12.6 Hz, 2H), 1.617-1.750 (m, 7H), 1.460-1.529 (m, 1H), 1.062-1.265 (m, 3H), 0.896-0.966 (m, 2H)

Example 16

Preparation of Derivative 16 According to the Present Invention

Derivative 16 having the following formula was prepared as follows.

[Formula of Derivative 16]

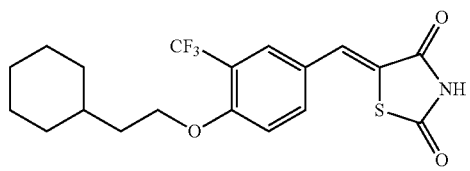 [SMILES: O=C1NC(=O)/C(=C/c2ccc(OCCC3CCCCC3)c(C(F)(F)F)c2)S1]

The intermediate, 4-(2-cyclohexylethoxy)-3-(trifluoromethyl)benzaldehyde, was prepared in accordance with the same method as described in Step 1 of Example 2, except that cyclohexylethanol and 4-fluoro-3-(trifluoromethyl)benzaldehyde were added in place of 4-(2-hydroxyethyl)morpholine and 4-fluorobenzaldehyde, respectively (yield: 89%).

$^1$H NMR (300 MHz, CDCl3): δ 9.915 (s, 1H), 8.102 (s, 1H), 8.044 (d, J=10.5 Hz, 2H), 7.125 (d, J=8.7 Hz, 2H), 4.208 (t, J=12.6 Hz, 2H), 1.639-1.788 (m, 6H), 1.466-1.567 (m, 1H), 1.177-1.338 (m, 4H), 0.882-1.041 (m, 2H)

Then, Derivative 16 having the above formula, 5-(4-(2-cyclohexylethoxy)-3-(trifluoromethyl)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 92%).

$^1$H NMR (300 MHz, DMSO-d6): δ 8.270 (s, 1H), 7.812 (s, 1H), 7.461 (d, J=8.7 Hz, 2H), 7.262 (s, 1H), 6.934 (d, J=8.7 Hz, 2H), 4.080 (t, J=13.5 Hz, 2H), 1.576-1.738 (m, 7H), 1.284-1.506 (m, 1H), 1.035-1.245 (m, 3H), 0.926-0.995 (m, 2H)

Example 17

Preparation of Derivative 17 According to the Present Invention

Derivative 17 having the following formula was prepared as follows.

[Formula of Derivative 17]

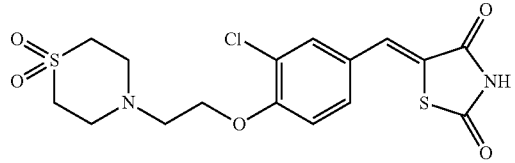 [SMILES: O=C1NC(=O)/C(=C/c2ccc(OCCN3CCS(=O)(=O)CC3)c(Cl)c2)S1]

The intermediate, 3-chloro-4-(2-thiomorpholine-1,1-dioxideethoxy)benzaldehyde, was prepared in accordance with the same method as described in Step 1 of Example 1, except that 4-(2-hydroxyethyl)thiomorpholine-1,1-dioxide and 3-chloro-4-hydroxybenzaldehyde were added in place of 2-isopropoxyethanol and p-hydroxybenzaldehyde, respectively (yield: 91%).

$^1$H NMR (300 MHz, CDCl3): δ 9.897 (s, 1H), 7.70 (s, 1H), 7.59 (d, J=9.0 Hz, 2H), 6.99 (d, J=9.0 Hz, 2H), 4.14 (t, J=10.5 Hz, 2H), 3.27 (dd, J=10.2, 10.2, 8H), 3.04 (t, J=10.5 Hz, 2H)

Then, Derivative 17 having the above formula, 5-[3-chloro-4-(2-thiomorpholine-1,1-dioxideethoxy)benzylidene]-thiazolidine-2,4-dione, was obtained in accordance with the same method as described in Step 2 of Example 1, except that 4-(2-isopropoxyethoxy)benzaldehyde was replaced by the intermediate obtained in the above (yield: 94%).

$^1$H NMR (300 MHz, DMSO-d6): δ 12.564 (s, 1H), 7.724 (s, 1H), 7.706 (s, 1H), 7.547 (d, J=11.1 Hz, 2H), 7.11 (d, J=9.0 Hz, 2H), 4.263 (t, J=10.5 Hz, 2H), 3.076 (s, 1H), 2.990 (t, J=10.5 Hz, 2H)

Example 18

Preparation of Derivative 18 According to the Present Invention

Derivative 18 having the following formula was prepared as follows.

[Formula of Derivative 18]

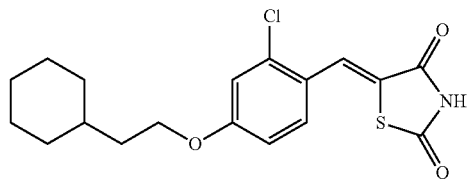 [SMILES: O=C1NC(=O)/C(=C/c2ccc(OCCC3CCCCC3)cc2Cl)S1]

The intermediate, 2-chloro-4-(2-cyclohexylethoxy)benzaldehyde, was prepared in accordance with the same method as described in Step 1 of Example 2, except that cyclohexylethanol and 2-chloro-4-fluorobenzaldehyde were added in place of 4-(2-hydroxymethyl)morpholine and 4-fluorobenzaldehyde, respectively (yield: 89%).

$^1$H NMR (300 MHz, CDCl3): δ 9.447 (s, 1H), 7.867 (d, J=8.4 Hz, 2H), 7.369 (s, 1H), 7.043 (d, J=8.4 Hz, 2H), 4.195 (t, J=13.2 Hz, 2H), 1.221-1.475 (m, 6H), 1.183-1.434 (m, 1H), 1.095-1.161 (m, 4H), 0.847-0.945 (m, 2H)

Then, Derivative 18 having the above formula, 5-(2-chloro-4-(2-cyclohexylethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).

$^1$H NMR (300 MHz, DMSO-d6): δ 12.654 (s, 1H), 7.877 (s, 1H), 7.517 (d, J=9 Hz, 1H), 7.110 (s, 1H), 7.012 (d, J=9 Hz, 1H), 4.111 (t, J=13.2 Hz, 2H), 1.434-1.642 (m, 4H), 1.263-1.434 (m, 1H), 1.094-1.221 (m, 4H), 0.847-0.989 (m, 2H)

Example 19

Preparation of Derivative 19 According to the Present Invention

Derivative 19 having the following formula was prepared as follows.

[Formula of Derivative 19]

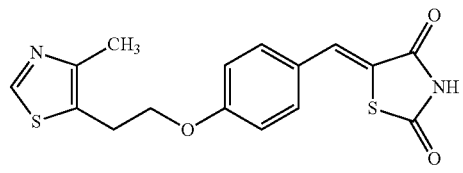 [SMILES: Cc1ncsc1CCOc1ccc(/C=C2\SC(=O)NC2=O)cc1]

The intermediate, 4-(2-(4-methylthiazol-2-yl)ethoxy)benzaldehyde, was prepared in accordance with the same method as described in Step 1 of Example 1, except that 5-(2-hydroxyethyl)-4-methylthiazole was added in place of 2-isopropoxyethanol (yield: 94%).

$^1$H NMR (300 MHz, CDCl3): δ 9.89 (s, 1H), 8.612 (s, 1H), 7.854 (d, J=10.2 Hz, 2H), 7.014 (d, J=10.2 Hz, 2H), 4.247 (t, J=11.7 Hz, 2H), 3.309 (t, J=11.7 Hz, 2H), 2.463 (s, 3H)

Then, Derivative 19 having the above formula, 5-(4-(2-(4-methylthiazol-5-yl)ethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 84%).

$^1$H NMR (300 MHz, DMSO-d6): δ 12.487 (s, 1H), 8.824 (s, 1H), 7.721 (s, 1H), 7.556 (d, J=8.7 Hz, 2H), 7.102 (d, J=8.7 Hz, 1H), 4.238 (t, J=12.3 Hz, 2H), 3.250 (t, J=12.3 Hz, 2H), 2.284 (s, 3H)

Example 20

Preparation of Derivative 20 According to the Present Invention

Derivative 20 having the following formula was prepared as follows.

[Formula of Derivative 20]

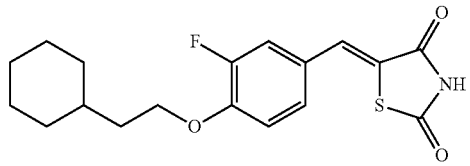 [SMILES: O=C1NC(=O)/C(=C/c2ccc(OCCC3CCCCC3)c(F)c2)S1]

The intermediate, 4-(2-cyclohexylethoxy)-3-fluorobenzaldehyde, was prepared in accordance with the same method as described in Example 2, except that cyclohexylethanol and 3,4-difluorobenzaldehyde were added in place of 4-(2-hydroxyethyl)morpholine and 4-fluorobenzaldehyde, respectively (yield: 85%).

$^1$H NMR (300 MHz, CDCl3): δ 9.857 (s, 1H), 7.583-7.633 (m, J=15 Hz, 2H), 7.087 (t, J=15.9 Hz, 1H), 4.178 (t, J=13.5 Hz, 2H), 1.697-1.798 (m, 6H), 1.217-1.290 (m, 5H), 0.969-1.007 (m, 2H)

Then, Derivative 20 having the above formula, 5-(4-(2-cyclohexylethoxy)-3-fluorobenzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).

¹H NMR (300 MHz, DMSO-d6): δ 12.183 (s, 1H), 7.610 (s, 1H), 7.239 (m, 3H), 4.158 (t, J=13.2 Hz, 2H), 1.605-1.143 (m, 6H), 1.445-1.605 (m, 1H), 1.096-1.265 (m, 4H), 0.917-0.991 (m, 2H)

Example 21

Preparation of Derivative 21 According to the Present Invention

Derivative 21 having the following formula was prepared as follows.

[Formula of Derivative 21]

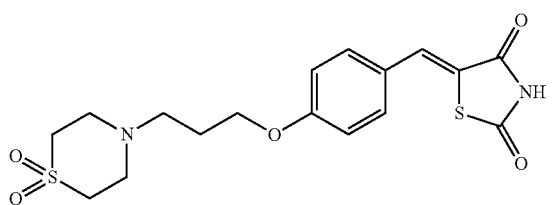 [SMILES: O=C1NC(=O)/C(=C/c2ccc(OCCCN3CCS(=O)(=O)CC3)cc2)S1]

The intermediate, 4-(3-thiomorpholine-1,1-dioxidepropoxy)benzaldehyde, was prepared in accordance with the same method as described in Step 1 of Example 1, except that 4-(3-hydroxypropyl)thiomorpholine-1,1-dioxide was added in place of 2-isopropoxyethanol (yield: 91%).

¹H NMR (300 MHz, CDCl3): δ 9.891 (s, 1H), 7.865 (d, J=11.4 Hz, 2H), 7.014 (d, J=11.4 Hz, 2H), 4.158 (t, J=12 Hz, 2H), 3.077 s, 8H), 2.749 (t, J=14.4, 2H), 1.953-2.047 (m, 2H)

Then, Derivative 21 having the above formula, 5-[4-(3-thiomorpholine-1,1-dioxidepropoxy)benzylidene]-thiazolidine-2,4-dione, was obtained in accordance with the same method as described in Step 2 of Example 1, except that 4-(2-isopropoxyethoxy)benzaldehyde was replaced by the intermediate obtained in the above (yield: 94%).

¹H NMR (300 MHz, DMSO-d6): δ 8.19 (s, 1H), 7.705 (s, 1H), 7.540 (d, J=8.1 Hz, 2H), 7.088 (d, J=8.1 Hz, 2H), 4.09 (t, J=12 Hz, 2H), 3.06 (m, 4H), 2.89 (m, 4H), 2.616 (t, J=14.1 Hz, 2H). 1.819-1.911 (m, 2H)

Example 22

Preparation of Derivative 22 According to the Present Invention

Derivative 22 having the following formula was prepared as follows.

[Formula of Derivative 22]

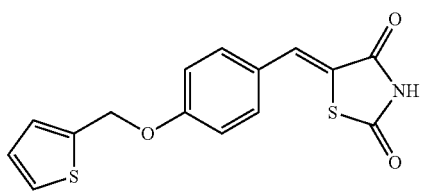 [SMILES: O=C1NC(=O)/C(=C/c2ccc(OCc3cccs3)cc2)S1]

The intermediate, 4-(thiophen-2-ylmethoxy)benzaldehyde, was prepared in accordance with the same method as described in Step 1 of Example 1, except that 2-thiophene methanol was added in place of 2-isopropoxyethanol (yield: 89%).

¹H NMR (300 MHz, CDCl3): δ 9.893 (s, 1H), 7.862 (d, J=8.4 Hz, 2H), 7.368 (d, J=5.1 Hz, 1H), 7.153 (d, J=3.3 Hz, 1H), 7.103 (d, J=8.4 Hz, 2H), 7.042 (t, J=8.4 Hz, 1H), 5.309 (s, 2H)

Then, Derivative 22 having the above formula, 5-(4-(thiophen-2-ylmethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 94%).

¹H NMR (300 MHz, DMSO-d6): δ 12.513 (s, 1H), 7.745 (s, 1H), 7.569 (d, J=8.4 Hz, 2H), 7.559 (t, J=2.4 Hz, 1H), 7.248 (t, J=3.3 Hz, 1H), 7.194 (d, J=8.4 Hz, 2H) 7.052 (m, J=10.5 Hz, 1H) 5.37 (s, 2H)

Example 23

Preparation of Derivative 23 According to the Present Invention

Derivative 23 having the following formula was prepared as follows.

[Formula of Derivative 23]

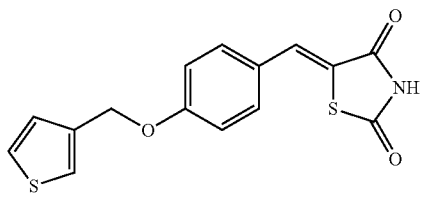 [SMILES: O=C1NC(=O)/C(=C/c2ccc(OCc3ccsc3)cc2)S1]

The intermediate, 4-(thiophene-3-ylmethoxy)benzaldehyde, was prepared in accordance with the same method as described in Step 1 of Example 1, except that 3-thiophene methanol was added in place of 2-isopropoxyethanol (yield: 94%).

¹H NMR (300 MHz, CDCl3): δ 9.926 (s, 1H), 7.865 (d, J=13.8 Hz, 2H), 7.350-7.405 (m, 2H), 7.164 (dd, J=1.5, 1.2 Hz, 1H), 5.160 (s, 2H)

Then, Derivative 23 having the above formula, 5-(4-(thiophen-3-ylmethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 89%).

¹H NMR (300 MHz, DMSO-d6): δ 12.504 (s, 1H), 8.590 (s, 1H), 7.864 (t, J=17.1 Hz, 1H) 7.733 (s, 1H), 7.573 (d, J=8.7 Hz, 2H), 7.521 (d, J=6 Hz, 1H), 7.373 (dd, J=5.7, 4.8, 1H), 7.197 (d, J=8.7 Hz, 2H), 5.252 (s, 2H)

Example 24

Preparation of Derivative 24 According to the Present Invention

Derivative 24 having the following formula was prepared as follows.

[Formula of Derivative 24]

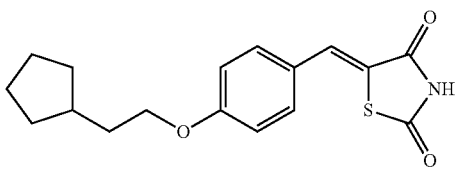 [SMILES: O=C1NC(=O)/C(=C/c2ccc(OCCC3CCCC3)cc2)S1]

The intermediate, 4-(2-cyclopentylethoxy)benzaldehyde, was prepared in accordance with the same method as described in Example 2, except that cyclopentylethanol was added in place of 4-(2-hydroxyethyl)morpholine (yield: 85%).

$^1$H NMR (300 MHz, CDCl3): δ 9.878 (s, 1H), 7.850 (d, J=11.4 Hz, 2H), 7.014 (d, J=11.4 Hz, 2H), 4.085 (t, J=13.5 Hz, 2H), 1.878-2.031 (m, 1H), 1.698-1.870 (m, 4H), 1.494-1.675 (m, 4H), 1.109-1.228 (m, 2H)

Then, Derivative 24 having the above formula, 5-(4-(2-cyclopentylethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).

$^1$H NMR (300 MHz, DMSO-d6): δ 12.502 (s, 1H), 7.737 (s, 1H), 7.550 (d, J=8.7 Hz, 2H), 7.093 (d, J=8.7 Hz, 2H), 4.136 (t, J=13.2 Hz, 2H), 2.06 (s, 2H), 1.807-1.976 (m, 1H), 1.700-1.769 (m, 4H), 1.455-1.611 (m, 4H), 1.102-1.185 (m, 2H)

Example 25

Preparation of Derivative 25 According to the Present Invention

Derivative 25 having the following formula was prepared as follows.

[Formula of Derivative 25]

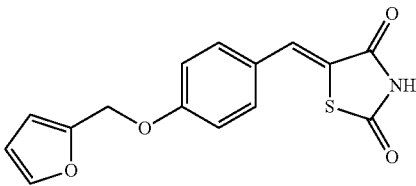 [SMILES: O=C1NC(=O)/C(=C/c2ccc(OCc3ccco3)cc2)S1]

The intermediate, 4-(furan-2-ylmethoxy)benzaldehyde, was prepared in accordance with the same method as described in Step 1 of Example 1, except that furfuryl alcohol was added in place of 2-isopropoxyethanol (yield: 94%).

$^1$H NMR (300 MHz, CDCl3): δ 9.895 (s, 1H), 7.872 (d, J=11.4 Hz, 2H), 7.473 (s, 1H), 7.118 (d, J=11.4 Hz, 2H), 6.483 (dd, J=3.3, 5.4 Hz, 2H), 5.093 (s, 2H)

Then, Derivative 25 having the above formula, 5-(4-(furan-2-ylmethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 89%).

$^1$H NMR (300 MHz, DMSO-d6): δ 12.518 (s, 1H), 7.747 (s, 1H), 7.705 (s, 1H), 7.572 (d, J=8.4 Hz, 1H), 7.200 (d, J=8.4 Hz, 2H), 6.630 (dd, J=3, 1.8, 1H), 5.142 (s, 2H)

Example 26

Preparation of Derivative 26 According to the Present Invention

Derivative 26 having the following formula was prepared as follows.

[Formula of Derivative 26]

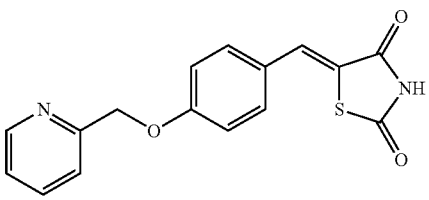 [SMILES: O=C1NC(=O)/C(=C/c2ccc(OCc3ccccn3)cc2)S1]

The intermediate, 4-(pyridine-2-ylmethoxy)benzaldehyde, was prepared in accordance with the same method as described in Step 1 of Example 1, except that 2-pyridine methanol was added in place of 2-isopropoxyethanol (yield: 94%).

$^1$H NMR (300 MHz, CDCl3): δ 9.932 (s, 1H), 8.630 (d, J=4.8 Hz, 1H), 7.870 (d, J=13.8 Hz, 2H), 7.767 (t, J=17.1 Hz, 1H), 7.513 (d, J=7.8 Hz, 1H), 7.284 (t, J=12.6 Hz, 1H), 7.129 (d, J=13.8 Hz, 2H), 5.295 (s, 2H)

Then, Derivative 26 having the above formula, 5-(4-(pyridin-2-ylmethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 89%).

$^1$H NMR (300 MHz, DMSO-d6): δ 12.525 (s, 1H), 8.585 (d, J=4.2 Hz, 1H), 7.865 (t, J=16.8 Hz, 1H), 7.735 (s, 1H), 7.575 (d, J=9 Hz, 2H), 7.527 (d, J=7.8 Hz, 1H), 7.372 (dd, J=4.8, 4.8, 1H), 7.197 (d, J=8.7 Hz, 2H), 5.251 (s, 2H)

Example 27

Preparation of Derivative 27 According to the Present Invention

Derivative 27 having the following formula was prepared as follows.

[Formula of Derivative 27]

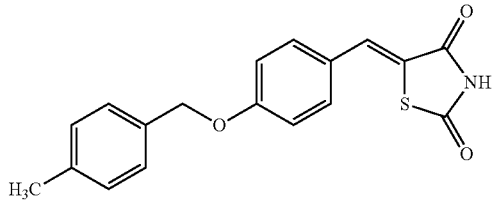 [SMILES: Cc1ccc(COc2ccc(/C=C3\SC(=O)NC3=O)cc2)cc1]

The intermediate, 4-(4-methylbenzyloxy)benzaldehyde, was prepared in accordance with the same method as described in Step 1 of Example 1, except that 4-methylbenzylalcohol was added in place of 2-isopropoxyethanol (yield: 94%).

$^1$H NMR (300 MHz, CDCl3): δ 9.885 (s, 1H), 7.891 (d, J=11.7 Hz, 2H), 7.335 (d, J=7.5 Hz, 2H), 7.261 (d, J=7.5 Hz, 2H), 7.095 (d, J=11.7 Hz, 2H), 5.11 (s, 2H), 2.371 (s, 3H)

Then, Derivative 27 having the above formula, 5-(4-(4-methylbenzyloxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 89%).

$^1$H NMR (300 MHz, DMSO-d6): δ 12.514 (s, 1H), 7.800 (s, 1H), 7.560 (d, J=8.7 Hz, 2H), 7.346 (d, J=7.8 Hz, 2H), 7.206 (d, J=8.1 Hz, 2H), 7.165 (d, J=9 Hz, 2H), 5.125 (s, 2H), 2.295 (s, 3H)

Example 28

Preparation of Derivative 28 According to the Present Invention

Derivative 28 having the following formula was prepared as follows.

[Formula of Derivative 28]

The intermediate, 4-(4-methoxybenzyloxy)benzaldehyde, was prepared in accordance with the same method as described in Step 1 of Example 1, except that 4-methoxybenzylalcohol was added in place of 2-isopropoxyethanol (yield: 94%).

$^1$H NMR (300 MHz, CDCl3): δ 9.889 (s, 1H), 7.854 (d, J=8.7 Hz, 2H), 7.378 (d, J=8.4 Hz, 2H), 7.087 (d, J=8.7 Hz, 2H), 7.095 (d, J=9 Hz, 2H), 5.077 (s, 2H), 3.826 (s, 3H)

Then, Derivative 28 having the above formula, 5-(4-(4-methoxybenzyloxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 89%).

$^1$H NMR (300 MHz, DMSO-d6): δ 12.523 (s, 1H), 7.897 (s, 1H), 7.470 (d, J=8.7 Hz, 2H), 7.249 (d, J=8.7 Hz, 2H), 7.307 (d, J=8.4 Hz, 2H), 7.165 (d, J=8.4 Hz, 2H), 5.055 (s, 2H), 3,785 (s, 3H)

Example 29

Preparation of Derivative 29 According to the Present Invention

Derivative 29 having the following formula was prepared as follows.

[Formula of Derivative 29]

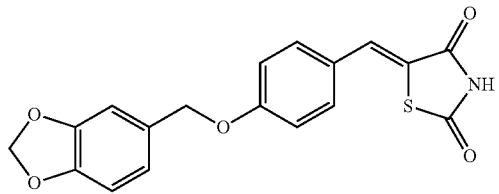 [SMILES: O=C1NC(=O)/C(=C/c2ccc(OCc3ccc4c(c3)OCO4)cc2)S1]

The intermediate, 5-(4-(benzo[d][1,3]dioxol-5-yl-methoxy)benzaldehyde, was prepared in accordance with the same method as described in Step 1 of Example 1, except that piperonylalcohol was added in place of 2-isopropoxyethanol (yield: 94%).

$^1$H NMR (300 MHz, CDCl3): δ 9.887 (s, 1H), 7.861 (d, J=13.2 Hz, 2H), 7.084 (d, J=13.2 Hz, 2H), 6.923 (dd, J=1.5, 1.5 Hz, 2H), 6.771 (s, 1H), 5.98 (s, 2H), 5.042 (s, 2H)

Then, Derivative 29 having the above formula, 5-(4-(benzo[d][1,3]dioxol-5-ylmethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 89%).

$^1$H NMR (300 MHz, DMSO-d6): δ 12.498 (s, 1H), 7.722 (s, 1H), 7.558 (d, J=9 Hz, 2H), 7.157 (d, J=8.7 Hz, 2H), 7.014 (s, 1H), 6.962 (dd, J=8.1, 8.1 Hz, 2H), 6.011 (s, 2H), 5.059 (s, 2H)

Example 30

Preparation of Derivative 30 According to the Present Invention

Derivative 30 having the following formula was prepared as follows.

[Formula of Derivative 30]

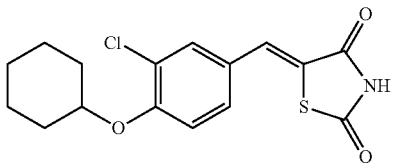 [SMILES: O=C1NC(=O)/C(=C/c2ccc(OC3CCCCC3)c(Cl)c2)S1]

The intermediate, 3-chloro-4-(cyclohexyloxy)benzaldehyde, was prepared in accordance with the same method as described in Example 1, except that cyclohexanol and 3-chloro-4-hydroxybenzaldehyde were added in place of 2-isopropoxyethanol and 4-hydroxybenzaldehyde, respectively (yield: 85%).

$^1$H NMR (300 MHz, CDCl3): δ 9.834 (s, 1H), 7.906 (d, J=3.9 Hz, 1H), 7.745 (dd, J=1.8, 2.1 Hz, 1H), 7.046 (d, J=8.4 Hz, 1H), 4.443-4.521 (m, 1H), 1.943-1.972 (m, 2H), 1.825-1.889 (m, 2H), 1.684-1.803 (m, 2H), 1.511-1.673 (m, 1H), 1.351-1.489 (m, 3H)

Then, Derivative 30 having the above formula, 5-(3-chloro-4-(cyclohexyloxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).

¹H NMR (300 MHz, DMSO-d6): δ 12.587 (s, 1H), 7.724 (s, 1H), 7.699 (d, J=2.1 Hz, 1H), 7.516 (dd, J=2.1, 2.4 Hz, 1H), 7.371 (d, J=8.7 Hz, 1H), 4.564-4.615 (m, 1H), 2.029-2.496 (m, 2H), 1.693-1.861 (m, 2H), 1.509-1.537 (m, 2H), 1.350-1.450 (m, 4H)

Example 31

Preparation of Derivative 31 According to the Present Invention

Derivative 31 having the following formula was prepared as follows.

[Formula of Derivative 31]

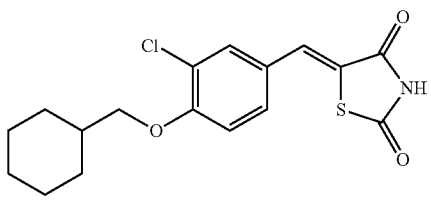 [SMILES: O=C1NC(=O)/C(=C/c2ccc(OCC3CCCCC3)c(Cl)c2)S1]

The intermediate, 3-chloro-4-(cyclohexylmethoxy)benzaldehyde, was prepared in accordance with the same method as described in Step 1 of Example 1, except that cyclohexylmethanol and 3-chloro-4-hydroxybenzaldehyde were added in place of 2-isopropoxyethanol and 4-hydroxybenzaldehyde, respectively (yield: 85%).
¹H NMR (300 MHz, CDCl3): δ 9.840 (s, 1H), 7.900 (d, J=2.1 Hz, 1H), 7.759 (dd, J=1.5, 2.4 Hz, 1H), 7.018 (d, J=8.4 Hz, 1H), 3.914 (d, J=5.7 Hz, 2H), 1.889-2.046 (m, 3H), 1.748-1.862 (m, 3H), 1.240-1.424 (m, 3H), 1.042-1.231 (m, 2H)

Then, Derivative 31 having the above formula, 5-(3-chloro-4-(cyclohexylmethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).
¹H NMR (300 MHz, DMSO-d6): δ 12.586 (s, 1H), 7.721 (s, 1H), 7.697 (d, J=2.4 Hz, 1H), 7.527 (dd, J=2.1, 2.4 Hz, 1H), 7.305 (d, J=8.7 Hz, 1H), 3.949 (d, J=6 Hz, 2H), 1.626-1.826 (m, 6H), 1.034-1.269 (m, 5H)

Example 32

Preparation of Derivative 32 According to the Present Invention

Derivative 32 having the following formula was prepared as follows.

[Formula of Derivative 32]

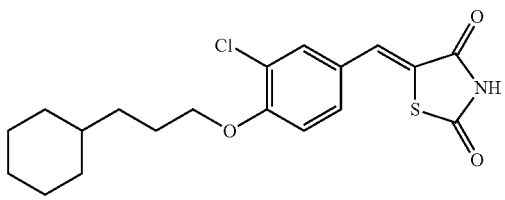 [SMILES: O=C1NC(=O)/C(=C/c2ccc(OCCCC3CCCCC3)c(Cl)c2)S1]

The intermediate, 3-chloro-4-(3-cyclohexylpropoxy)benzaldehyde, was prepared in accordance with the same method as described in Example 1, except that 3-cyclohexyl-1-propanol and 3-chloro-4-hydroxybenzaldehyde were added in place of 2-isopropoxyethanol and 4-hydroxybenzaldehyde, respectively (yield: 85%).
¹H NMR (300 MHz, CDCl3): δ 9.843 (s, 1H), 7.908 (d, J=1.8 Hz, 1H), 7.766 (d, J=10.5 Hz, 1H), 7.026 (d, J=8.4 Hz, 1H), 4.123 (t, J=13.2 Hz, 2H), 1.864-1.938 (m, 2H), 1.69-1.842 (m, 5H), 1.344-1.679 (m, 2H), 1.078-1.306 (m, 4H), 0.854-0.974 (m, 2H)

Then, Derivative 32 having the above formula, 5-(3-chloro-4-(3-cyclohexylpropoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).
¹H NMR (300 MHz, DMSO-d6): δ 12.587 (s, 1H), 7.717 (s, 1H), 7.695 (d, J=2.1 Hz, 1H), 7.531 (dd, J=2.4, 2.1 Hz, 1H), 7.302 (d, J=8.4 Hz, 1H), 4.125 (t, J=12.6 Hz, 2H), 1.625-1.772 (m, 7H), 1.079-1.348 (m, 6H), 0.837-0.911 (m, 2H)

Example 33

Preparation of Derivative 33 According to the Present Invention

Derivative 33 having the following formula was prepared as follows.

[Formula of Derivative 33]

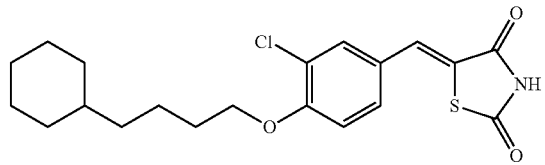 [SMILES: O=C1NC(=O)/C(=C/c2ccc(OCCCCC3CCCCC3)c(Cl)c2)S1]

The intermediate, 3-chloro-4-(4-cyclohexylbutoxy)benzaldehyde, was prepared in accordance with the same method as described in Example 1, except that 4-cyclohexyl-1-butanol and 3-chloro-4-hydroxybenzaldehyde were added in place of 2-isopropoxyethanol and 4-hydroxybenzaldehyde, respectively (yield: 85%).
¹H NMR (300 MHz, CDCl3): δ 9.842 (s, 1H), 7.905 (t, J=5.4 Hz, 1H), 7.764 (dd, J=1.8, 2.7 Hz, 1H), 7.029 (d, J=11.7 Hz, 1H), 4.136 (t, J=12.6 Hz, 2H), 1.830-1.903 (m, 2H), 1.679-1.809 (m, 6H), 1.461-1.675 (m, 2H), 1.112-1.294 (m, 7H), 0.859-0.93 (m, 2H)

Then, Derivative 33 having the above formula, 5-(3-chloro-4-(4-cyclohexylbutoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).
¹H NMR (300 MHz, DMSO-d6): δ 12.582 (s, 1H), 7.730 (s, 1H), 7.695 (d, J=2.1 Hz, 1H), 7.532 (dd, J=2.1, 2.1 Hz, 1H), 7.309 (d, J=9 Hz, 1H), 4.141 (t, J=12.3 Hz, 2H), 1.652-1.761 (m, 7H), 1.227-1.615 (m, 2H), 1.067-1.205 (m, 6H), 0.818-0.889 (m, 2H)

Example 34

Preparation of Derivative 34 According to the Present Invention

Derivative 34 having the following formula was prepared as follows.

[Formula of Derivative 34]

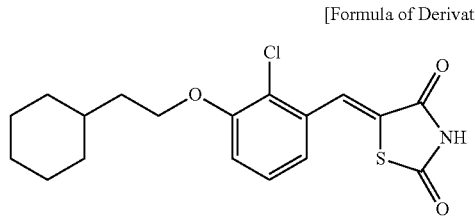

The intermediate product was prepared in accordance with the same method as described in Step 1 of Example 1, except that cyclohexylethanol and 2-chloro-3-hydroxybenzaldehyde were added in place of 2-isopropoxyethanol and 4-hydroxybenzaldehyde, respectively (yield: 85%).

$^1$H NMR (300 MHz, CDCl3): δ 10.532 (s, 1H), 7.582 (dd, J=2.7, 2.7 Hz, 1H), 7.205-7.339 (m, 1H), 7.162 (dd, J=1.5, 1.5 Hz, 1H), 4.125 (t, J=13.2 Hz, 2H), 1.645-1.804 (m, 6H), 1.389-1.593 (m, 1H), 1.118-1.339 (m, 4H), 0.854-1.055 (m, 2H)

Then, Derivative 34 having the above formula, 5-(2-chloro-3-(2-cyclohexylethoxy)benzylidene)thiazolidine-2,4-dione, was obtained in accordance with the same method as described in Step 2 of Example 1, except that 4-(2-isopropoxyethoxy)benzaldehyde was replaced by the intermediate product obtained in the above (yield: 90%).

$^1$H NMR (300 MHz, DMSO-d6): δ 12.582 (s, 1H), 7.908 (s, 1H), 7.462 (t, J=15.9 Hz, 1H), 7.283 (d, J=8.4 Hz, 1H), 7.150 (d, J=7.8 Hz, 1H), 4.140 (t, J=12.9 Hz, 2H), 1.642-1.758 (m, 7H), 1.493 (m, 1H), 1.161-1.228 (m, 3H), 0.933-0.969 (m, 2H)

Example 35

Preparation of Derivative 35 According to the Present Invention

Derivative 35 having the following formula was prepared as follows.

[Formula of Derivative 35]

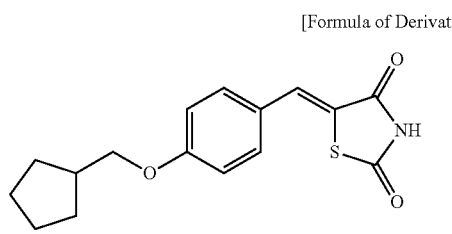

The intermediate, 4-(cyclopentylmethoxy)benzaldehyde, was prepared in accordance with the same method as described in Example 1, except that cyclopentylmethanol was added in place of 2-isopropoxyethanol (yield: 85%).

$^1$H NMR (300 MHz, CDCl3): δ 9.878 (s, 1H), 7.848 (d, J=11.4 Hz, 2H), 7.018 (d, J=11.4 Hz, 2H), 3.928 (d, J=7.2 Hz, 2H), 2.340-2.439 (m, 1H), 1.822-1.911 (m, 2H), 1.581-1.808 (m, 4H), 1.312-1.424 (m, 2H)

Then, Derivative 35 having the above formula, 5-(4-(cyclopentylmethoxy)benzylidene)thiazolidine-2,4-dione, was obtained in accordance with the same method as described in Step 2 of Example 1, except that 4-(2-isopropoxyethoxy)benzaldehyde was replaced by the intermediate product obtained in the above (yield: 90%).

$^1$H NMR (300 MHz, DMSO-d6): δ 12.503 (s, 1H), 7.732 (s, 1H), 7.547 (d, J=9 Hz, 2H), 7.094 (d, J=9 Hz, 2H), 3.922 (d, J=7.2 Hz, 2H), 2.253-2.351 (m, 1H), 1.750-1.770 (m, 2H), 1.525-1.603 (m, 4H), 1.283-1.344 (m, 2H)

Example 36

Preparation of Derivative 36 According to the Present Invention

Derivative 36 having the following formula was prepared as follows.

[Formula of Derivative 36]

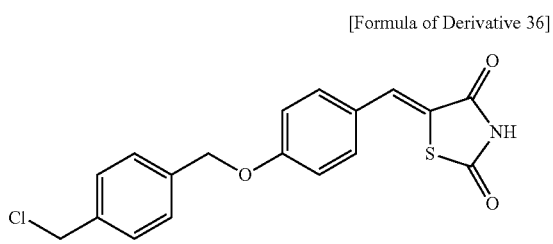

The intermediate, 4-(4-chloromethylbenzyloxy)benzaldehyde, was prepared in accordance with the same method as described in Step 1 of Example 1, except that 4-(chloromethyl)benzylalcohol was added in place of 2-isopropoxyethanol (yield: 94%).

$^1$H NMR (300 MHz, CDCl3): δ 9.932 (s, 1H), 7.87 (d, J=14.4 Hz, 2H), 7.433 (s, 4H), 7.096 (d, J=13.8 Hz, 2H), 5.157 (s, 2H), 4.605 (s, 2H)

Then, Derivative 36 having the above formula, 5-(4-(4-(chloromethyl)benzyloxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 89%).

$^1$H NMR (300 MHz, DMSO-d6): δ 12.549 (s, 1H), 7.748 (s, 1H), 7.58 (dd, J=3.3, 3.0 Hz, 4H), 7.454 (s, 2H) 7.190 (dd, J=3.9, 3.9 Hz, 2H), 5.219 (s, 2H), 4.760 (s, 2H)

Example 37

Preparation of Derivative 37 According to the Present Invention

Derivative 37 having the following formula was prepared as follows.

[Formula of Derivative 37]

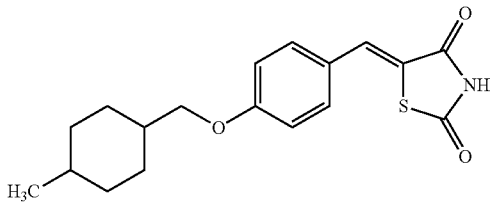

The intermediate, 4-(4-methylcyclohexylmethoxy)benzaldehyde, was prepared in accordance with the same method as described in Step 1 of Example 1, except that 4-methylcyclohexylmethanol was added in place of 2-isopropoxyethanol (yield: 94%).

$^1$H NMR (300 MHz, CDCl3): δ 9.371 (s, 1H), 7.378 (d, J=8.7 Hz, 2H), 6.66 (d, J=8.7 Hz, 2H), 3.531 (d, J=7.2 Hz, 1H), 3.419 (d, J=6.6 Hz, 1H), 1.19-1.499 (m, 3H), 0.943-1.047 (m, 4H), 0.64-0.821 (m, 2H), 0.375-0.596 (m, 4H)

Then, Derivative 37 having the above formula, 5-(4-((4-methylcyclohexyl)methoxy)benzylidene)thiazolidine-2,4-dione, was obtained in accordance with the same method as described in Step 2 of Example 1, except that 4-(2-isopropoxyethoxy)benzaldehyde was replaced by the intermediate product obtained in the above (yield: 89%).

$^1$H NMR (300 MHz, DMSO-d6): δ 12.493 (s, 1H), 7.693 (s, 1H), 7.536 (d, J=9.0 Hz, 2H), 7.101 (dd, J=6.9, 6.9 Hz, 2H), 3.963 (d, J=6.9 Hz, 1H), 3.851 (d, J=6.6 Hz, 1H), 1.662-1.976 (m, 4H), 1.185-1.516 (m, 4H), 0.975-1.161 (m, 2H), 0.852-0.935 (m, 3H)

Example 38

Preparation of Derivative 38 According to the Present Invention

Derivative 38 having the following formula was prepared as follows.

[Formula of Derivative 38]

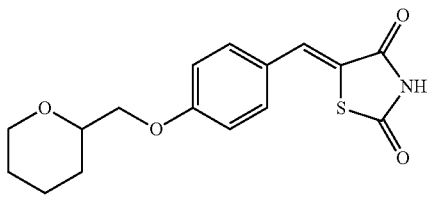 [SMILES: O=C1NC(=O)/C(=C/c2ccc(OCC3CCCCO3)cc2)S1]

The intermediate, 4-(2-(tetrahydro-2H-pyran-2-yl)methoxy)benzaldehyde, was prepared in accordance with the same method as described in Example 2, except that 2-(tetrahydro-2H-pyran-2-yl)methanol was added in place of 4-(2-hydroxyethyl)morpholine (yield: 90%).

$^1$H NMR (300 MHz, CDCl3): δ 9.881 (s, 1H), 7.839 (d, J=14.1 Hz, 2H), 7.044 (d, J=14.1 Hz, 2H), 4.034-4.087 (m, 2H), 3.943-3.990 (m, 1H), 3.703-3.780 (m, 1H), 3.481-3.566 (m, 1H), 1.908-1.948 (m, 1H), 1.451-1.692 (m, 5H)

Then, Derivative 38 having the above formula, 5-(4-(2-(tetrahydro-2H-pyran-2-yl)ethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 93%).

$^1$H NMR (300 MHz, DMSO-d6): δ 8.290 (s, 1H), 7.726 (s, 1H), 7.545 (d, J=9.0 Hz, 2H), 3.978 (d, J=5.1 Hz, 2H), 3.850-3.892 (m, 2H), 3.595-3.638 (m, 1H), 1.974-2.119 (m, 4H), 1.601-1.858 (m, 2H), 1.279-1.470 (m, 2H)

Example 39

Preparation of Derivative 39 According to the Present Invention

Derivative 39 having the following formula was prepared as follows.

[Formula of Derivative 39]

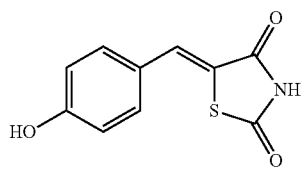

Derivative 39 having the above formula, 5-(4-hydroxybenzylidene)thiazolidine-2,4-dione, was obtained in accordance with the same method as described in Step 2 of Example 1, except that 4-(2-isopropoxyethoxy)benzaldehyde was replaced by 4-hydroxybenzaldehyde (yield: 94%).

$^1$H NMR (300 MHz, DMSO-d6): δ 12.411 (s, 1H), 10.313 (s, 1H), 7.971 (s, 1H), 7.459 (d, J=9.0 Hz, 2H), 6.914 (d, J=9.0 Hz, 2H)

Example 40

Preparation of Derivative 40 According to the Present Invention

Derivative 40 having the following formula was prepared as follows.

[Formula of Derivative 40]

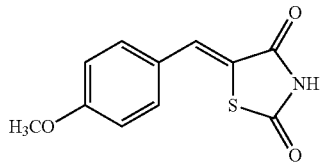 [SMILES: COc1ccc(/C=C2\SC(=O)NC2=O)cc1]

Derivative 40 having the above formula, 5-(4-methoxybenzylidene)thiazolidine-2,4-dione, was obtained in accordance with the same method as described in Step 2 of Example 1, except that 4-(2-isopropoxyethoxy)benzaldehyde was replaced by 4-methoxybenzaldehyde (yield: 86%).

$^1$H NMR (300 MHz, DMSO-d6): δ 12.411 (s, 1H), 10.313 (s, 1H), 7.971 (s, 1H), 7.459 (d, J=9.0 Hz, 2H), 6.914 (d, J=9.0 Hz, 2H)

Example 41

Preparation of Derivative 41 According to the Present Invention

Derivative 41 having the following formula was prepared as follows.

[Formula of Derivative 41]

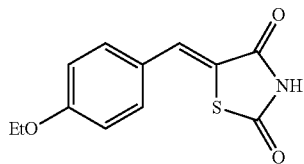 [SMILES: CCOc1ccc(/C=C2\SC(=O)NC2=O)cc1]

Derivative 41 having the above formula, 5-(4-ethoxybenzylidene)thiazolidine-2,4-dione, was obtained in accordance with the same method as described in Step 2 of Example 1, except that 4-(2-isopropoxyethoxy)benzaldehyde was replaced by 4-ethoxybenzaldehyde (yield: 91%).

Example 42

Preparation of Derivative 42 According to the Present Invention

Derivative 42 having the following formula was prepared as follows.

[Formula of Derivative 42]

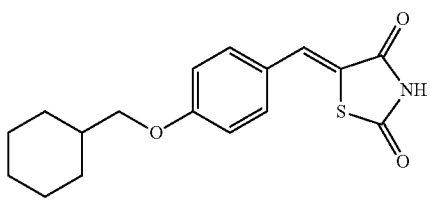 [SMILES: O=C1NC(=O)/C(=C/c2ccc(OCC3CCCCC3)cc2)S1]

The intermediate, 4-(cyclohexylmethoxy)benzaldehyde, was prepared in accordance with the same method as described in Example 2, except that cyclohexylmethanol was added in place of 4-(2-hydroxyethyl)morpholine (yield: 79%).

Then, Derivative 42 having the above formula, 5-(4-(cyclohexylmethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 90%).

$^1$H NMR (300 MHz, DMSO-d6): δ 8.345 (s, 1H), 7.748 (s, 1H), 7.390 (d, J=11.7 Hz, 2H), 6.895 (d, J=11.7 Hz, 2H), 3.752 (d, J=6.0 Hz, 2H), 1.629-1.819 (m, 6H). 1.152-1.301 (m, 3H), 0.926-1.072 (m, 2H)

Example 43

Preparation of Derivative 43 According to the Present Invention

Derivative 43 having the following formula was prepared as follows.

[Formula of Derivative 43]

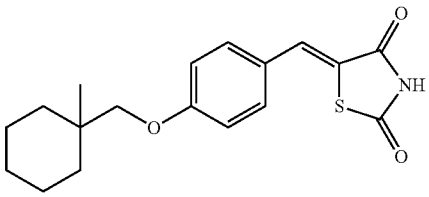 [SMILES: CC1(COc2ccc(/C=C3\SC(=O)NC3=O)cc2)CCCCC1]

The intermediate, 4-(1-methylcyclohexylmethoxy)benzaldehyde, was prepared in accordance with the same method as described in Example 2, except that 1-methylcyclohexylmethanol was added in place of 4-(2-hydroxyethyl)morpholine (yield: 80%).

Then, Derivative 43 having the above formula, 5-(4-((1-methylcyclohexyl)methoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 91%).

$^1$H NMR (300 MHz, DMSO-d6): δ 12.487 (s, 1H), 7.722 (s, 1H), 7.545 (d, J=8.7 Hz, 2H), 7.108 (d, J=8.7 Hz, 2H), 3.754 (s, 2H), 1.139-1.453 (m, 7H), 1.310-1.337 (m, 3H), 0.985 (s, 3H)

Example 44

Preparation of Derivative 44 According to the Present Invention

Derivative 44 having the following formula was prepared as follows.

[Formula of Derivative 44]

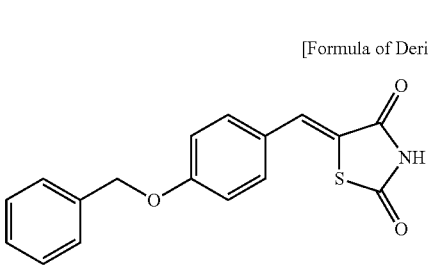

The intermediate, 4-(benzyloxy)benzaldehyde, was prepared in accordance with the same method as described in Example 2, except that benzylalcohol was added in place of 4-(2-hydroxyethyl)morpholine (yield: 92%).

Then, Derivative 44 having the above formula, 5-(4-(benzyloxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 78%).

$^1$H NMR (300 MHz, DMSO-d6): δ 12.498 (s, 1H), 7.736 (s, 1H), 7.566 (d, J=8.7 Hz, 2H), 7.306-7.468 (m, 5H), 7.18 (d, J=8.7 Hz, 2H), 5.176 (s, 2H)

Example 45

Preparation of Derivative 45 According to the Present Invention

Derivative 45 having the following formula was prepared as follows.

[Formula of Derivative 45]

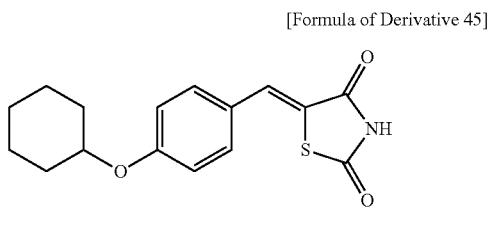

The intermediate, 4-(cyclohexyloxy)benzaldehyde, was prepared in accordance with the same method as described in Example 2, except that cyclohexanol was added in place of 4-(2-hydroxyethyl)morpholine (yield: 94%).

Then, Derivative 45 having the above formula, 5-(4-(cyclohexyloxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 88%).

$^1$H NMR (300 MHz, DMSO-d6): δ 12.496 (s, 1H), 7.724 (s, 1H), 7.532 (d, J=8.7 Hz, 2H), 7.091 (d, J=8.7 Hz, 2H), 4.455 (q, 1H), 1.865-2.073 (m, 2H), 1.675-1.865 (m, 2H), 1.446-1.547 (m, 3H), 1.257-1.415 (m, 3H), 1.160-1.257 (m, 1H)

Example 46

Preparation of Derivative 46 According to the Present Invention

Derivative 46 having the following formula was prepared as follows.

[Formula of Derivative 46]

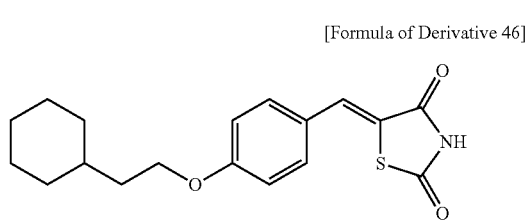

The intermediate, 4-(cyclohexylethyloxy)benzaldehyde, was prepared in accordance with the same method as described in Example 2, except that cyclohexylethanol was added in place of 4-(2-hydroxyethyl)morpholine (yield: 89%).

Then, Derivative 46 having the above formula, 5-(4-(2-cyclohexylethoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 81%).

$^1$H NMR (300 MHz, DMSO-d6): δ 8.195 (s, 1H), 7.675 (s, 1H), 7.473 (d, J=14.7 Hz, 2H), 6.895 (d, J=14.7 Hz, 2H), 4.036 (t, J=11.7 Hz, 2H), 1.565-1.727 (m, 5H), 1.437-1.469 (m, 1H), 1.041-1.223 (m, 3H), 0.807-1.034 (m, 2H)

Example 47

Preparation of Derivative 47 According to the Present Invention

Derivative 47 having the following formula was prepared as follows.

[Formula of Derivative 47]

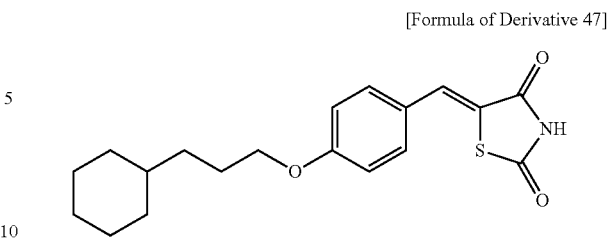

The intermediate, 4-(3-cyclohexylpropoxy)benzaldehyde, was prepared in accordance with the same method as described in Step 1 of Example 1, except that 3-cyclohexyl-1-propanol was added in place of 4-(2-hydroxyethyl)morpholine (yield: 88%).

Then, Derivative 47 having the above formula, 5-(4-(3-cyclohexylpropoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 80%).

$^1$H NMR (300 MHz, DMSO-d6): δ 12.505 (s, 1H), 7.730 (s, 1H), 7.547 (d, J=9.0 Hz, 2H), 7.084 (d, J=9.0 Hz, 2H), 4.028 (t, J=12.9 Hz, 2H), 1.628-1.711 (m, 7H), 1.143-1.300 (m, 6H), 0.839-0.911 (m, 2H)

Example 48

Preparation of Derivative 48 According to the Present Invention

Derivative 48 having the following formula was prepared as follows.

[Formula of Derivative 48]

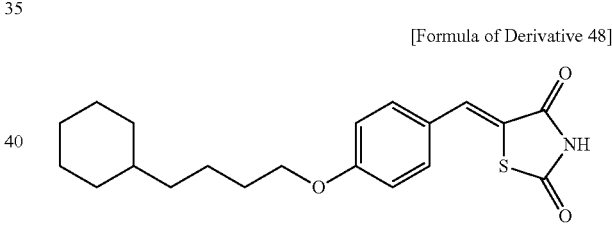

The intermediate, 4-(4-cyclohexylbutoxy)benzaldehyde, was prepared in accordance with the same method as described in Example 2, except that 4-cyclohexyl-1-butanol was added in place of 4-(2-hydroxyethyl)morpholine (yield: 92%).

Then, Derivative 48 having the above formula, 5-(4-(4-cyclohexylbutoxy)benzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 87%).

$^1$H NMR (300 MHz, DMSO-d6): δ 12.453 (s, 1H), 7.407 (s, 1H), 7.357 (d, J=8.7 Hz, 2H), 6.933 (d, J=8.7 Hz, 2H), 4.003 (t, J=12.3 Hz, 2H), 1.625-1.692 (m, 6H), 1.37-1.1.398 (m, 3H), 1.133-1.215 (m, 4H), 0.815-0.956 (m, 4H)

Example 49

Preparation of Derivative 49 According to the Present Invention

Derivative 49 having the following formula was prepared as follows.

[Formula of Derivative 49]

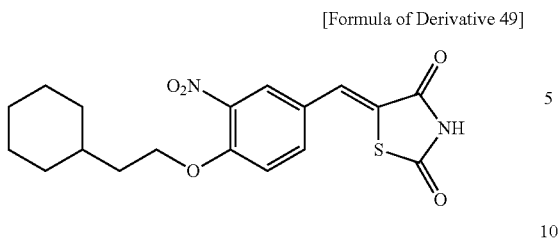

The intermediate, 4-(2-cyclohexylethoxy)-3-nitrobenzaldehyde, was prepared in accordance with the same method as described in Example 2, except that 4-cyclohexylethanol and 4-hydroxy-3-nitrobenzaldehyde were added in place of 4-(2-hydroxyethyl)morpholine and 4-hydroxybenzaldehyde, respectively (yield: 94%).

Then, Derivative 49 having the above formula, 5-(4-(2-cyclohexylethoxy)-3-nitrobenzylidene)thiazolidine-2,4-dione, was obtained in accordance with the same method as described in Step 2 of Example 1, except that 4-(2-isopropoxyethoxy)benzaldehyde was replaced by the intermediate obtained in the above (yield: 85%).

$^1$H NMR (300 MHz, CDCl3): δ 9.931 (s, 1H), 8.345 (s, 1H), 8.081 (d, J=10.2 Hz, 1H), 7.267 (d, J=10.2 Hz, 1H), 4.190 (t, J=12.9 Hz, 2H), 1.839-1.934 (m, 2H), 1.644-1.754 (m, 4H), 1.335-1.408 (m, 2H), 1.086-1.262 (m, 3H), 0.864-0.970 (m, 2H)

Example 50

Preparation of Derivative 50 According to the Present Invention

Derivative 50 having the following formula was prepared as follows.

[Formula of Derivative 50]

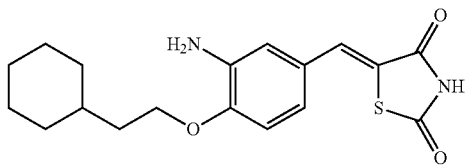 [SMILES: Nc1cc(/C=C2\SC(=O)NC2=O)ccc1OCCC1CCCCC1]

Fe (1.49 g, 27 mmol) and FeSO$_4$ (0.75 g, 2.7 mmol) were mixed with 50 ml of methanol-distilled water (9:1) solution containing Derivative 48 (1 g, 2.7 mmol) and then reacted for 7 hours under reflux. The reaction product was filtered, and the precipitate was washed with hot methanol and then mixed with the filtrate. The concentrated filtrate was purified by silica gel column chromatography (hexane:ethylacetate=10:1) to afford Derivative 50 having the above formula, 5-(3-amino-4-(2-cyclohexylethoxy)benzylidene)thiazolidine-2,4-dione (0.85 g, yield: 92%).

Example 51

Preparation of Derivative 51 According to the Present Invention

Derivative 51 having the following formula was prepared as follows.

[Formula of Derivative 51]

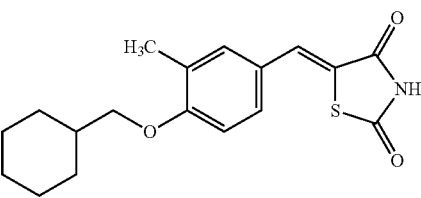 [SMILES: Cc1cc(/C=C2\SC(=O)NC2=O)ccc1OCC1CCCCC1]

Step 1: To the solution in which cyclohexanemethanol (1 g, 8.8 mmol), 4-hydroxy-3-methylbenzaldehyde (1.20 g, 8.8 mmol) and triphenylphosphine in THF (20 ml) (2.54 g, 9.7 mmol) were mixed, diethyl azodicarboxylate (40% in toluene, 9.7 mmol) was added at 0° C. over 10 minutes while stirring. Then, the mixture was stirred at room temperature until the initial reaction product of cyclohexanemethanol and 4-hydroxy-3-methylbenzaldehyde disappeared. The resulting solution was concentrated under reduced pressure and purified by silica gel chromatography (hexane:ethyl acetate=10:1) to afford 4-(2-cyclomethoxy)-3-methylbenzaldehyde as yellow oil (1.69 g, yield: 83%)

Step 2: 4-(2-cyclomethoxy)-3-methylbenzaldehyde obtained in Step 1 above (1 g, 4.3 mmol) and 2,4-thiazolidinedione (504 mg, 4.3 mmol) were dissolved in 20 ml of toluene. After subsequently adding piperidine (0.21 ml, 2.15 mmol) and acetic acid (0.12 ml, 2.15 mmol) thereto, the mixture was heated overnight under reflux in a Dean-Stark water trap. Then, the resulting mixture was cooled and filtered. The precipitate was washed with hexane and dried to afford Derivative 51 having the above formula, 5-(4-(2-cyclohexylmethoxy)-3-methylbenzylidene)thiazolidine-2,4-dione as yellow solid (1.10 g, yield: 77.5%).

$^1$H NMR (300 MHz, DMSO-d6) δ 7.784 (s, 1H), 7.345 (d, J=8.4 Hz, 2H), 7.289 (s, 1H), 6.912 (d, J=8.4 Hz, 2H), 4.074 (d, J=5.7 Hz, 2H), 2.302 (s, 3H), 1.706-1.894 (m, 6H), 1.257-1.380 (m, 3H), 1.070-1.225 (m, 2H)

Example 52

Preparation of Derivative 52 According to the Present Invention

Derivative 52 having the following formula was prepared as follows.

[Formula of Derivative 52]

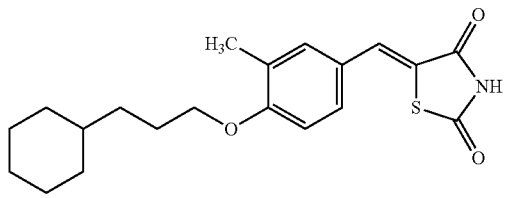 [SMILES: Cc1cc(/C=C2\SC(=O)NC2=O)ccc1OCCCC1CCCCC1]

The intermediate product, 4-(2-cyclohexylpropoxy)-3-methylbenzaldehyde, was prepared in accordance with the same method as described in Example 51, except that 3-cyclohexyl-1-propanol (1 g, 7.0 mmol) and 3-chloro-4-hydroxybenzaldehyde (0.95 g, 7.0 mmol) were added in place of cyclohexanemethanol and 4-hydroxy-3-methylbenzaldehyde, respectively (1.46 g, yield: 80%).

Then, Derivative 52 having the above formula, 5-(4-(2-cyclohexylpropoxy)-3-methylbenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.23 g, yield: 89.1%).

¹H NMR (300 MHz, DMSO-d6) δ 7.793 (s, 1H), 7.349 (d, J=8.4 Hz, 2H), 7.312 (s, 1H), 6.898 (d, J=8.4 Hz, 2H), 4.029 (t, J=13.2 Hz, 2H), 1.650-2.041 (m, 8H), 1.089-1.397 (m, 4H), 0.860-0.968 (m, 3H)

Example 53

Preparation of Derivative 53 According to the Present Invention

Derivative 53 having the following formula was prepared as follows.

[Formula of Derivative 53]

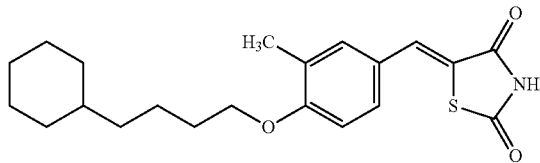 [SMILES: Cc1cc(/C=C2\SC(=O)NC2=O)ccc1OCCCCC1CCCCC1]

The intermediate, 4-(2-cyclohexylbutoxy)-3-methylbenzaldehyde, was prepared in accordance with the same method as described in Example 51, except that 4-cyclohexyl-1-butanol (1 g, 6.4 mmol) was added in place of cyclohexanemethanol and 0.87 g of 4-hydroxy-3-methylbenzaldehyde (6.4 mmol) was used (1.43 g, yield: 81%).

Then, Derivative 53 having the above formula, 5-(4-(2-cyclohexylbutoxy)-3-methylbenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.19 g, yield: 87.5%).

¹H NMR (300 MHz, DMSO-d6) δ 7.787 (s, 1H), 7.421 (d, J=8.7 Hz, 2H), 7.291 (s, 1H), 6.903 (d, J=8.7 Hz, 2H), 4.045 (t, J=12.9 Hz, 2H), 1.806-1.852 (m, 2H), 1.694-1.779 (m, 5H), 1.438-1.510 (m, 2H), 1.174-1.266 (m, 6H), 0.857-0.890 (m, 2H)

Example 54

Preparation of Derivative 54 According to the Present Invention

Derivative 54 having the following formula was prepared as follows.

[Formula of Derivative 54]

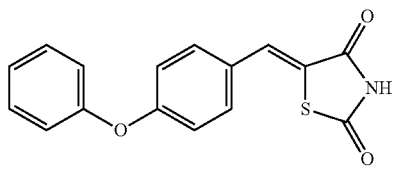 [SMILES: O=C1NC(=O)/C(=C/c2ccc(Oc3ccccc3)cc2)S1]

The intermediate product, 4-phenoxybenzaldehyde, was prepared in accordance with the same method as described in Example 51, except that phenol (1 g, 10.6 mmol) and 4-hydroxybenzaldehyde (1.29 g, 10.6 mmol) were used in place of cyclohexanemethanol and 4-hydroxy-3-methylbenzaldehyde, respectively, and 3.06 g of triphenylphosphin (11.66 mmol) was used (1.2 g, yield: 57%).

Then, Derivative 54 having the above formula, 5-(4-phenoxybenzylidene)-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.02 g, yield: 72.0%).

¹H NMR (300 MHz, DMSO-d6) δ 8.302 (s, 1H), 7.536-7.639 (m, 5H), 7.349 (d, J=8.4 Hz, 2H), 6.903 (d, J=8.4 Hz, 2H)

Example 55

Preparation of Derivative 55 According to the Present Invention

Derivative 55 having the following formula was prepared as follows.

[Formula of Derivative 55]

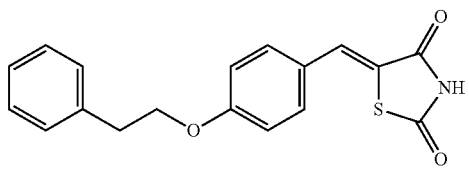 [SMILES: O=C1NC(=O)/C(=C/c2ccc(OCCc3ccccc3)cc2)S1]

The intermediate product, 4-(2-phenylethoxy)benzaldehyde, was prepared in accordance with the same method as described in Example 51, except that 2-phenylethanol (1 g, 8.2 mmol) and 4-hydroxybenzaldehyde (1.0 g, 8.2 mmol) were used in place of cyclohexanemethanol and 4-hydroxy-3-methylbenzaldehyde, respectively, and 2.37 g of triphenylphosphine (9.02 mmol) was used (1.5 g, yield: 79%).

Then, Derivative 55 having the above formula, 5-[4-(2-phenylethoxy)benzylidene]-1,3-thiazolidine-2,4-dione, was obtained in accordance with the same method as described in Step of Example 51, except that 4-(2-cyclomethoxy)-3-methylbenzaldehyde was replaced by the intermediate obtained in the above (0.94 g, yield: 62.7%).

¹H NMR (300 MHz, DMSO-d6) δ 7.806 (s, 1H), 7.466 (d, J=8.7 Hz, 2H), 7.262-7.369 (m, 5H), 7.196 (d, J=8.7 Hz, 2H), 4.261 (t, J=14.1 Hz, 2H), 3.153 (t, J=14.1 Hz, 2H)

Example 56

Preparation of Derivative 56 According to the Present Invention

Derivative 56 having the following formula was prepared as follows.

[Formula of Derivative 56]

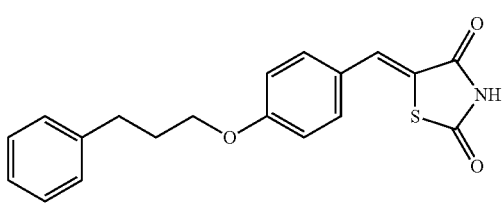 [SMILES: O=C1NC(=O)/C(=C/c2ccc(OCCCc3ccccc3)cc2)S1]

The intermediate, 4-(3-phenylpropoxy)benzaldehyde, was prepared in accordance with the same method as described in Example 51, except that 3-phenyl-1-propanol (1 g, 7.3 mmol) and 4-hydroxybenzaldehyde (0.89 g, 7.3 mmol) were added in place of cyclohexanemethanol and 4-hydroxy-3-methylbenzaldehyde, and 2.11 g of triphenylphosphine (8.03 mmol) was used (1.52 g, 86.4%).

Then, Derivative 56 having the above formula, 5-[4-(2-phenylpropoxy)benzylidene]-1,3-thiazolidine-2,4-dione, was obtained in accordance with the same method as described in Step of Example 51, except that 4-(2-cyclomethoxy)-3-methylbenzaldehyde was replaced by the intermediate obtained in the above (1.12 g, yield: 80.1%).

1H NMR (300 MHz, DMSO-d6) δ 7.820 (s, 1H), 7.465 (d, J=8.7 Hz, 2H), 7.201-7.329 (m, 5H), 6.993 (d, J=8.7 Hz, 2H), 4.020 (t, J=12.3 Hz, 2H), 2.851 (t, J=15.0 Hz, 2H), 2.094-2.187 (m, 2H)

Example 57

Preparation of Derivative 57 According to the Present Invention

Derivative 57 having the following formula was prepared as follows.

[Formula of Derivative 57]

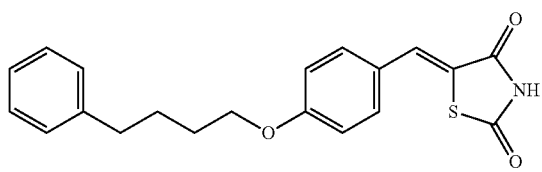 [SMILES: O=C1NC(=O)/C(=C/c2ccc(OCCCCc3ccccc3)cc2)S1]

The intermediate product, 4-(3-phenylbutoxy)benzaldehyde, was prepared in accordance with the same method as described in Example 51, except that 4-phenyl-1-butanol (1 g, 6.7 mmol) and 4-hydroxybenzaldehyde (0.82 g, 6.7 mmol) were added in place of cyclohexanemethanol and 4-hydroxy-3-methylbenzaldehyde, and 1.93 of triphenylphosphine (7.37 mmol) was used (1.42 g, yield: 84%).

Then, Derivative 57 having the above formula, 5-[4-(2-phenylbutoxy)benzylidene]-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.15 g, yield: 85%).

¹H NMR (300 MHz, DMSO-d6) δ 7.816 (s, 1H), 7.468 (d, J=8.7 Hz, 2H), 7.174-7.323 (m, 5H), 6.903 (d, J=8.7 Hz, 2H), 4.048 (t, J=11.7 Hz, 2H), 2.724 (t, J=13.8 Hz, 2H), 1.786-1.876 (m, 4H)

Example 58

Preparation of Derivative 58 According to the Present Invention

Derivative 58 having the following formula was prepared as follows.

[Formula of Derivative 58]

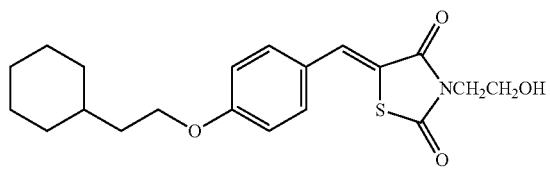

Sodium hydride (24.14 mg, 1.0 mmol, 60% dispersed oil) was added in 20 ml of DMF solution containing 5-4-(2-cyclohexylethoxy)benzylidene)thiazolidin-2,4-dione (200 mg, 0.60 mmol) and stirred at room temperature under nitrogen. The mixture was further stirred for 10 minutes, and 2-iodoethanol (123.81 mg, 0.72 mmol) dissolved in 5 ml of DMF was slowly added thereto. After being stirred at 60° C. for 48 hours, the reaction mixture was extracted with ethyl acetate and washed with water. The organic layer was dried with anhydrous magnesium sulfate, filtered and solvent-evaporated. The residue was purified by silica gel chromatography (hexane:ethyl acetate=10:1) to afford Derivative 58 having the above formula, 5-[(4-(2-cyclohexylethoxy)benzylidene]-3-(hydroxyethyl)-1,3-thiazolidine-2,4-dione (180 mg, yield: 79%).

¹H NMR (300 MHz, CDCl3) δ 7.878 (s, 1H), 7.485 (d, J=14.4 Hz, 2H), 7.007 (d, J=14.4 Hz, 2H), 4.078 (t, J=13.2 Hz, 2H), 4.001 (t, J=10.2 Hz, 2H), 3.891 (t, J=10.2 Hz, 2H), 2.049 (m, 1H), 1.670-1.782 (m, 7H), 1.471-1.529 (m, 1H), 1.178-1.284 (m, 3H), 0.956-1.034 (m, 2H)

Example 59

Preparation of Derivative 59 According to the Present Invention

Derivative 59 having the following formula was prepared as follows.

[Formula of Derivative 59]

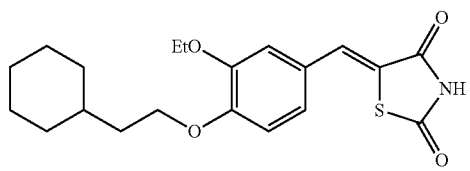

The intermediate product, 4-(2-cyclohexylethoxy)-3-ethoxybenzaldehyde, was prepared in accordance with the same method as described in Example 51, except that cyclohexanethanol (1 g, 7.8 mmol) and 3-ethoxy-4-hydroxyaldehyde (1.30 g, 7.8 mmol) were added in place of cyclohexanemethanol and 4-hydroxy-3-methylbenzaldehyde, and 2.25 g of triphenylphosphine (8.58 mmol) was used (1.85 g, yield: 85.7%).

Then, Derivative 59 having the above formula, 5-(4-(2-cyclohexylethoxy)-3-ethoxybenzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.12 g, yield: 83.0%).

$^1$H NMR (300 MHz, DMSO-d6) δ 12.582 (s, 1H), 7.786 (s, 1H), 7.116 (d, J=10.8 Hz, 1H), 6.959 (d, J=10.8 Hz, 1H), 7.000 (s, 1H), 4.089 (m, 4H), 1.653-1.795 (m, 7H), 1.459-1.577 (m, 4H), 1.146-1.282 (m, 3H), 0.941-1.05 (m, 2H)

Example 60

Preparation of Derivative 60 According to the Present Invention

Derivative 60 having the following formula was prepared as follows.

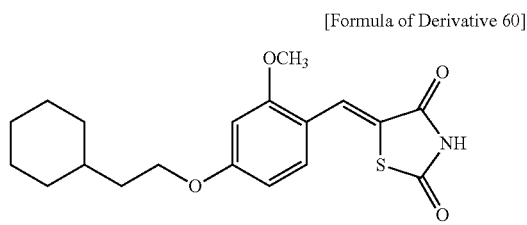

[Formula of Derivative 60]

The intermediate product, 4-(2-cyclohexylethoxy)-2-methoxybenzaldehyde, was prepared in accordance with the same method as described in Example 51, except that cyclohexanethanol (1 g, 7.8 mmol) and 2-methoxy-4-hydroxybenzaldehyde (1.19 g, 7.8 mmol) were added in place of cyclohexanemethanol and 4-hydroxy-3-methylbenzaldehyde, and 2.25 g of triphenylphosphine (8.58 mmol) was used (1.78 g, yield: 87.3%).

Then, Derivative 60 having the above formula, 5-(4-(2-cyclohexylethoxy)-2-methoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.15 g, yield: 83.9%).

$^1$H NMR (300 MHz, DMSO-d6) δ 12.446 (s, 1H), 7.915 (s, 1H), 7.907 (d, J=8.4 Hz, 1H), 6.709 (d, J=8.4 Hz, 1H), 6.667 (s, 1H), 4.102 (t, J=5.1 Hz, 2H), 3.878 (s, 3H), 1.587-1.750 (m, 7H), 1.451-1.586 (m, 1H), 1.104-1.271 (m, 3H), 0.884-0.994 (m, 2H)

Example 61

Preparation of Derivative 61 According to the Present Invention

Derivative 61 having the following formula was prepared as follows.

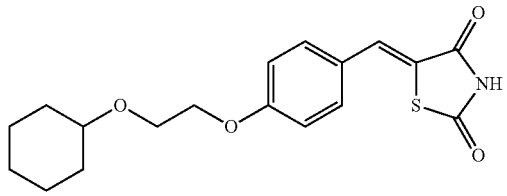 [SMILES: O=C1NC(=O)/C(=C/c2ccc(OCCOC3CCCCC3)cc2)S1]

[Formula of Derivative 61]

The intermediate product, 4-(2-(cyclohexyloxy)ethoxy)benzaldehyde, was prepared in accordance with the same method as described in Example 51, except that 2-(cyclohexyloxy)ethanol (1 g, 6.9 mmol) and 4-hydroxybenzaldehyde (0.84 g, 6.9 mmol) were added in place of cyclohexanemethanol and 4-hydroxy-3-methylbenzaldehyde, and 1.99 g of triphenylphosphine (7.59 mmol) was used (1.46 g, yield: 84.9%).

Then, Derivative 61 having the above formula, 5-(4-(2-(Cyclohexyloxy)ethoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.14 g, yield: 82.0%).

$^1$H NMR (300 MHz, DMSO-d6) δ 8.645 (s, 1H), 7.733 (s, 1H), 7.437 (d, J=14.7 Hz, 2H), 7.020 (d, J=14.7 Hz, 2H), 4.197 (t, J=9.9 Hz, 2H), 3.302 (t, J=9.9 Hz, 2H), 3.321-3.397 (m, 1H), 1.956-2.179 (m, 2H), 1.754-1.770 (m, 2H), 1.549-1.592 (m, 1H), 1.218-1.389 (m, 5H)

Example 62

Preparation of Derivative 62 According to the Present Invention

Derivative 62 having the following formula was prepared as follows.

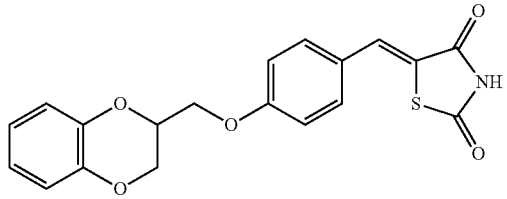 [SMILES: O=C1NC(=O)/C(=C/c2ccc(OCC3COc4ccccc4O3)cc2)S1]

[Formula of Derivative 62]

The intermediate product, 4-((2,3-dihydrobenzo[b][1,4]dioxin-2-yl)methoxy)benzaldehyde, was prepared in accordance with the same method as described in Example 51, except that 2-hydroxymethyl-1,4-benzodioxane (1 g, 6.0 mmol) and 4-hydroxybenzaldehyde (0.73 g, 6.0 mmol) were added in place of cyclohexanemethanol and 4-hydroxy-3-methylbenzaldehyde, and 1.73 g of triphenylphosphine (6.6 mmol) was used (1.34 g, yield: 82.7%).

Then, Derivative 62 having the above formula, 5-(4-((2,3-Dihydrobenzo[b][1,4]dioxin-2-yl)methoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.12 g, yield: 82.4%).

¹H NMR (300 MHz, DMSO-d6) δ 12.513 (s, 1H), 7.733 (s, 1H), 7.576 (d, J=8.7 Hz, 2H), 7.167 (d, J=8.7 Hz, 2H), 6.817-6.922 (m, 4H), 4.458-4.578 (m, 1H), 4.409-4.455 (m, 1H), 4.263-4.409 (m, 2H), 4.111-4.173 (m, 1H)

Example 63

Preparation of Derivative 63 According to the Present Invention

Derivative 63 having the following formula was prepared as follows.

[Formula of Derivative 63]

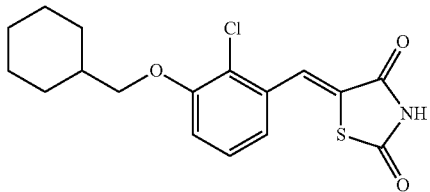 [SMILES: O=C1NC(=O)/C(=C/c2cccc(OCC3CCCCC3)c2Cl)S1]

The intermediate product, 2-chloro-3-(cyclohexylmethoxy)benzaldehyde, was prepared in accordance with the same method as described in Example 51, except that 2-chloro-3-hydroxybenzaldehyde (1.38 g, 8.8 mmol) was added in place of 4-hydroxy-3-methylbenzaldehyde, and 1 g of cyclohexanmethanol (8.8 mmol) and 2.54 g of triphenylphosphine (9.68 mmol) were used (1.89 g, yield: 85.5%).

Then, Derivative 63 having the above formula, 5-(2-chloro-3-(cyclohexylmethoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.06 g, yield: 76.3%).

¹H NMR (300 MHz, DMSO-d6) δ 7.721 (s, 1H), 7.514 (d, J=9.3 Hz, 1H), 7.138-7.327 (m, 1H), 7.142 (d, J=9.3 Hz, 1H), 3.862 (d, J=6.0 Hz, 2H), 1.7.3-1.933 (m, 6H), 1.088-1.579 (m, 5H)

Example 64

Preparation of Derivative 64 According to the Present Invention

Derivative 64 having the following formula was prepared as follows.

[Formula of Derivative 64]

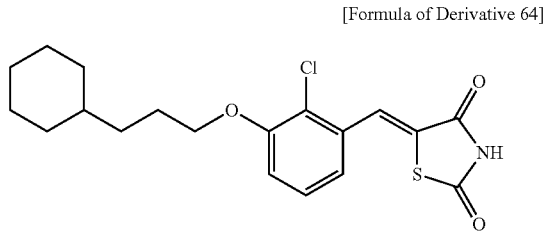

The intermediate product, 2-chloro-3-(cyclohexylpropoxy)benzaldehyde, was prepared in accordance with the same method as described in Example 51, except that 3-cyclohexyl-1-propanol (1 g, 7.0 mmol) and 2-chloro-3-hydroxybenzaldehyde (855 mg, 7.0 mmol) were added in place of cyclohexanemethanol and 4-hydroxy-3-methylbenzaldehyde, and 2.02 g of triphenylphosphine (7.7 mmol) was used (1.65 g, yield: 83.8%).

Then, Derivative 64 having the above formula, 5-(2-chloro-3-(cyclohexylpropoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.00 g, yield: 74.1%).

¹H NMR (300 MHz, DMSO-d6) δ 7.943 (s, 1H), 7.521 (d, J=9.3 Hz, 1H), 7.261-7.333 (m, 1H), 7.152 (d, J=9.3 Hz, 1H), 4.045 (t, J=13.2 Hz, 2H), 1.829-1.925 (m, 2H), 1.578-1.731 (m, 5H), 1.091-1.426 (m, 6H), 0.859-0.883 (m, 2H)

Example 65

Preparation of Derivative 65 According to the Present Invention

Derivative 65 having the following formula was prepared as follows.

[Formula of Derivative 65]

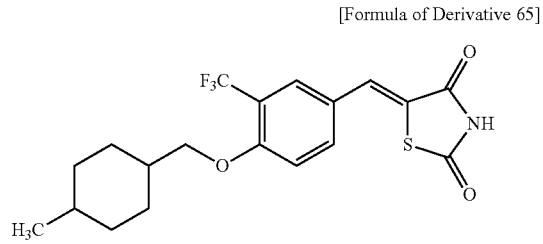

30 ml of dried dimethylformamide containing 4-methyl-1-cyclohexanemethanol (1 g, 7.8 mmol) was added to sodium hydride (342.2 mg, 8.58 mmol, 60% dispersed oil) and slowly stirred at room temperature under nitrogen. The mixture was further stirred at room temperature for 30 minutes and added to 5 ml of dried dimethylformamide containing 4-fluoro-3-(trifluoromethyl)benzaldehyde (1.2 g, 7.8 mmol) over 10 minutes. Then, the reaction mixture was stirred at room temperature for 18 hours until the initial product disappeared. 20 ml of ice water was added thereto, and the resulting mixture was extracted with ethyl acetate and water. The organic layer was washed with water several times, dried with anhydrous magnesium sulfate, filtered and solvent-evaporated. The residual oil was chromatographed on the silica gel column (hexane:ethyl acetate=20:1) to afford 4-((methylcyclohexyl)methoxy)-3-(trifluoromethyl)benzaldehyde (1.64 g, yield: 87%).

Then, Derivative 65 having the above formula, 5-[4-((4-methylcyclohexyl)methoxy)-3-(trifluoromethyl)benzylidene]thiazolidine-2,4-dione, was obtained in accordance with the same method as described in Step 2 of Example 51, except that 4-(2-cyclomethoxy)-3-methylbenzaldehyde was replaced by the intermediate obtained in the above (1.02 g, yield: 76.1%).

¹H NMR (300 MHz, DMSO-d6) δ 12.602 (s, 1H), 7.878 (s, 1H), 7.829 (s, 1H), 7.805 (d, J=8.4 Hz, 1H), 7.101 (d, J=8.4 Hz, 1H), 4.117 (d, J=6.6 Hz, 1H), 4.016 (d, J=6.6 Hz, 1H), 1.685-1.907 (m, 4H), 1.454-1.523 (m, 4H), 1.083-1.122 (m, 2H), 0.927 (d, J=6.9 Hz, 3H)

Example 66

Preparation of Derivative 66 According to the Present Invention

Derivative 66 having the following formula was prepared as follows.

[Formula of Derivative 66]

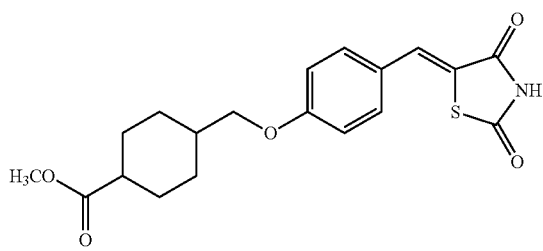 [SMILES: COC(=O)C1CCC(COc2ccc(/C=C3\SC(=O)NC3=O)cc2)CC1]

Thionyl chloride (1.50 g, 12.6 mmol) was added dropwise to 4-hydroxymethyl-1-cyclohexane carboxylic acid (1 g, 6.3 mmol) dissolved in 10 ml of methanol (reagent grade) at room temperature. The mixture was heated overnight under reflux and concentrated under reduced pressure to obtain 4-hydroxymethyl-1-cyclohexane carboxylic acid by silica gel chromatography (0.78 g, yield: 71.6%). Further, 4-((4-acetylcyclohexyl)methoxy)benzaldehyde was obtained by silica gel column chromatography using the eluting solvent of hexane:ethyl acetate=10:1 (0.86 g, yield: 76.8%).

Then, Derivative 66 having the above formula, methyl-4-((4-((2,4-dioxothiazolidine-5-ylidene)methyl)phenoxy)methyl)cyclohexane carboxylate, was obtained in accordance with the same method as described in Step 2 of Example 51, except that 4-(2-cyclomethoxy)-3-methylbenzaldehyde was replaced by the two compounds obtained in the above (1.03 g, yield: 74.1%).

$^1$H NMR (300 MHz, DMSO-d6) δ 12.482 (s, 1H), 7.736 (s, 1H), 7.552 (d, J=15.9 Hz, 4H), 7.580 (t, J=9.0 Hz, 2H), 7.103 (d, J=9.0 Hz, 2H), 3.904 (d, J=6.6 Hz, 2H), 3.610 (s, 3H), 2.604-2.623 (m, 1H), 1.891-1.984 (m, 3H), 1.450-1.675 (m, 4H), 1.273-1.342 (m, 2H)

Example 67

Preparation of Derivative 67 According to the Present Invention

Derivative 67 having the following formula was prepared as follows.

[Formula of Derivative 67]

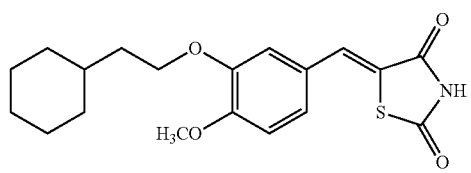 [SMILES: COc1ccc(/C=C2\SC(=O)NC2=O)cc1OCCC1CCCCC1]

The intermediate product, 3-(2-cyclohexylethoxy)-4-methoxybenzaldehyde, was prepared in accordance with the same method as described in Example 51, except that cyclohexaneethanol (1 g, 7.8 mmol) and isovanillin (1.19 g, 7.8 mmol) were added in place of cyclohexanemethanol and 4-hydroxy-3-methylbenzaldehyde, and 2.25 g of triphenylphosphine (8.58 mmol) was used (1.68 g, yield: 82.1%).

Then, Derivative 67 having the above formula, 5-(3-(2-cyclohexylethoxy)-4-methoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.24 g, yield: 87.2%).

$^1$H NMR (300 MHz, DMSO-d6) δ 12.436 (s, 1H), 8.165 (s, 1H), 7.941 (d, J=9.5 Hz, 1H), 7.661 (s, 1H), 7.273 (d, J=9.5 Hz, 1H), 4.233 (t, J=13.5 Hz, 2H), 3.864 (s, 3H), 1.682-1.759 (m, 7H), 1.442-1.586 (m, 1H), 1.182-1.242 (m, 3H), 0.896-0.926 (m, 2H)

Example 68

Preparation of Derivative 68 According to the Present Invention

Derivative 68 having the following formula was prepared as follows.

[Formula of Derivative 68]

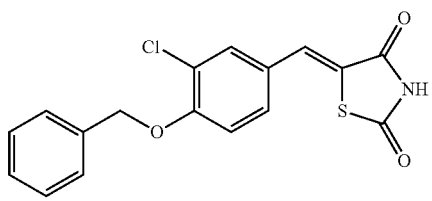 [SMILES: O=C1NC(=O)/C(=C/c2ccc(OCc3ccccc3)c(Cl)c2)S1]

The intermediate product, 4-(benzyloxy)-3-chlorobenzaldehyde, was prepared in accordance with the same method as described in Example 51, except that benzylalcohol (1 g, 9.2 mmol) and 3-chloro-4-hydroxybenzaldehyde (1.44 g, 9.2 mmol) were added in place of cyclohexanemethanol and 4-hydroxy-3-methylbenzaldehyde, and 2.65 g of triphenylphosphine (10.12 mmol) was used (1.76 g, yield: 77.2%).

Then, Derivative 68 having the above formula, 5-(4-(benzyloxy)-3-chlorobenzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.21 g, yield: 86.4%).

$^1$H NMR (300 MHz, DMSO-d6) δ 8.024 (s, 1H), 7.936 (s, 1H), 7.747 (d, J=10.2 Hz, 1H), 7.324-7.479 (m, 5H), 7.093 (d, J=10.2 Hz, 1H), 5.259 (s, 2H)

Example 69

Preparation of Derivative 69 According to the Present Invention

Derivative 69 having the following formula was prepared as follows.

[Formula of Derivative 69]

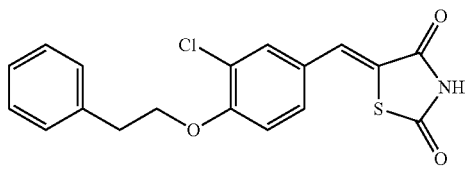 [SMILES: O=C1NC(=O)/C(=C/c2ccc(OCCc3ccccc3)c(Cl)c2)S1]

The intermediate product, 3-chloro-4-phenylethoxybenzaldehyde, was prepared in accordance with the same method as described in Example 51, except that 2-phenylethanol (1 g, 8.2 mmol) and 3-chloro-4-hydroxybenzaldehyde (1.28 g, 8.2 mmol) were added in place of cyclohexanemethanol and 4-hydroxy-3-methylbenzaldehyde, and 2.37 g of triphenylphosphine (9.02 mmol) was used (1.69 g, yield: 79.3%).

Then, Derivative 69 having the above formula, 5-(3-chloro-4-phenylethoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.19 g, yield: 86.2%).

$^1$H NMR (300 MHz, DMSO-d6) δ 12.547 (s, 1H), 7.894 (s, 1H), 7.694 (s, 1H), 7.533 (d, J=11.1 Hz, 1H), 7.311-7.348 (m, 5H), 7.248 (d, J=11.1 Hz, 1H), 4.367 (t, J=13.5 Hz, 2H), 3.109 (t, J=13.5 Hz, 2H)

Example 70

Preparation of Derivative 70 According to the Present Invention

Derivative 70 having the following formula was prepared as follows.

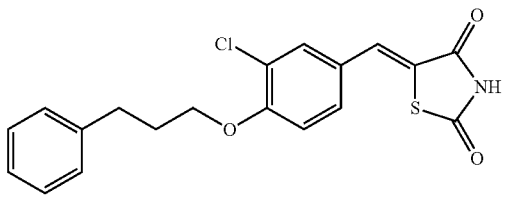 [SMILES: O=C1NC(=O)/C(=C/c2ccc(OCCCc3ccccc3)c(Cl)c2)S1]

[Formula of Derivative 70]

The intermediate, 3-chloro-4-(3-phenylpropoxy)benzaldehyde, was prepared in accordance with the same method as described in Example 51, except that 3-phenyl-1-propanol (1 g, 7.3 mmol) and 3-chloro-4-hydroxybenzaldehyde (1.14 g, 7.3 mmol) were added in place of cyclohexanmethanol and 4-hydroxy-3-methylbenzaldehyde, and 2.11 g of triphenylphosphine (8.03 ml) was used (1.48 g, yield: 73.6%).

Then, Derivative 70 having the above formula, 5-(3-chloro-4-(3-phenylpropoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.13 g, yield: 83.1%).

$^1$H NMR (300 MHz, DMSO-d6) δ 12.538 (s, 1H), 7.714 (s, 1H), 7.706 (s, 1H), 7.533 (d, J=10.8 Hz, 1H), 7.158 7.311 (m, 6H), 4.143 (t, J=12.3 Hz, 2H), 2.802 (t, J=12.8 Hz, 2H), 2.022-2.093 (m, 2H)

Example 71

Preparation of Derivative 71 According to the Present Invention

Derivative 71 having the following formula was prepared as follows.

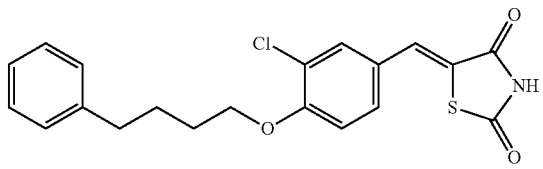 [SMILES: O=C1NC(=O)/C(=C/c2ccc(OCCCCc3ccccc3)c(Cl)c2)S1]

[Formula of Derivative 71]

The intermediate product, 3-chloro-4-(4-phenylbutoxy)benzaldehyde, was prepared in accordance with the same method as described in Example 51, except that 4-phenyl-1-butanol (1 g, 6.7 mmol) and 3-chloro-4-hydroxybenzaldehyde (1.05 g, 6.7 mmol) were added in place of cyclohexanemethanol and 4-hydroxy-3-methylbenzaldehyde, and 1.93 g of triphenylphosphine (7.37 mmol) was used (1.43 g, yield: 74.5%).

Then, Derivative 71 having the above formula, 5-(3-chloro-4-(4-phenylbutoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.04 g, yield: 77.6%).

$^1$H NMR (300 MHz, DMSO-d6) δ 12.577 (s, 1H), 7.720 (s, 1H), 7.693 (s, 1H), 7.529 (d, J=10.5 Hz, 1H), 7.135-7.304 (m, 6H), 4.155 (t, J=5.7 Hz, 2H), 2.671 (t, J=7.2 Hz, 2H), 1.741-1.761 (m, 4H)

Example 72

Preparation of Derivative 72 According to the Present Invention

Derivative 72 having the following formula was prepared as follows.

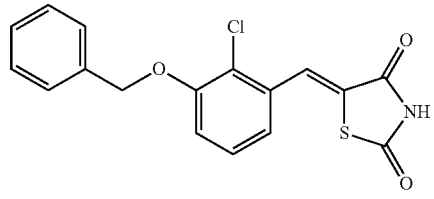

[Formula of Derivative 72]

The intermediate product, 3-(benzyloxy)-2-chlorobenzaldehyde, was prepared in accordance with the same method as described in Example 51, except that benzylalcohol (1 g, 9.2 mmol) and 2-chloro-3-hydroxybenzaldehyde (1.44 g, 9.2 mmol) were added in place of cyclohexanemethanol and 4-hydroxy-3-methylbenzaldehyde, and 2.65 g of triphenylphosphine (10.12 mmol) was added (1.69 g, yield: 74.1%).

Then, Derivative 72 having the above formula, 5-(3-(benzyloxy)-2-chlorobenzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.05 g, yield: 75%).

$^1$H NMR (300 MHz, DMSO-d6) δ 7.753 (s, 1H), 7.498 (d, J=7.8 Hz, 1H), 7.339-7.413 (m, 6H), 7.241 (d, J=7.8 Hz, 1H), 5.243 (s, 2H)

Example 73

Preparation of Derivative 73 According to the Present Invention

Derivative 73 having the following formula was prepared as follows.

[Formula of Derivative 73]

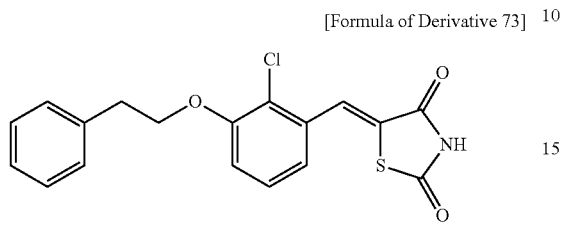

The intermediate product, 2-chloro-3-phenylethoxybenzaldehyde, was prepared in accordance with the same method as described in Example 51, except that 2-phenylethanol (1 g, 8.2 mmol) and 2-chloro-3-hydroxybenzaldehyde (1.28 g, 8.2 mmol) were added in place of cyclohexanemethanol and 4-hydroxy-3-methylbenzaldehyde, and 2.37 g of triphenylphosphine (9.02 mmol) was used (1.60 g, yield: 75.1%).

Then, Derivative 73 having the above formula, 5-(2-chloro-3-phenylethoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.07 g, yield: 77.5%).

$^1$H NMR (300 MHz, DMSO-d6) δ 7.894 (s, 1H), 7.459 (d, J=7.8 Hz, 1H), 7.141-7.495 (m, 6H), 7.164 (d, J=7.8 Hz, 1H), 4.328 (t, J=13.5 Hz, 2H), 3.107 (t, J=13.2 Hz, 2H)

Example 74

Preparation of Derivative 74 According to the Present Invention

Derivative 74 having the following formula was prepared as follows.

[Formula of Derivative 74]

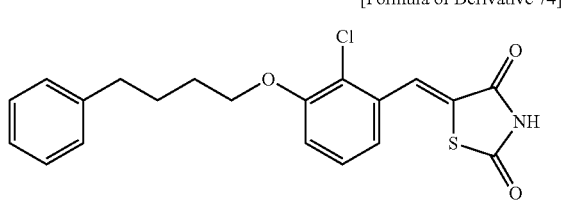

The intermediate product, 2-chloro-3-(4-phenylbutoxy)benzaldehyde, was prepared in accordance with the same method as described in Example 51, except that 4-phenyl-1-butanol (1 g, 6.7 mmol) and 2-chloro-3-hydroxybenzaldehyde (1.05 g, 6.7 mmol) were added in place of cyclohexanemethanol and 4-hydroxy-3-methylbenzaldehyde, and 1.93 g of triphenylphosphine (7.37 mmol) was used (1.40 g, yield: 72.9%).

Then, Derivative 74 having the above formula, 5-(2-chloro-3-(4-phenylbutoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.10 g, yield: 82.1%).

$^1$H NMR (300 MHz, DMSO-d6) δ 12.719 (s, 1H), 7.932 (s, 1H), 7.474 (t, J=8.1 Hz, 1H), 7.151-7.303 (m, 7H), 4.145 (t, J=5.1 Hz, 2H), 2.658 (t, J=5.3 Hz, 2H), 2.084 (t, J=2.7 Hz, 4H)

Example 75

Preparation of Derivative 75 According to the Present Invention

Derivative 75 having the following formula was prepared as follows.

[Formula of Derivative 75]

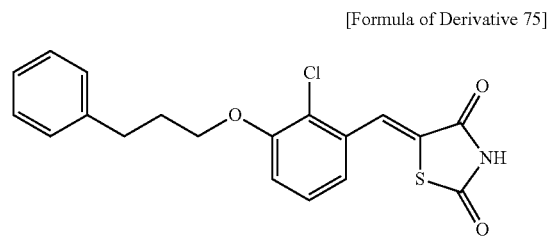

The intermediate product, 2-chloro-3-(3-phenylpropoxy)benzaldehyde, was prepared in accordance with the same method as described in Example 51, except that 3-phenyl-1-propanol (1 g, 7.3 mmol) and 2-chloro-3-hydroxybenzaldehyde (1.14 g, 7.3 mmol) were added in place of cyclohexanemethanol and 4-hydroxy-3-methylbenzaldehyde, and 2.11 g of triphenylphosphine (8.03 mmol) was added (1.30 g, yield: 64.6%).

Then, Derivative 75 having the above formula, 5-(2-chloro-3-(3-phenylpropoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.12 g, yield: 82.4%).

$^1$H NMR (300 MHz, DMSO-d6) δ 7.927 (s, 1H), 7.464 (t, J=7.8 Hz, 1H), 7.151 7.312 (m, 7H), 4.109 (t, J=12.3 Hz, 2H), 2.813 (t, J=12.5 Hz, 2H), 2.084 (t, J=13.2 Hz, 2H)

Example 76

Preparation of Derivative 76 According to the Present Invention

Derivative 76 having the following formula was prepared as follows.

[Formula of Derivative 76]

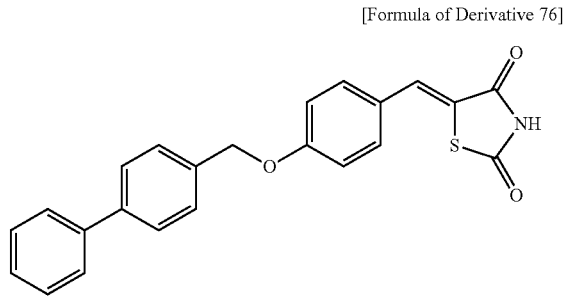

Example 77

Preparation of Derivative 77 According to the Present Invention

Derivative 77 having the following formula was prepared as follows.

[Formula of Derivative 77]

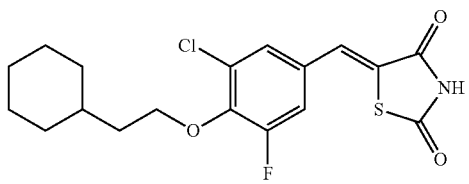 [SMILES: O=C1NC(=O)/C(=C/c2cc(F)c(OCCC3CCCCC3)c(Cl)c2)S1]

The intermediate product, 3-chloro-5-fluoro-4-(2-cyclohexylethoxy)benzaldehyde, was prepared in accordance with the same method as described in Example 51, except that cyclohexanethanol (1 g, 7.8 mmol) and 3-chloro-5-fluoro-4-hydroxybenzaldehyde (1.36 g, 7.8 mmol) were added in place of cyclohexanemethanol and 4-hydroxy-3-methylbenzaldehyde, and 2.25 g of triphenylphosphine (8.58 mmol) was used (1.79 g, yield: 80.6%).

Then, Derivative 77 having the above formula, 5-(3-chloro-5-fluoro-4-(2-cyclohexylethoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.0 g, yield: 75.4%).

$^1$H NMR (300 MHz, DMSO-d6) δ 12.061 (s, 1H), 7.950 (s, 1H), 7.532 (s, 1H), 7.488 (s, 2H), 4.178 (t, J=15.5 Hz, 2H), 1.588-1.749 (m, 7H), 1.505-1.580 (m, 1H), 1.107-1.237 (m, 3H), 0.903-0.980 (m, 2H)

Example 78

Preparation of Derivative 78 According to the Present Invention

Derivative 78 having the following formula was prepared as follows.

[Formula of Derivative 78]

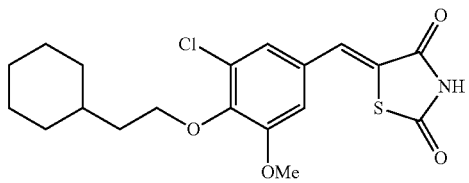 [SMILES: COc1cc(/C=C2\SC(=O)NC2=O)cc(Cl)c1OCCC1CCCCC1]

The intermediate product, 3-chloro-4-(2-cyclohexylethoxy)-5-methoxybenzaldehyde, was prepared in accordance with the same method as described in Example 51, except that cyclohexaneethanol (1 g, 7.8 mmol) and 3-chloro-4-hydroxy-5-methoxybenzaldehyde (1.46 g, 7.8 mmol) were added in place of cyclohexanemethanol and 4-hydroxy-3-methylbenzaldehyde, and 2.25 g of triphenylphosphine (8.58 mmol) was used (1.8 g, yield: 77.9%).

Then, Derivative 78 having the above formula, 5-(3-chloro-4-(2-cyclohexylethoxy)-5-methoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.12 g, yield: 84.2%).

$^1$H NMR (300 MHz, DMSO-d6) δ 12.656 (s, 1H), 7.738 (s, 1H), 7.262 (s, 1H), 7.239 (s, 1H), 4.043 (t, J=12.6 Hz, 2H), 3.872 (s, 3H), 1.557-1.754 (m, 8H), 1.144-1.239 (m, 3H), 0.891-0.964 (m, 2H)

Example 79

Preparation of Derivative 79 According to the Present Invention

Derivative 79 having the following formula was prepared as follows.

[Formula of Derivative 79]

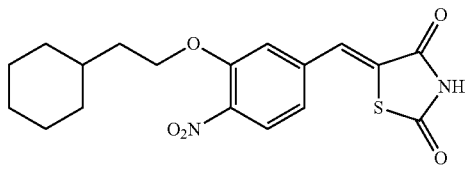 [SMILES: O=C1NC(=O)/C(=C/c2ccc([N+](=O)[O-])c(OCCC3CCCCC3)c2)S1]

The intermediate product, 3-(2-cyclohexylethoxy)-4-nitrobenzaldehyde, was prepared in accordance with the same method as described in Example 51, except that cyclohexaneethanol (1 g, 7.8 mmol) and 3-hydroxy-4-nitrobenzaldehyde (1.30 g, 7.8 mmol) were added in place of cyclohexanemethanol and 4-hydroxy-3-methylbenzaldehyde, and 2.25 g of triphenylphosphine (8.58 mmol) was added (1.78 g, yield: 82.4%).

Then, Derivative 79 having the above formula, 5-(3-(2-cyclohexylethoxy)-4-nitrobenzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.24 g, yield: 87%).

$^1$H NMR (300 MHz, DMSO-d6) δ 12.644 (s, 1H), 8.003 (d, J=8.4 Hz, 1H), 7.799 (s, 1H), 7.611 (s, 1H), 7.273 (s, J=8.4

---

The intermediate product, 4-(biphenyl-4-ylmethoxy)benzaldehyde, was prepared in accordance with the same method as described in Example 51, except that 4-hydroxymethylbiphenyl (1 g, 5.4 mmol) and 4-hydroxybenzaldehyde (0.66 g, 5.4 mmol) were added in place of cyclohexanemethanol and 4-hydroxy-3-methylbenzaldehyde, and 1.56 g of triphenylphosphine (5.94 mmol) was added (1.20 g, yield: 76.9%).

Then, Derivative 76 having the above formula, 5-(4-(biphenyl-4-ylmethoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.12 g, yield: 83.6%).

$^1$H NMR (300 MHz, DMSO-d6) δ 12.513 (s, 1H), 7.735 (s, 1H), 7.703 (t, J=15.9 Hz, 4H), 7.580 (t, J=15.9 Hz, 4H), 7.486 (t, J=14.7 Hz, 2H), 7.384 (m, 1H), 7.206 (d, J=8.7 Hz, 2H), 5.235 (s, 2H)

Hz, 1H), 4.255 (t, J=13.5 Hz, 2H), 1.618-1.746 (m, 7H), 1.401-1.546 (m, 1H), 1.144-1.323 (m, 3H), 0.928-0.1.006 (m, 2H)

Example 80

Preparation of Derivative 80 According to the Present Invention

Derivative 80 having the following formula was prepared as follows.

[Formula of Derivative 80]

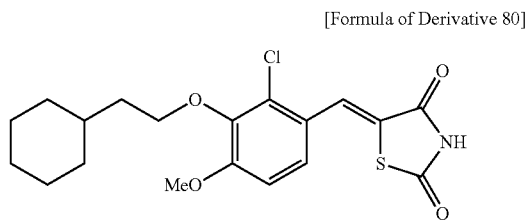

The intermediate product, 2-chloro-3-(2-cyclohexy-lethoxy)-4-methoxybenzaldehyde, was prepared in accordance with the same method as described in Example 51, except that cyclohexaneethanol (1 g, 7.8 mmol) and 2-chloro-3-hydroxy-4-methoxybenzaldehyde (1.46 g, 7.8 mmol) were added in place of cyclohexanemethanol and 4-hydroxy-3-methylbenzaldehyde, and 2.25 g of triphenylphosphine (8.58 mmol) was added (2.03 g, yield: 88.3%).

Then, Derivative 80 having the above formula, 5-(2-chloro-3-(2-cyclohexylethoxy)-4-methoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.04 g, yield: 78.1%).

$^1$H NMR (300 MHz, DMSO-d6) δ 12.743 (s, 1H), 7.319 (s, J=8.7 Hz, 1H), 7.247 (s, J=8.7 Hz, 1H), 4.007 (t, J=12.6 Hz, 2H), 3.890 (s, 3H), 1.516-1.764 (m, 8H), 1.109-1.245 (m, 3H), 0.894-0.970 (m, 2H)

Example 81

Preparation of Derivative 81 According to the Present Invention

Derivative 81 having the following formula was prepared as follows.

[Formula of Derivative 81]

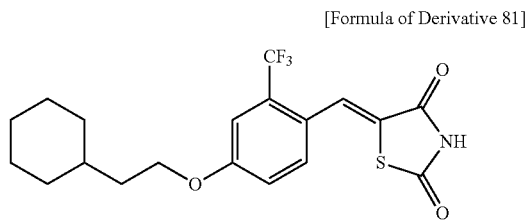

Sodium hydride (343.2 mg, 8.58 mmol, 60% dispersed oil) was slowly added to cyclohexaneethanol (1 g, 7.8 mmol) dissolved in 30 ml of dried dimethylformamide under nitrogen at room temperature while stirring. The mixture was further stirred at room temperature for 30 minutes. Then, 4-fluoro-2-(trifluoromethyl)benzaldehyde (1.2 g, 7.8 mmol) dissolved in dried dimethylformamide was added thereto over 10 minutes and stirred at room temperature for 18 hours until the initial product disappeared. Subsequently, ice water was added thereto, and the resulting mixture was extracted with ethyl acetate and water. The organic layer was washed with water several times, dried with anhydrous magnesium sulfate, filtered and solvent-evaporated. The residual oil was chromatographed on the silica gel column (hexane:ethyl acetate-20:1) to afford the intermediate, 4-(2-cyclohexy-lethoxy)-2-(trifluoromethyl)benzaldehyde (1.77 g, yield: 75.6%).

Then, Derivative 81 having the above formula, 5-(4-(2-cyclohexylethoxy)-2-(trifluoromethyl)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.06 g, yield: 79.7%).

$^1$H NMR (300 MHz, DMSO-d6) δ 12.731 (s, 1H), 7.778 (s, 1H), 7.689 (d, J=9.0 Hz, 1H), 7.407 (d, J=9.0 Hz, 1H), 7.371 (s, 1H), 4.168 (t, J=12.9 Hz, 2H), 1.598-1.750 (m, 7H), 1.455-1.598 (m, 1H), 1.099-1.265 (m, 3H), 0.884-0.994 (m, 2H)

Example 82

Preparation of Derivative 82 According to the Present Invention

Derivative 82 having the following formula was prepared as follows.

[Formula of Derivative 82]

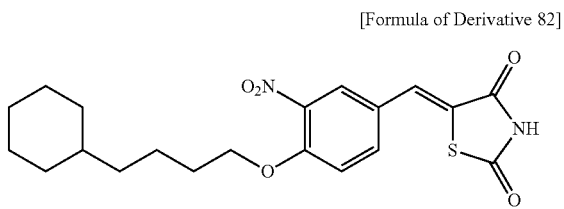

The intermediate product, 4-(2-cyclohexylbutoxy)-3-nitrobenzaldehyde, was prepared in accordance with the same method as described in Example 51, except that 4-cyclohexyl-1-butanol (1 g, 6.4 mmol) and 4-hydroxy-3-nitrobenzaldehyde (1.07 g, 6.4 mmol) were added in place of cyclohexanemethanol and 4-hydroxy-3-methylbenzaldehyde, and 1.85 g of triphenylphosphine (7.04 mmol) was used (1.32 g, yield: 81%).

Then, Derivative 82 having the above formula, 5-(4-(2-cyclohexylbutoxy)-3-nitrobenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.23 g, yield: 77.8%).

$^1$H NMR (300 MHz, DMSO-d6) δ 8.134 (s, 1H), 7.847 (d, J=9.0 Hz, 2H), 7.787 (s, 1H), 7.527 (d, J=9.0 Hz, 2H), 4.225 (t, J=12.3 Hz, 2H), 1.625-1.751 (m, 7H), 1.419-1.467 (m, 2H), 1.079-1.220 (m, 6H), 0.831-0.896 (m, 2H)

Example 83

Preparation of Derivative 83 According to the Present Invention

Derivative 83 having the following formula was prepared as follows.

[Formula of Derivative 83]

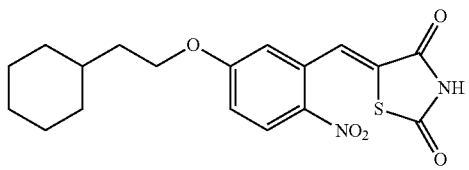 [SMILES: O=C1NC(=O)/C(=C/c2cc(OCCC3CCCCC3)ccc2[N+](=O)[O-])S1]

The intermediate product, 5-(2-cyclohexylethoxy)-2-nitrobenzaldehyde, was prepared in accordance with the same method as described in Example 51, except that cyclohexaneethanol (1 g, 7.8 mmol) and 5-hydroxy-2-nitrobenzaldehyde (1.30 g, 7.8 mmol) were added in place of cyclohexanemethanol and 4-hydroxy-3-methylbenzaldehyde, and 2.25 g of triphenylphosphine (8.58 mmol) was used (1.68 g, yield: 77.8%).

Then, Derivative 83 having the above formula, 5-(5-(2-cyclohexylethoxy)-2-nitrobenzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.24 g, yield: 87%).

$^1$H NMR (300 MHz, DMSO-d6) δ 12.644 (s, 1H), 8.003 (d, J=8.4 Hz, 1H), 7.799 (s, 1H), 7.611 (s, 1H), 7.273 (s, J=8.4 Hz, 1H), 4.255 (t, J=13.5 Hz, 2H), 1.618-1.746 (m, 7H), 1.401-1.546 (m, 1H), 1.144-1.323 (m, 3H), 0.928-0.1.006 (m, 2H)

Example 84

Preparation of Derivative 84 According to the Present Invention

Derivative 84 having the following formula was prepared as follows.

[Formula of Derivative 84]

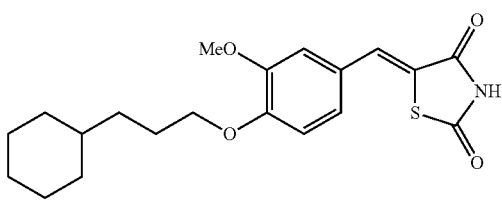 [SMILES: COc1cc(/C=C2\SC(=O)NC2=O)ccc1OCCCC1CCCCC1]

The intermediate product, 4-(2-cyclohexylpropoxy)-3-methoxybenzaldehyde, was prepared in accordance with the same method as described in Example 51, except that 3-cyclohexyl-1-propanol (1 g, 7.0 mmol) and 4-hydroxy-3-methoxybenzaldehyde (1.07 g, 7.0 mmol) were added in place of cyclohexanemethanol and 4-hydroxy-3-methylbenzaldehyde, respectively, and 2.02 g of triphenylphosphine (7.7 mmol) was used (1.64 g, yield: 84.5%).

Then, Derivative 84 having the above formula, 5-(4-(2-cyclohexylpropoxy)-3-methoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.13 g, yield: 83.1%).

$^1$H NMR (300 MHz, DMSO-d6) δ 8.219 (s, 1H), 7.694 (s, 1H), 7.014 (d, J=10.2 Hz, 2H), 6.893 (d, J=10.2 Hz, 2H), 6.764 (s, 1H), 4.123 (t, J=14.4 Hz, 2H), 3.787 (s, 3H), 1.725 (t, J=14.4 Hz, 2H), 1.444-1.563 (m, 4H), 1.102-1.224 (m, 6H), 0.796-1.103 (m, 3H)

Example 85

Preparation of Derivative 85 According to the Present Invention

Derivative 85 having the following formula was prepared as follows.

[Formula of Derivative 85]

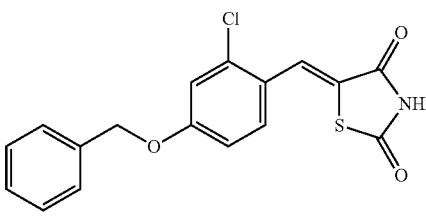

Sodium hydride (404.8 mg, 10.12 mmol, 60% dispersed oil) was slowly added to benzylalcohol (1 g, 9.2 mmol) dissolved in dried dimethylformamide (30 ml) under nitrogen at room temperature while stirring. Then, the mixture was further stirred at room temperature for 30 minutes. Thereto, 4-fluoro-2-chlorobenzaldehyde (1.46 g, 9.2 mmol) dissolved in dried dimethylformamide was added over 10 minutes and stirred at room temperature for 18 hours until the initial reaction product disappeared. Subsequently, ice water was added thereto, and the reaction mixture was extracted with ethyl acetate and water. The organic layer was washed with water several times, dried with anhydrous magnesium sulfate, filtered and solvent-evaporated. The residual oil was chromatographed on a silica gel column (hexane:ethyl acetate=20:1) to afford the intermediate, 4-(benzyloxy)-2-chlorobenzaldehyde (1.64 g, yield: 71.9%).

Then, Derivative 85 having the above formula, 5-(4-(benzyloxy)-2-chlorobenzylidene)thiazolidine-2,4-dione, was obtained in accordance with the same method as described in Step of Example 51, except that 4-(2-cyclomethoxy)-3-methylbenzaldehyde was replaced by the intermediate obtained in the above (0.98 g, yield: 70.1%).

$^1$H NMR (300 MHz, DMSO-d6) δ 7.850 (s, 1H), 7.561 (d, J=9.9 Hz, 1H), 7.332-7.499 (m, 6H), 7.221 (d, J=9.9 Hz, 1H), 5.224 (s, 2H)

Example 86

Preparation of Derivative 86 According to the Present Invention

Derivative 86 having the following formula was prepared as follows.

[Formula of Derivative 86]

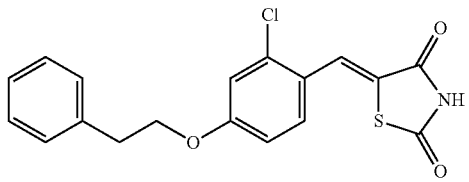 [SMILES: O=C1NC(=O)/C(=C/c2ccc(OCCc3ccccc3)cc2Cl)S1]

The intermediate product, 2-chloro-4-phenylethoxybenzaldehyde, was prepared in accordance with the same method as described in Example 85, except that 2-phenylethanol (1 g, 8.2 mmol) was used in place of benzylalcohol (1 g, 9.2 mmol) (1.64 g, yield: 77%).

Then, Derivative 86 having the above formula, 5-(2-chloro-4-phenylethoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (0.96 g, yield: 69.6%).

$^1$H NMR (300 MHz, DMSO-d6) δ 12.645 (s, 1H), 7.863 (s, 1H), 7.500 (d, J=7.8 Hz, 1H), 7.188-7.274 (m, 6H), 7.127 (d, J=7.8 Hz, 1H), 4.323 (t, J=13.5 Hz, 2H), 3.064 (t, J=13.8 Hz, 2H)

Example 87

Preparation of Derivative 87 According to the Present Invention

Derivative 87 having the following formula was prepared as follows.

[Formula of Derivative 87]

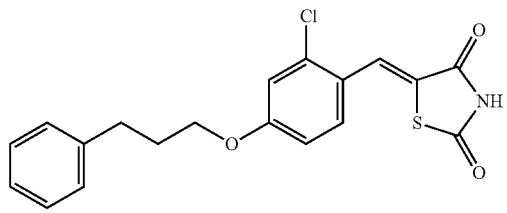 [SMILES: O=C1NC(=O)/C(=C/c2ccc(OCCCc3ccccc3)cc2Cl)S1]

The intermediate product, 2-chloro-4-phenylpropoxybenzaldehyde, was prepared in accordance with the same method as described in Example 85, except that 3-phenyl-1-propanol (1 g, 7.3 mmol) was used in place of benzylalcohol (1 g, 9.2 mmol) (1.4 g, yield: 69.7%).

Then, Derivative 87 having the above formula, 5-(2-chloro-4-phenylpropoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.0 g, yield: 72.7%).

$^1$H NMR (300 MHz, DMSO-d6) δ 12.548 (s, 1H), 7.924 (s, 1H), 7.482 (d, J=7.8 Hz, 1H), 7.200-7.368 (m, 6H), 7.212 (d, J=7.8 Hz, 1H), 4.139 (t, J=13.5 Hz, 2H), 3.156 (t, J=13.8 Hz, 2H), 2.591-2.622 (m, 2H)

Example 88

Preparation of Derivative 88 According to the Present Invention

Derivative 88 having the following formula was prepared as follows.

[Formula of Derivative 88]

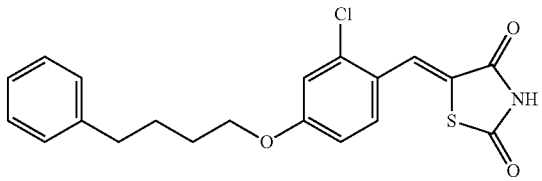 [SMILES: O=C1NC(=O)/C(=C/c2ccc(OCCCCc3ccccc3)cc2Cl)S1]

The intermediate product, 2-chloro-4-phenylbutoxybenzaldehyde, was prepared in accordance with the same method as described in Example 85, except that 4-phenyl-1-butanol (1 g, 6.7 mmol) was used in place of benzylalcohol (1 g, 9.2 mmol) (1.39 g, yield: 72.4%).

Then, Derivative 88 having the above formula, 5-(2-chloro-4-phenylbutoxybenzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (0.98 g, yield: 73.1%).

$^1$H NMR (300 MHz, DMSO-d6) δ 12.64 (s, 1H), 7.81 (s, 1H), 7.511 (d, J=9.3 Hz, 1H), 7.161-7.296 (m, 6H), 7.105 (d, J=9.3 Hz, 1H), 4.084 (t, J=12.9 Hz, 2H), 2.654 (t, J=13.8 Hz, 2H), 1.653-1.724 (m, 4H)

Example 89

Preparation of Derivative 89 According to the Present Invention

Derivative 89 having the following formula was prepared as follows.

[Formula of Derivative 89]

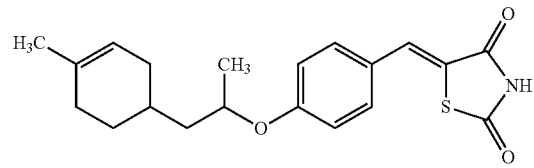 [SMILES: CC1=CCC(CC(C)Oc2ccc(/C=C3\SC(=O)NC3=O)cc2)CC1]

The intermediate product, 4-(2-(4-methylcyclohex-3-en-1-yl)propoxy)benzaldehyde, was prepared in accordance with the same method as described in Example 51, except that 4-(2-hydroperoxypropyl-1-methylcyclohex-1-en (1 g, 6.5 mmol) and 4-hydroxybenzaldehyde (0.79 g, 6.5 mmol) were used in place of cyclohexanmethanol and 4-hydroxy-3-methylbenzaldehyde, respectively, and 1.85 g of triphenylphosphine (7.05 mmol) was used (1.42 g, yield: 78.0%).

Then, Derivative 89 having the above formula, 5-{4-[2-(4-methylcyclohex-3-en-1-yl)propoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.23 g, yield: 89.8%).

$^1$H NMR (300 MHz, DMSO-d6) δ 12.496 (s, 1H), 7.726 (s, 1H), 7.547 (d, J=9.0 Hz, 2H), 7.106 (d, J=9.0 Hz, 2H), 5.344 (s, 1H), 3.991-4.042 (m, 1H), 3.844-3.898 (m, 1H), 1.085-2.069 (m, 7H), 1.711 (s, 3H), 1.347-1.637 (m, 2H), 1.257 (t, J=13.8 Hz, 3H), 0.860-0.882 (m, 1H)

Example 90

Preparation of Derivative 90 According to the Present Invention

Derivative 90 having the following formula was prepared as follows.

[Formula of Derivative 90]

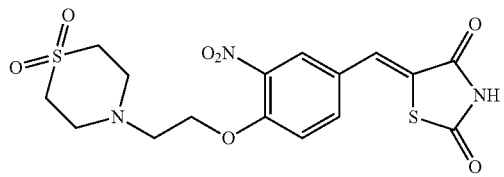

The intermediate product, 3-nitro-4-(2-thiomorpholine-1,1-dioxideethoxy)benzaldehyde, was prepared in accordance with the same method as described in Example 51, except that 4-(2-hydroxyethyl)thiomorpholine-1,1-dioxide (1 g, 5.6 mmol) and 3-nitro-4-hydroxybenzaldehyde (936 mg, 5.6 mmol) were used in place of cyclohexanmethanol and 4-hydroxy-3-methylbenzaldehyde, respectively, and 1.62 g of triphenylphosphine (6.2 mmol) was used (1.45 g, yield: 79.2%).

Then, Derivative 90 having the above formula, 5-[3-nitro-4-(2-thiomorpholine1,1-Dioxideethoxy)benzylidene]-2,4-thiazolidinedione, was obtained in accordance with the same method as described in Step 2 of Example 51, except that 4-(2-cyclomethoxy)-3-methylbenzaldehyde was replaced by the intermediate obtained in the above (0.88 g, yield: 67.7%).

$^1$H NMR (300 MHz, DMSO-d6) δ 12.630 (s, 1H), 8.148 (s, 1H), 7.860 (d, J=10.8 Hz, 1H), 7.560 (d, J=10.8 Hz, 1H), 7.782 (s, 1H), 4.360 (t, J=11.1 Hz, 2H), 3.043-3.119 (m, 8H), 2.976 (t, J=11.1 Hz, 2H)

Example 91

Preparation of Derivative 91 According to the Present Invention

Derivative 91 having the following formula was prepared as follows.

[Formula of Derivative 91]

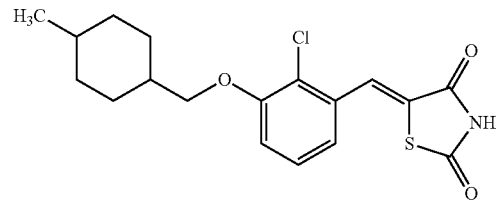 [SMILES: CC1CCC(COc2cccc(/C=C3\SC(=O)NC3=O)c2Cl)CC1]

The intermediate product, 2-chloro-3-[(4-methylcyclohexyl)methoxy]benzaldehyde, was prepared in accordance with the same method as described in Example 51, except that 4-methyl-1-cyclohexanmethanol (1 g, 5.6 mmol) and 2-chloro-3-hydroxybenzaldehyde (1.22 g, 7.8 mmol) were used in place of cyclohexanemethanol and 4-hydroxy-3-methylbenzaldehyde, respectively, and 2.25 g of triphenylphosphine (8.58 mmol) was used (1.49 g, yield: 74.1%).

Then, Derivative 91 having the above formula, 5-{2-chloro-3-[(4-methylcyclohexyl)methoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.12 g, yield: 81.2%).

$^1$H NMR (300 MHz, DMSO-d6) δ 8.242 (s, 1H), 7.262 (m, 1H), 7.111 (d, J=9.3 Hz, 1H), 7.025 (d, J=9.3 Hz, 1H), 3.961 (d, J=7.2 Hz, 2H), 2.038-2.076 (m, 1H), 1.456-1.810 (m, 5H), 1.233-1.339 (m, 2H), 0.954 (d, J=6.9 Hz, 1H), 0.900-1.416 (m, 2H)

Example 92

Preparation of Derivative 92 According to the Present Invention

Derivative 92 having the following formula was prepared as follows.

[Formula of Derivative 92]

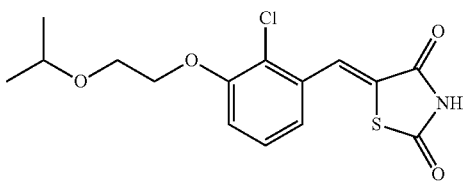 [SMILES: CC(C)OCCOc1cccc(/C=C2\SC(=O)NC2=O)c1Cl]

The intermediate product, 2-chloro-3-[2-(propan-2-yloxy)ethoxy]benzaldehyde, was prepared in accordance with the same method as described in Example 51, except that 2-isopropoxyethanol (1 g, 9.6 mmol) and 2-chloro-3-hydroxybenzaldehyde (1.50 g, 9.6 mmol) were used in place of cyclohexanmethanol and 4-hydroxy-3-methylbenzaldehyde, respectively, and 2.77 g of triphenylphosphine (10.56 mmol) was used (1.46 g, yield: 62.6%).

Then, Derivative 92 having the above formula, 5-[4-(2-phenylbutoxy)benzylidene]-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.06 g, yield: 75.7%).

$^1$H NMR (300 MHz, CDCl3) δ 8.623 (s, 1H), 8.208 (s, 1H), 7.263 (m, 1H), 7.111 (d, J=7.8 Hz, 1H), 7.055 (d, J=8.7 Hz, 1H), 4.223 (t, J=10.2 Hz, 2H), 3.880 (t, J=10.2 Hz, 2H), 3.753 (m, 1H), 1.230 (d, J=5.7 Hz, 6H)

Example 93

Preparation of Derivative 93 According to the Present Invention

Derivative 93 having the following formula was prepared as follows.

[Formula of Derivative 93]

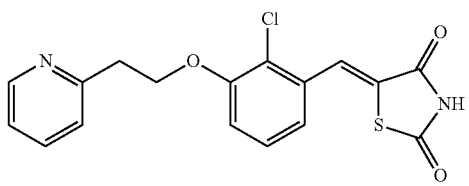 [SMILES: O=C1NC(=O)/C(=C/c2cccc(OCCc3ccccn3)c2Cl)S1]

The intermediate product, 2-chloro-3-[2-(pyridine-2-yl)ethoxy]benzaldehyde, was prepared in accordance with the same method as described in Example 51, except that 2-pyridineethanol (1 g, 8.1 mmol) and 2-chloro-3-hydroxybenzaldehyde (1.27 g, 8.1 mmol) were used in place of cyclohexanmethanol and 4-hydroxy-3-methylbenzaldehyde, respectively, and 2.33 g of triphenylphosphine (8.9 mmol) was used (1.74 g, yield: 82.1%).

Then, Derivative 93 having the above formula, 5-{(2-chloro-3-[2-(pyridin-2-yl)ethoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.11 g, yield: 80.4%).

$^1$H NMR (300 MHz, CDCl3) δ 8.558 (s, J=3.9 Hz, 1H), 8.203 (s, 1H), 7.659 (t, J=7.8 Hz, 1H), 7.151-7.210 (m, 3H), 7.113 (d, J=8.1 Hz, 2H), 4.199 (t, J=14.7 Hz, 2H), 3.199 (t, J=14.7 Hz, 2H)

Example 94

Preparation of Derivative 94 According to the Present Invention

Derivative 94 having the following formula was prepared as follows.

[Formula of Derivative 94]

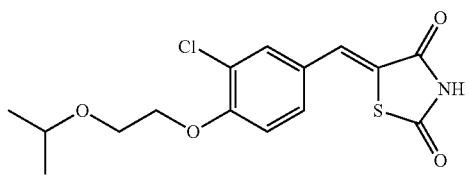 [SMILES: CC(C)OCCOc1ccc(/C=C2\SC(=O)NC2=O)cc1Cl]

The intermediate product, 3-chloro-4-[2-(propan-2-yloxy)ethoxy]benzaldehyde, was prepared in accordance with the same method as described in Example 51, except that 2-isopropoxyethanol (1 g, 9.6 mmol) and 3-chloro-4-hydroxybenzaldehyde (1.50 g, 9.6 mmol) were used in place of cyclohexanmethanol and 4-hydroxy-3-methylbenzaldehyde, respectively, and 2.77 g of triphenylphosphine (10.56 mmol) was used (1.54 g, yield: 71.5%).

Then, Derivative 94 having the above formula, 5-{3-chloro-4-[2-(propan-2-yloxy)ethoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.09 g, yield: 77.3%).

$^1$H NMR (300 MHz, CDCl3) δ 7.607 (s, 1H), 7.507 (s, 1H), 7.373 (d, J=8.4 Hz, 1H), 7.052 (d, J=8.4 Hz, 1H), 4.255 (t, J=10.2 Hz, 2H), 3.881 (t, J=10.2 Hz, 2H), 1.216 (d, J=3.9 Hz, 6H)

Example 95

Preparation of Derivative 95 According to the Present Invention

Derivative 95 having the following formula was prepared as follows.

[Formula of Derivative 95]

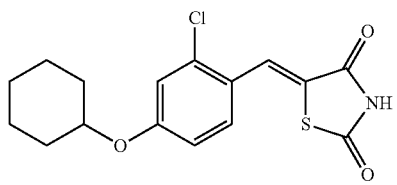 [SMILES: O=C1NC(=O)/C(=C/c2ccc(OC3CCCCC3)cc2Cl)S1]

The intermediate product, 2-chloro-4-(cyclohexyloxy)benzaldehyde, was prepared in accordance with the same method as described in Example 85, except that cyclohexanol (1 g, 10 mmol) was used in place of benzylalcohol (1 g, 9.2 mmol) (1.74 g, yield: 86%).

Then, Derivative 95 having the above formula, 5-(2-chloro-4-(cyclohexyloxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.01 g, yield: 71.1%).

$^1$H NMR (300 MHz, DMSO-d6) δ 10.581 (s, 1H), 7.658 (s, 1H), 7.529 (s, 1H), 7.398 (d, J=8.4 Hz, 1H), 7.273 (d, J=8.4 Hz, 1H), 1.451-1.465 (m, 11H)

Example 96

Preparation of Derivative 96 According to the Present Invention

Derivative 96 having the following formula was prepared as follows.

[Formula of Derivative 96]

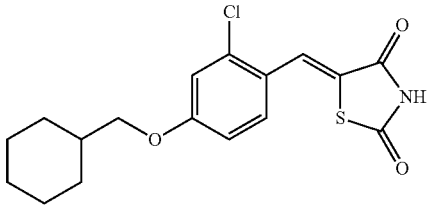 [SMILES: O=C1NC(=O)/C(=C/c2ccc(OCC3CCCCC3)cc2Cl)S1]

The intermediate product, 2-chloro-4-(3-cyclohexylmethoxy)benzaldehyde, was prepared in accordance with the same method as described in Example 85, except that cyclohexanemethanol (1 g, 9.2 mmol) was used in place of benzylalcohol (1 g, 9.2 mmol) (1.67 g, yield: 85%).

Then, Derivative 96 having the above formula, 5-(2-chloro-4-(3-cyclohexylmethoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.05 g, yield: 75.5%).

$^1$H NMR (300 MHz, DMSO-d6) δ 12.637 (s, 1H), 7.838 (s, 1H), 7.656 (d, J=8.7 Hz, 1H), 7.223 (s, 1H), 7.110 (d, J=8.7

Hz, 1H), 3.881 (d, J=6.0 Hz, 2H), 1.641-1.797 (m, 6H), 1.194-1.263 (m, 3H), 1.002-1.039 (m, 2H)

Example 97

Preparation of Derivative 97 According to the Present Invention

Derivative 97 having the following formula was prepared as follows.

[Formula of Derivative 97]

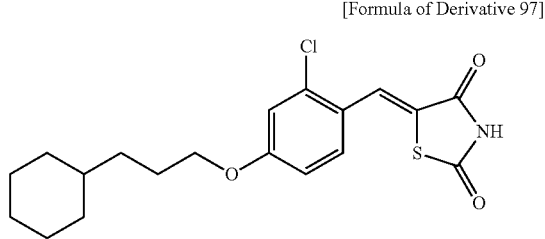

The intermediate product, 2-chloro-4-(3-cyclohexylpropoxy)benzaldehyde, was prepared in accordance with the same method as described in Example 85, except that 3-cyclohexyl-1-propanol (1 g, 7.0 mmol) was used in place of benzylalcohol (1 g, 9.2 mmol) (1.60 g, yield: 81.2%).

Then, Derivative 97 having the above formula, 5-(2-chloro-4-(3-cyclohexylpropoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (0.98 g, yield: 72.6%).

$^1$H NMR (300 MHz, DMSO-d6) δ 7.785 (s, 1H), 7.439 (s, 1H), 7.654 (d, J=11.7 Hz, 1H), 7.515 (d, J=11.7 Hz, 1H), 3.014 (t, J=7.2 Hz, 2H), 1.135-1.642 (m, 4H), 1.029-1.222 (m, 7H), 0.822-1.127 (m, 4H)

Example 98

Preparation of Derivative 98 According to the Present Invention

Derivative 98 having the following formula was prepared as follows.

[Formula of Derivative 98]

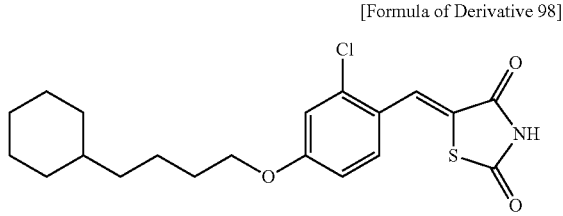

The intermediate product, 2-chloro-4-(3-cyclohexylbutoxy)benzaldehyde, was prepared in accordance with the same method as described in Example 85, except that 4-cyclohexyl-1-butanol (1 g, 6.4 mmol) was used in place of benzylalcohol (1 g, 9.2 mmol) (1.56 g, yield: 83%).

Then, Derivative 98 having the above formula, 5-(2-chloro-4-(3-cyclohexylbutoxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.02 g, yield: 76%).

$^1$H NMR (300 MHz, DMSO-d6) δ 12.649 (s, 1H), 7.880 (s, 1H), 7.497 (s, 1H), 7.497 (d, J=9.3 Hz, 1H), 7.515 (d, J=9.3 Hz, 1H), 3.014 (t, J=7.2 Hz, 2H), 1.653-1.724 (m, 4H), 1.315-1.642 (m, 4H), 1.069-1.215 (m, 7H), 0.820-0.852 (m, 2H)

Example 99

Preparation of Derivative 99 According to the Present Invention

Derivative 99 having the following formula was prepared as follows.

[Formula of Derivative 99]

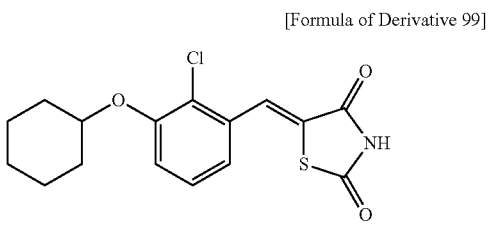

The intermediate product, 2-chloro-3-(cyclohexyloxy)benzaldehyde, was prepared in accordance with the same method as described in Example 51, except that cyclohexanol (1 g, 10 mmol) and 2-chloro-3-hydroxybenzaldehyde (1.57 g, 10 mmol) were used in place of cyclohexanemethanol and 4-hydroxy-3-methylbenzaldehyde, respectively, and 2.89 g of triphenylphosphine (11 mmol) was used (1.69 g, yield: 71%).

Then, Derivative 99 having the above formula, 5-(2-chloro-3-(cyclohexyloxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.12 g, yield: 78.9%).

$^1$H NMR (300 MHz, DMSO-d6) δ 12.587 (s, 1H), 7.724 (s, 1H), 7.524 (d, J=9.3 Hz, 1H), 7.315 (t, 1H), 7.195 (d, J=9.3 Hz, 1H), 4.310-4.389 (m, 1H), 1.933-2.044 (m, 2H), 1.734-1.822 (m, 2H), 1.491-1.674 (m, 2H), 1.208-1.446 (m, 2H), 0.860-0.946 (m, 2H)

Example 100

Preparation of Derivative 100 According to the Present Invention

Derivative 100 having the following formula was prepared as follows.

[Formula of Derivative 100]

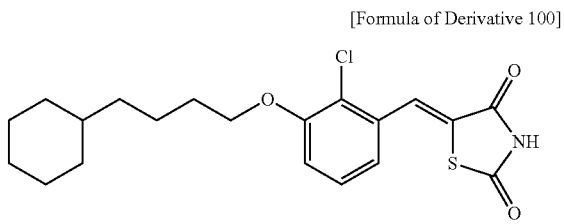

The intermediate product, 2-chloro-3-(cyclohexylbutoxy)benzaldehyde, was prepared in accordance with the same method as described in Example 51, except that 4-cyclohexyl-1-butanol (1 g, 6.4 mmol) and 2-chloro-3-hydroxybenzaldehyde (1.0 g, 6.4 mmol) were used in place of cyclohexanemethanol and 4-hydroxy-3-methylbenzaldehyde, respectively, and 1.85 g of triphenylphosphine (7.04 mmol) was used (1.49 g, yield: 79.3%).

Then, Derivative 100 having the above formula, 5-(2-chloro-3-(cyclohexylbutoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.12 g, yield: 83.6%).

$^1$H NMR (300 MHz, DMSO-d6) δ 7.894 (s, 1H), 7.496 (d, J=9.3 Hz, 1H), 7.264-7.342 (m, 1H), 7.203 (d, J=9.3 Hz, 1H), 4.103 (t, J=13.2 Hz, 2H), 1.839-1.913 (m, 2H), 1.569-1.726 (m, 5H), 1.089-1.436 (m, 8H), 0.912-0.998 (m, 2H)

Example 101

Preparation of Derivative 101 According to the Present Invention

Derivative 101 having the following formula was prepared as follows.

[Formula of Derivative 101]

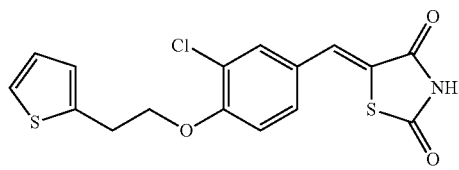 [SMILES: O=C1NC(=O)/C(=C/c2ccc(OCCc3cccs3)c(Cl)c2)S1]

The intermediate product, 3-chloro-4-(2-(thiophen-2-yl)ethoxy)benzaldehyde, was prepared in accordance with the same method as described in Example 51, except that 2-thiopheneethanol (1 g, 7.8 mmol) and 3-chloro-4-hydroxybenzaldehyde (1.22 g, 7.8 mmol) were used in place of cyclohexanemethanol and 4-hydroxy-3-methylbenzaldehyde, respectively, and 2.25 g of triphenylphosphine (8.58 mmol) was used (1.56 g, yield: 75%).

Then, Derivative 101 having the above formula, 5-(3-chloro-4-(2-(thiophen-2-yl)ethoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.21 g, yield: 88.3%).

$^1$H NMR (300 MHz, DMSO-d6) δ 12.585 (s, 1H), 7.725 (s, 1H), 7.708 (d, J=2.4 Hz, 1H), 7.536 (d, J=11.1 Hz, 1H), 7.315-7.363 (m, 2H), 7.017 (d, J=3.3 Hz, 1H), 6.978 (d, J=8.4 Hz, 1H), 4.354 (t, J=12.6 Hz, 2H), 3.322 (t, J=12.6 Hz, 2H)

Example 102

Preparation of Derivative 102 According to the Present Invention

Derivative 102 having the following formula was prepared as follows.

[Formula of Derivative 102]

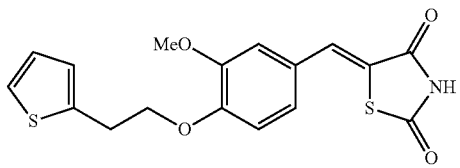 [SMILES: COc1cc(/C=C2\SC(=O)NC2=O)ccc1OCCc1cccs1]

The intermediate product, 3-methoxy-4-(2-(thiophen-2-yl)ethoxy)benzaldehyde, was prepared in accordance with the same method as described in Example 51, except that 2-thiopheneethanol (1 g, 7.8 mmol) and 4-hydroxy-3-methoxybenzaldehyde (1.19 g, 7.8 mmol) were used in place of cyclohexanemethanol and 4-hydroxy-3-methylbenzaldehyde, respectively, and 2.25 g of triphenylphosphine (8.58 mmol) was used (1.62 g, yield: 79.4%).

Then, Derivative 102 having the above formula, 5-(3-methoxy-4-(2-(thiophen-2-yl)ethoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.22 g, yield: 88.4%).

$^1$H NMR (300 MHz, DMSO-d6) δ 12.438 (s, 1H), 7.722 (s, 1H), 7.357 (d, J=6.6 Hz, 1H), 7.239 (s, 1H), 7.197 (d, J=14.4 Hz, 2H), 6.946-6.994 (m, 2H), 4.265 (t, J=6.6 Hz, 2H), 3.803 (s, 3H), 3.269 (t, J=6.6 Hz, 2H)

Example 103

Preparation of Derivative 103 According to the Present Invention

Derivative 103 having the following formula was prepared as follows.

[Formula of Derivative 103]

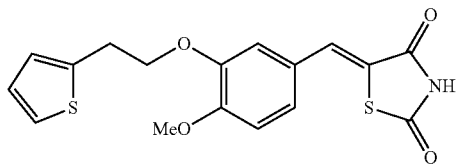 [SMILES: COc1ccc(/C=C2\SC(=O)NC2=O)cc1OCCc1cccs1]

The intermediate product, 4-methoxy-3-(2-(thiophen-2-yl)ethoxy)benzaldehyde, was prepared in accordance with the same method as described in Example 51, except that 2-thiopheneethanol (1 g, 7.8 mmol) and isovanillin (1.19 g, 7.8 mmol) were used in place of cyclohexanemethanol and 4-hydroxy-3-methylbenzaldehyde, respectively, and 2.25 g of triphenylphosphine (8.58 mmol) was used (1.60 g, yield: 79.2%).

Then, Derivative 103 having the above formula, 5-(4-methoxy-3-(2-(thiophen-2-yl)ethoxy)benzylidene)thiazolidine-2,4-dione, was obtained in accordance with the same method as described in Step 2 of Example 51, except that 4-(2-cyclomethoxy)-3-methylbenzaldehyde was replaced by the intermediate obtained in the above (1.26 g, yield: 91.3%).

$^1$H NMR (300 MHz, DMSO-d6) δ 7.706 (s, 1H), 7.361 (d, J=6.3 Hz, 1H), 7.232 d (d, J=1.8 Hz, 1H), 7.171 (d, J=1.8 Hz, 1H), 7.112 (s, 1H), 6.952-6.994 (m, 2H), 4.237 (t, J=13.2 Hz, 2H), 3.822 (s, 3H), 3.294 (t, J=13.2 Hz, 2H)

Example 104

Preparation of Derivative 104 According to the Present Invention

Derivative 104 having the following formula was prepared as follows.

[Formula of Derivative 104]

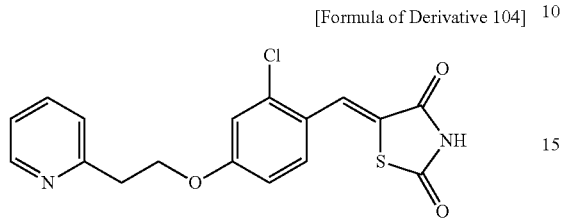

The intermediate product, 2-chloro-3-[2-(pyridine-2-yl)ethoxy]benzaldehyde, was prepared in accordance with the same method as described in Example 51, except that 2-pyridineethanol (1 g, 8.1 mmol) was used in place of benzylalcohol (1 g, 9.2 mmol) (1.42 g, yield: 67%).

Then, Derivative 104 having the above formula, 5-{(2-chloro-3-[2-(pyridin-2-yl)ethoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.1 g, yield: 79.7%).

$^1$H NMR (300 MHz, DMSO-d6) δ 8.461 (s, 1H), 7.966 (s, 1H), 7.722 (t, J=13.8 Hz, 1H), 6.836-7.291 (m, 6H), 4.008 (d, J=2.7 Hz, 2H), 2.982-3.033 (m, 2H), 1.185 (t, J=13.8 Hz, 2H)

Example 105

Preparation of Derivative 105 According to the Present Invention

Derivative 105 having the following formula was prepared as follows.

[Formula of Derivative 105]

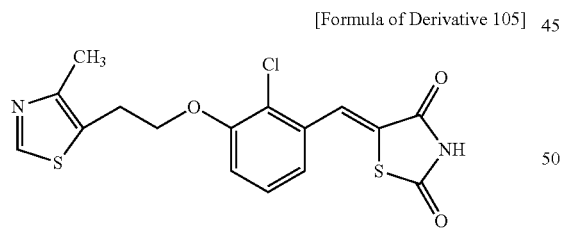

The intermediate product, 2-chloro-3-[2-(4-methyl-1,3-thiazolidin-5-yl)ethoxy]benzaldehyde, was prepared in accordance with the same method as described in Example 51, except that 5-(2-hydroxyethyl)-4-methylthiazole (1 g, 7.0 mmol) and 2-chloro-3-hydroxybenzaldehyde (1.1 g, 7.0 mmol) were used in place of cyclohexanemethanol and 4-hydroxy-3-methylbenzaldehyde, respectively, and 2.02 g of triphenylphosphine (7.7 mmol) was used (1.43 g, yield: 77%).

Then, Derivative 105 having the above formula, 5-{2-chloro-3-[2-(4-methyl-1,3-thiazolidin-5-yl)ethoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.16 g, yield: 85.9%).

$^1$H NMR (300 MHz, DMSO-d6) δ 12.726 (s, 1H), 8.826 (s, 1H), 7.909 (s, 1H), 7.466 (t, J=16.2 Hz, 1H), 7.273 (d, J=7.8 Hz, 1H), 7.162 (d, J=7.8 Hz, 1H), 4.284 (t, J=12 Hz, 2H), 3.289 (t, J=12 Hz, 2H), 2.287 (s, 3H)

Example 106

Preparation of Derivative 106 According to the Present Invention

Derivative 106 having the following formula was prepared as follows.

[Formula of Derivative 106]

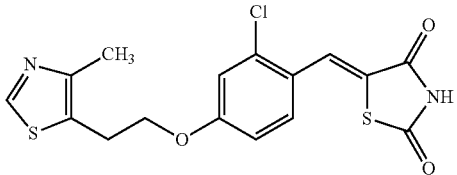 [SMILES: Cc1ncsc1CCOc1ccc(/C=C2\SC(=O)NC2=O)c(Cl)c1]

The intermediate product, 3-chloro-4-[2-(4-methyl-1,3-thiazolidin-5-yl)ethoxy]benzaldehyde, was prepared in accordance with the same method as described in Example 51, except that 5-(2-hydroxyethyl)-4-methylthiazole (1 g, 7.0 mmol) and 3-chloro-4-hydroxybenzaldehyde (1.1 g, 7.0 mmol) were used in place of cyclohexanmethanol and 4-hydroxy-3-methylbenzaldehyde, respectively, and 2.02 g of triphenylphosphine (7.7 mmol) was used (1.52 g, yield: 77.6%).

Then, Derivative 106 having the above formula, 5-{3-chloro-4-[2-(4-methyl-1,3-thiazolidin-5-yl)ethoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.14 g, yield: 84.4%).

$^1$H NMR (300 MHz, DMSO-d6) δ 12.586 (s, 1H), 8.832 (s, 1H), 7.724 (s, 1H), 7.697 (s, 1H), 7.532 (d, J=9.0 Hz, 1H), 7.320 (d, J=9.0 Hz, 1H), 4.318 (t, J=11.7 Hz, 2H), 3.274 (t, J=11.7 Hz, 2H), 2.359 (s, 3H)

Example 107

Preparation of Derivative 107 According to the Present Invention

Derivative 107 having the following formula was prepared as follows.

[Formula of Derivative 107]

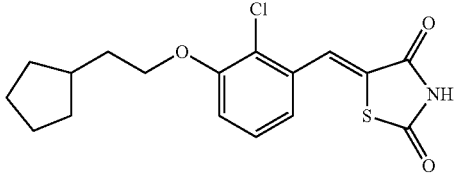 [SMILES: O=C1NC(=O)/C(=C/c2cccc(OCCC3CCCC3)c2Cl)S1]

The intermediate product, 2-chloro-3-(2-cyclopentylethoxy)benzaldehyde, was prepared in accordance with the same method as described in Example 51, except that cyclopentaneethanol (1 g, 8.8 mmol) and 2-chloro-3-hydroxybenzaldehyde (1.38 g, 8.8 mmol) were used in place of cyclohexanmethanol and 4-hydroxy-3-methylbenzaldehyde, respectively, and 2.57 of triphenylphosphine (9.8 mmol) was used (1.75 g, yield: 79.2%).

Then, Derivative 107 having the above formula, 5-[2-chloro-3-(2-cyclopentylethoxy)benzylidene]-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.21 g, yield: 87.1%).

$^1$H NMR (300 MHz, DMSO-d6) δ 12.992 (s, 1H), 8.192 (s, 1H), 7.729 (t, J=15.9 Hz, 1H), 7.545 (d, J=12.6 Hz, 1H), 7.373 (d, J=12.9 Hz, 1H), 4.382 (t, J=12.9 Hz, 2H), 1.705-2.225 (m, 9H), 1.399-1.473 (m, 2H)

Example 108

Preparation of Derivative 108 According to the Present Invention

Derivative 108 having the following formula was prepared as follows.

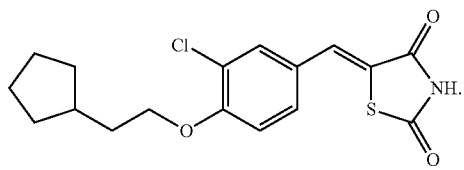

[Formula of Derivative 108]

The intermediate product, 3-chloro-4-(2-cyclopentylethoxy)benzaldehyde, was prepared in accordance with the same method as described in Example 51, except that cyclopentaneethanol (1 g, 8.8 mmol) and 3-chloro-4-hydroxybenzaldehyde (1.38 g, 8.8 mmol) were used in place of cyclohexanemethanol and 4-hydroxy-3-methylbenzaldehyde, respectively, and 2.57 g of triphenylphosphine (9.8 mmol) was used (1.8 g, yield: 81.5%).

Then, Derivative 108 having the above formula, 5-[3-chloro-4-(2-cyclopentylethoxy)benzylidene]-1,3-thiazolidine-2,4-dione, was obtained in accordance with the same method as described in Step 2 of Example 51, except that 4-(2-cyclomethoxy)-3-methylbenzaldehyde was replaced by the intermediate obtained in the above (1.185 g, yield: 84.9%).

$^1$H NMR (300 MHz, DMSO-d6) δ 12.992 (s, 1H), 7.720 (s, 1H), 7.689 (s, 1H), 7.545 (d, J=11.1 Hz, 1H), 7.317 (d, J=8.7 Hz, 1H), 4.161 (t, J=13.2 Hz, 2H), 1.189-1.921 (m, 9H), 1.053-1.212 (m, 2H)

Example 109

Preparation of Derivative 109 According to the Present Invention

Derivative 109 having the following formula was prepared as follows.

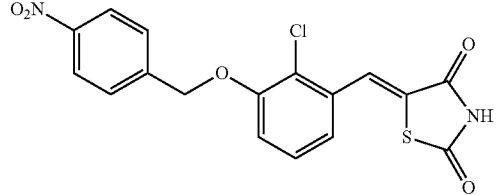 [SMILES: O=C1NC(=O)/C(=C/c2cccc(OCc3ccc([N+](=O)[O-])cc3)c2Cl)S1]

[Formula of Derivative 109]

The intermediate product, 2-chloro-3-(4-nitrobenzyloxy)benzaldehyde, was prepared in accordance with the same method as described in Example 51, except that 4-nitrobenzyl alcohol (1 g, 6.5 mmol) and 2-chloro-3-hydroxybenzaldehyde (1.02 g, 6.5 mmol) were used in place of cyclohexanemethanol and 4-hydroxy-3-methylbenzaldehyde, respectively, and 1.88 g of triphenylphosphine (7.15 mmol) was used (1.56 g, yield: 82.1%).

Then, Derivative 109 having the above formula, 5-(2-chloro-3-(4-nitrobenzyloxy)benzylidene)thiazolidine-2,4-dione, was obtained in accordance with the same method as described in Step of Example 51, except that 4-(2-cyclomethoxy)-3-methylbenzaldehyde was replaced by the intermediate obtained in the above (1.05 g, yield: 78.4%).

$^1$H NMR (300 MHz, DMSO-d6) δ 8.405 (s, 1H), 8.300 (d, J=9 Hz, 2H), 7.763 (d, J=9 Hz, 2H), 7.451 (t, J=8.1 Hz, 1H), 7.249 (t, J=7.5 Hz, 2H), 5.419 (s, 2H)

Example 110

Preparation of Derivative 110 According to the Present Invention

Derivative 110 having the following formula was prepared as follows.

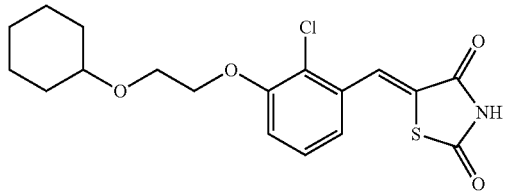 [SMILES: O=C1NC(=O)/C(=C/c2cccc(OCCOC3CCCCC3)c2Cl)S1]

[Formula of Derivative 110]

The intermediate product, 2-chloro-3-[2-cyclohexyloxy)ethoxy]benzaldehyde, was prepared in accordance with the same method as described in Example 51, except that 2-(cyclohexyloxy)ethanol (1 g, 6.9 mmol) and 2-chloro-3-hydroxybenzaldehyde (1.08 g, 6.9 mmol) were used in place of cyclohexanemethanol and 4-hydroxy-3-methylbenzaldehyde, and 1.99 of triphenylphosphine (7.59 mmol) was used (1.48 g, yield: 74.4%).

Then, Derivative 110 having the above formula, 5-{2-chloro-3-[2-(cyclohexyloxy)ethoxy]benzylidene}-1,3-thiazolidine-2,4-dione, was obtained in accordance with the same method as described in Step 2 of Example 51, except that 4-(2-cyclomethoxy)-3-methylbenzaldehyde was replaced by the intermediate product obtained in the above (1.15 g, yield: 85.2%).

$^1$H NMR (300 MHz, DMSO-d6) δ 7.922 (s, 1H), 7.468 (t, J=15.9 Hz, 1H), 7.298 (d, J=7.5 Hz, 1H), 7.160 (d, J=8.1 Hz,

1H), 4.212 (t, J=9 Hz, 2H), 4.051 (q, 1H), 3.775 (t, J=9 Hz, 2H), 1.63-1.647 (m, 3H), 1.630-1.647 (m, 3H), 1.138-1.464 (m, 4H)

Example 111

Preparation of Derivative 111 According to the Present Invention

Derivative 111 having the following formula was prepared as follows.

[Formula of Derivative 111]

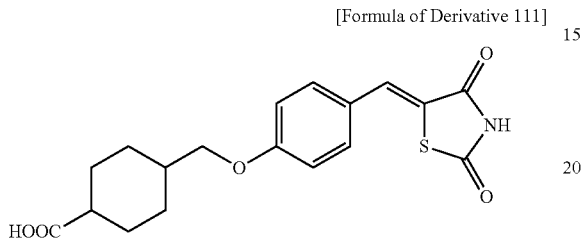

To 30 ml of methanol in which methyl-4-((4-((2,4-dioxothiazolidine-5-ylidene)methyl)phenoxy)methyl)cyclohexane carboxylate prepared in Example 66 was dissolved, 2N KOH (30 ml) was added while stirring. The mixture was stirred for 1 hour under reflux, then diluted with water and acidified by HCl. Subsequently, the precipitate thus formed was washed with water and dried to afford 4-({4-[(Z)-(2,4-dioxo-1,3-thiazolidin-5-ylidene)methyl]phenoxy}methyl) cyclohexane carboxylic acid (Derivative 111 having the above formula) as white solid (0.74 g, yield: 77.1%).

$^1$H NMR (300 MHz, DMSO-d6) δ 1.947 (s, 1H), 7.427 (d, J=8.7 Hz, 2H), 7.206 (s, 1H), 6.974 (d, J=8.7 Hz, 2H), 3.790 (d, J=6.9 Hz, 2H), 2.478-2.502 (m, 2H), 1.904-1.918 (m, 4H), 1.461-1.639 (m, 1H), 1.329-1.461 (m, 3H)

Example 112

Preparation of Derivative 112 According to the Present Invention

Derivative 112 having the following formula was prepared as follows.

[Formula of Derivative 112]

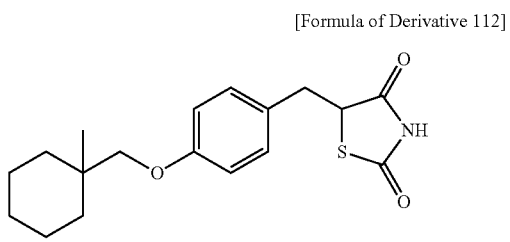

To the suspension containing CoCl$_2$.6H$_2$O (4.5 mg, 0.016 mmol) and dimethylglyoxime (70.1 mg, 0.6 mmol) in 10 ml of water, 4 drops of 1.0N NaOH and NaBH$_4$ (384.6 mg, 10 mmol) were subsequently added. The mixture was cooled to 0° C., and 5-(4-((1-methylcyclohexyl)methoxy)benzylidene) thiazolidine-2,4-dione (1 g, 3.0 mmol) in 15 ml of THF-DMF (2:1) was then added thereto over 20 minutes. The mixture was stirred at room temperature for 18 hours, to which acetic acid was then added until the pH thereof reached about 6. The mixture was diluted with water, and extracted with ethyl acetate and water. The organic layer was washed with water several times, dried with anhydrous magnesium sulfate, filtered and solvent-evaporated. The residual oil was chromatographed on silica gel to afford 5-(4-((1-methylcyclohexyl) methoxy)benzyl)thiazolidine-2,4-dione (Derivative 112 of the above formula) as white solid (0.8 g, yield: 80%).

Example 113

Preparation of Derivative 113 According to the Present Invention

Derivative 113 having the following formula was prepared as follows.

[Formula of Derivative 113]

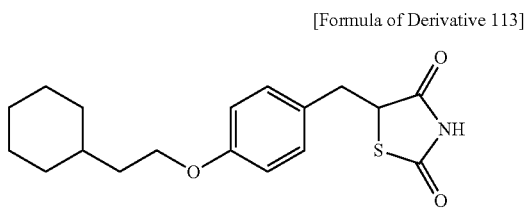

To the suspension containing CoCl$_2$.6H$_2$O (4.5 mg, 0.016 mmol) and dimethylglyoxime (70.1 mg, 0.6 mmol) in 10 ml of water, 4 drops of 1.0N NaOH and NaBH$_4$ (384.6 mg, 10 mmol) were subsequently added. The mixture was cooled to 0° C., and 5-(4-(2-cyclohexylethoxy)benzylidene)thiazolidine-2,4-dione (1 g, 3.02 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(4-(2-cyclohexylethoxy)benzyl)thiazolidine-2,4-dione (Derivative 113 of the above formula) as white solid (0.8 g, yield: 79%).

$^1$H NMR (300 MHz, DMSO-d6): δ 11.998 (s, 1H) 7.135 (d, J=7.5 Hz, 2H), 6.861 (d, J=7.8 Hz, 2H), 4.870 (dd, J=3.3, 3.3 Hz, 1H), 3.966 (t, J=12.9 Hz, 2H), 3.35 (dd, J=4.5, 4.5 Hz, 1H), 3.07 (dd, J=9.0, 9.0 Hz, 1H), 1.548-1.615 (m, 7H), 1.433-1.548 (m, 1H), 1.097-1.261 (m, 3H), 0.869-0.977 (m, 2H)

Example 114

Preparation of Derivative 114 According to the Present Invention

Derivative 114 having the following formula was prepared as follows.

[Formula of Derivative 114]

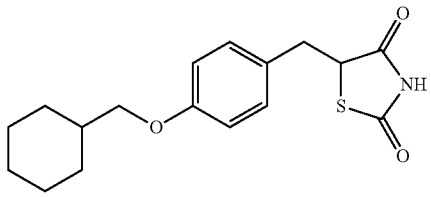 [SMILES: O=C1NC(=O)C(Cc2ccc(OCC3CCCCC3)cc2)S1]

To the suspension containing CoCl$_2$.6H$_2$O (4.4 mg, 0.016 mmol) and dimethylglyoxime (73.1 mg, 0.58 mmol) in 10 ml of water, 4 drops of 1.0N NaOH and NaBH$_4$ (409.3 mg, 10.6 mmol) were subsequently added. The mixture was cooled to 0° C., and 5-(4-(cyclohexylmethoxy)benzylidene)thiazolidine-2,4-dione (1 g, 3.13 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(4-(cyclohexylmethoxy)benzyl)thiazolidine-2,4-dione (Derivative 114 of the above formula) as white solid (0.8 g, yield: 79%).

$^1$H NMR (300 MHz, DMSO-d6): δ 7.816 (s, 1H), 7.145 (d, J=8.7 Hz, 2H), 6.854 (d, J=8.7 Hz, 2H), 4.528 (dd, J=3.6, 3.6 Hz, 1H), 3.740 (d, J=6.6 Hz, 2H), 3.486 (dd, J=4.2, 4.2 Hz, 1H), 3.138 (dd, J=9.6, 9.6 Hz, 1H), 1.604-1.882 (m, 6H), 1.212-1.426 (m, 3H), 0.884-1.131 (m, 2H)

Example 115

Preparation of Derivative 115 According to the Present Invention

Derivative 115 having the following formula was prepared as follows.

[Formula of Derivative 115]

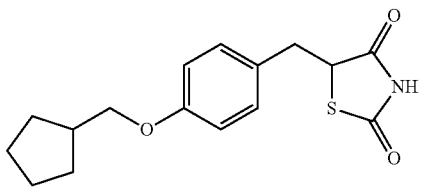 [SMILES: O=C1NC(=O)C(Cc2ccc(OCC3CCCC3)cc2)S1]

To the suspension containing CoCl$_2$.6H$_2$O (4.6 mg, 0.016 mmol) and dimethylglyoxime (76.4 mg, 0.65 mmol) in 10 ml of water, 4 drops of 1.0N NaOH and NaBH$_4$ (427.6 mg, 11.12 mmol) were subsequently added. The mixture was cooled to 0° C., and 5-(4-(cyclopentylmethoxy)benzylidene)thiazolidine-2,4-dione (1 g, 3.27 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(4-(cyclopentylmethoxy)benzyl)thiazolidine-2,4-dione (Derivative 115 of the above formula) as white solid (0.8 g, yield: 79%).

$^1$H NMR (300 MHz, DMSO-d6): δ 7.842 (s, 1H), 7.146 (d, J=8.7 Hz, 2H), 6.874 (d, J=8.7 Hz, 2H), 4.531 (dd, J=4.2, 4.2 Hz, 1H), 3.819 (d, J=6.9 Hz, 2H), 3.482 (dd, J=4.2, 4.2 Hz, 1H), 3.145 (dd, J=9.3, 9.3 Hz, 1H), 2.054-2.402 (m, 1H), 1.799-1.867 (m, 2H), 1.565-1.646 (m, 4H), 1.319-1.384 (m, 2H)

Example 116

Preparation of Derivative 116 According to the Present Invention

Derivative 116 having the following formula was prepared as follows.

[Formula of Derivative 116]

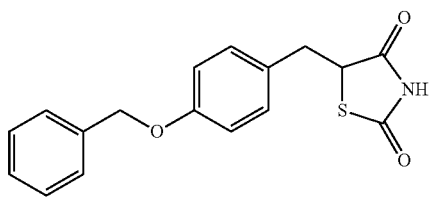 [SMILES: O=C1NC(=O)C(Cc2ccc(OCc3ccccc3)cc2)S1]

To the suspension containing CoCl$_2$.6H$_2$O (4.49 mg, 0.016 mmol) and dimethylglyoxime (74.54 mg, 0.64 mmol) in 10 ml of water, 4 drops of 1.0N NaOH and NaBH$_4$ (417.1 mg, 10.85 mmol) were subsequently added. The mixture was cooled to 0° C., and 5-(4-(benzyloxy)benzylidene)thiazolidine-2,4-dione (1 g, 3.27 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(4-(benzyloxy)benzyl)thiazolidine-2,4-dione (Derivative 116 of the above formula) as white solid (0.8 g, yield: 79%).

$^1$H NMR (300 MHz, DMSO-d6): δ 7.85 (s, 1H), 7.262-7.444 (m, 5H), 7.167 (d, J=8.7 Hz, 2H), 6.947 (d, J=8.7 Hz, 2H), 5.052 (s, 2H), 4.533 (dd, J=3.9, 3.9 Hz, 1H), 3.487 (dd, J=3.6, 3.6 Hz, 1H), 3.156 (dd, J=9.0, 9.0 Hz, 1H)

Example 117

Preparation of Derivative 117 According to the Present Invention

Derivative 117 having the following formula was prepared as follows.

[Formula of Derivative 117]

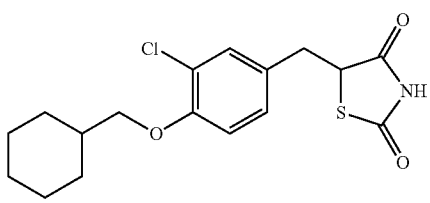 [SMILES: O=C1NC(=O)C(Cc2ccc(OCC3CCCCC3)c(Cl)c2)S1]

To the suspension containing CoCl$_2$.6H$_2$O (3.98 mg, 0.014 mmol) and dimethylglyoxime (66.13 mg, 0.57 mmol) in 10 ml of water, 4 drops of 1.0N NaOH and NaBH$_4$ (370.06 mg, 9.62 mmol) were subsequently added. The mixture was cooled to 0° C., and 5-(3-chloro-4-(cyclohexylmethoxy)benzylidene)thiazolidine-2,4-dione (1 g, 2.83 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(3-chloro-4-(cyclohexylmethoxy)benzyl)thiazolidine-2,4-dione (Derivative 117 of the above formula) as white solid (0.8 g, yield: 79%).

$^1$H NMR (300 MHz, DMSO-d6): δ 7.891 (s, 1H), 7.238 (s, 1H), 7.072 (d, J=10.8 Hz, 2H), 6.854 (d, J=10.8 Hz, 2H), 4.521 (dd, J=3.6, 3.6 Hz, 1H), 3.807 (d, J=6.3 Hz, 2H), 3.444 (dd, J=3.6, 3.6 Hz, 1H) 3.129 (dd, J=9.0, 9.0 Hz, 1H), 1.693-1.917 (m, 6H), 1.252-1.376 (m, 3H), 1.057-1.211 (m, 2H)

Example 118

Preparation of Derivative 118 According to the Present Invention

Derivative 118 having the following formula was prepared as follows.

[Formula of Derivative 118]

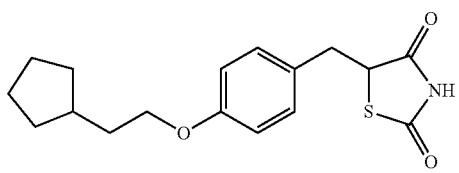

To the suspension containing CoCl$_2$.6H$_2$O (4.77 mg, 0.016 mmol) and dimethylglyoxime (73.14 mg, 0.63 mmol) in 10 ml of water, 4 drops of 1.0N NaOH and NaBH$_4$ (409.4 mg, 10.65 mmol) were subsequently added. The mixture was cooled to 0° C., and 5-(4-(2-cyclopentylethoxy)benzylidene)thiazolidine-2,4-dione (1 g, 3.13 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(4-(2-cyclopentylethoxy)benzyl)thiazolidine-2,4-dione (Derivative 118 of the above formula) as white solid (0.8 g, yield: 79%).

$^1$H NMR (300 MHz, DMSO-d6): δ 7.844 (s, 1H), 7.148 (d, J=8.4 Hz, 2H), 6.870 (d, J=8.4 Hz, 2H), 4.529 (dd, J=3.6, 3.6 Hz, 1H), 3.980 (t, J=13.5 Hz, 2H), 3.485 (dd, J=3.9, 3.9 Hz, 1H), 3.143 (dd, J=9.6, 9.6 Hz, 1H), 1.869-1.967 (m, 1H), 1.810-1.845 (m, 1H), 1.764-1.787 (t, J=13.5 Hz, 2H), 1.510-1.664 (m, 5H), 1.125-1.192 (m, 2H)

Example 119

Preparation of Derivative 119 According to the Present Invention

Derivative 119 having the following formula was prepared as follows.

[Formula of Derivative 119]

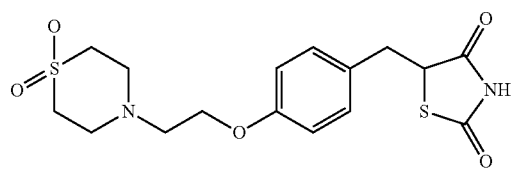

To the suspension containing CoCl$_2$.6H$_2$O (3.66 mg, 0.013 mmol) and dimethylglyoxime (60.75 mg, 0.52 mmol) in 10 ml of water, 4 drops of 1.0N NaOH and NaBH$_4$ (340.11 mg, 8.84 mmol) were subsequently added. The mixture was cooled to 0° C., and then 5-(4-(2-thiomorpholine-1,1-dioxideethoxy)benzylidene)-2,4-thiazolidinedione (1 g, 2.6 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(4-(2-thiomorpholine-1,1-dioxideethoxy)benzyl)-2,4-thiazolidinedione (Derivative 119 of the above formula) as white solid (0.8 g, yield: 79%).

$^1$H NMR (300 MHz, DMSO-d6): δ 12.308 (s, 1H), 7.568 (d, J=9.3 Hz, 2H), 6.893 (d, J=9.3 Hz, 2H), 4.887 (dd, J=4.2, 4.2 Hz, 1H), 4.183 (t, J=11.4 Hz, 2H), 4.069 (t, J=11.4 Hz, 2H), 3.095 (d, J=7.2 Hz, 4H), 3.039 (d, J=7.2 Hz, 4H), 2.957 (m, 2H)

Example 120

Preparation of Derivative 120 According to the Present Invention

Derivative 120 having the following formula was prepared as follows.

[Formula of Derivative 120]

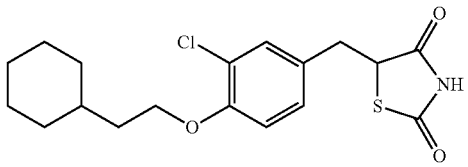

To the suspension containing $CoCl_2 \cdot 6H_2O$ (3.83 mg, 0.014 mmol) and dimethylglyoxime (63.56 mg, 0.54 mmol) in 10 ml of water, 4 drops of 1.0N NaOH and $NaBH_4$ (355.43 mg, 9.24 mmol) were subsequently added. The mixture was cooled to 0° C., and 5-(3-chloro-4-(2-cyclohexylethoxy)benzylidene)thiazolidine-2,4-dione (1 g, 2.72 mmol) in 15 ml of THF-DMF (2:1) was added thereto over 20 minutes. The mixture was stirred at room temperature for 18 hours, to which acetic acid was then added until the pH thereof reached about 6. The mixture was diluted with water and extracted with ethyl acetate and water. The organic layer was washed with water several times, dried with anhydrous magnesium sulfate, filtered and solvent-evaporated. The residual oil was chromatographed on silica gel to afford 5-(3-chloro-4-(2-cyclohexylethoxy)benzyl)thiazolidine-2,4-dione (Derivative 120 of the above formula) as white solid (0.8 g, yield: 79%).

$^1$H NMR (300 MHz, DMSO-d6): δ 7.900 (s, 1H), 7.242 (s, 1H), 7.078 (d, J=10.8 Hz, 2H), 6.913 (d, J=10.8 Hz, 2H), 4.523 (dd, J=3.9, 3.9 Hz, 1H), 4.068 (t, J=13.5 Hz, 2H), 3.447 (dd, J=4.2, 4.2 Hz, 1H), 3.134 (dd, J=9.3, 9.3 Hz, 1H), 1.689-1.793 (m, 7H), 1.504-1.572 (m, 1H), 1.144-1.329 (m, 3H), 0.926-1.037 (m, 2H)

Example 121

Preparation of Derivative 121 According to the Present Invention

Derivative 121 having the following formula was prepared as follows.

[Formula of Derivative 121]

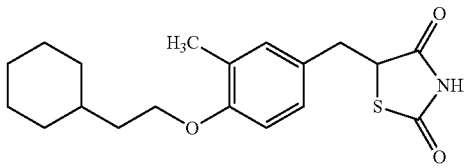

Derivative 121 having the above formula, 5-(4-(2-cyclohexylethoxy)-3-methylbenzyl)thiazolidine-2,4-dione, was obtained in accordance with the same method as described in Example 120, except that $CoCl_2 \cdot 6H_2O$ (4.32 mg, 0.015 mmol) and dimethylglyoxime (67.31 mg, 0.58 mmol) were used, and $NaBH_4$ (369.3 mg, 9.86 mmol) was added to obtain the mixture, to which 5-(4-(2-cyclohexylethoxy)-3-methylbenzylidene) thiazolidine-2,4-dione (1 g, 2.9 mmol) in 15 ml of THF-DMF (2:1) was added over 20 minutes (0.8 g, yield: 80%).

$^1$H NMR (300 MHz, CDCl3) δ7.89 (s, 1H), 7.346 (s, 1H), 7.124 (d, J=8.7 Hz, 1H), 7.006 (d, J=8.7 Hz, 1H), 4.623 (dd, J=3.9, 4.2 Hz, 1H), 4.268 (t, J=13.5 Hz, 2H), 3.549 (dd, J=4.2, 3.9 Hz, 1H), 3.244 (dd, J=9.6, 9.6 Hz, 1H), 2.206 (s, 3H), 1.598-1.693 (m, 6H), 1.526-1.548 (m, 1H), 1.269-1.304 (m, 4H), 0.838-0.987 (m, 2H)

Example 122

Preparation of Derivative 122 According to the Present Invention

Derivative 122 having the following formula was prepared as follows.

[Formula of Derivative 122]

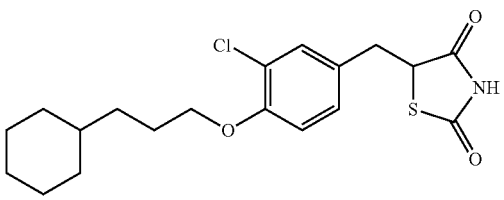

Derivative 122 having the above formula, 5-(3-chloro-4-(cyclohexylpropoxy)benzyl)thiazolidine-2,4-dione, was obtained in accordance with the same method as described in Example 120, except that $CoCl_2 \cdot 6H_2O$ (3.87 mg, 0.013 mmol) and dimethylglyoxime (60.35 mg, 0.52 mmol) were used, and $NaBH_4$ (331.11 mg, 8.84 mmol) was added to obtain the mixture, to which 5-(3-chloro-4-(cyclohexylpropoxy)benzylidene) thiazolidine-2,4-dione (1 g, 2.6 mmol) in 15 ml of THF-DMF (2:1) was added over 20 minutes (0.78 g, yield: 77.8%).

$^1$H NMR (300 MHz, CDCl3) δ 7.91 (s, 1H), 7.285 (s, 1H), 7.224 (d, J=8.4 Hz, 1H), 7.108 (d, J=8.4 Hz, 1H), 4.572 (dd, J=3.9, 4.2 Hz, 1H), 4.197 (t, J=12.6 Hz, 2H), 3.487 (dd, J=4.2, 3.9 Hz, 1H), 3.288 (dd, J=9.6, 9.6 Hz, 1H), 1.697-1.845 (m, 7H), 1.428-1.590 (m, 6H), 0.864-0.996 (m, 2H)

Example 123

Preparation of Derivative 123 According to the Present Invention

Derivative 123 having the following formula was prepared as follows.

[Formula of Derivative 123]

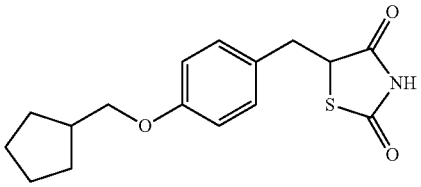

Derivative 123 having the above formula, 5-(4-(cyclopentylmethoxy)benzyl)thiazolidine-2,4-dione, was obtained in accordance with the same method as described in Example 120, except that $CoCl_2 \cdot 6H_2O$ (4.92 mg, 0.017 mmol) and dimethylglyoxime (76.60 mg, 0.66 mmol) were used, and $NaBH_4$ (420.3 mg, 11.22 mmol) was added to obtain the mixture, to which 5-(4-(cyclopentylmethoxy)benzylidene) thiazolidine-2,4-dione (1 g, 3.3 mmol) in 15 ml of THF-DMF (2:1) was added over 20 minutes (0.79 g, yield: 78.6%).

$^1$H NMR (300 MHz, CDCl3) δ 7.742 (s, 1H), 7.146 (d, J=8.7 Hz, 2H), 6.874 (d, J=8.7 Hz, 2H), 4.531 (dd, J=4.2, 4.2 Hz, 1H), 3.819 (d, J=6.9 Hz, 2H), 3.469 (dd, J=3.9, 3.6 Hz,

1H), 3.145 (dd, J=9.3, 9.6 Hz, 1H), 2.302-2.402 (m, 1H), 1.799-1.867 (m, 2H), 1.565-1.646 (m, 4H), 1.319-1.384 (m, 2H)

Example 124

Preparation of Derivative 124 According to the Present Invention

Derivative 124 having the following formula was prepared as follows.

[Formula of Derivative 124]

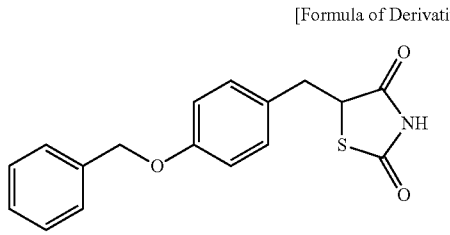

Derivative 124 having the above formula, 5-(4-(benzyloxy)benzyl)thiazolidine-2,4-dione, was obtained in accordance with the same method as described in Example 120, except that $CoCl_2.6H_2O$ (4.77 mg, 0.016 mmol) and dimethylglyoxime (74.29 mg, 0.64 mmol) were used, and $NaBH_4$ (407.5 mg, 10.88 mmol) was added to obtain the mixture, to which 5-(4-(benzyloxy)benzylidene)thiazolidine-2,4-dion (1 g, 3.2 mmol) in 15 ml of THF-DMF (2:1) was added over 20 minutes (0.83 g, yield: 82.5%).

$^1$H NMR (300 MHz, CDCl3) δ 7.444 (s, 1H), 7.308-7.418 (m, 5H), 7.167 (d, J=8.7 Hz, 2H), 6.947 (d, J=8.7 Hz, 2H), 5.052 (s, 2H), 4.533 (dd, J=3.9, 3.9 Hz, 1H), 3.487 (dd, J=3.6, 4.2 Hz, 1H), 3.156 (dd, J=9.0, 9.6 Hz, 1H)

Example 125

Preparation of Derivative 125 According to the Present Invention

Derivative 125 having the following formula was prepared as follows.

[Formula of Derivative 125]

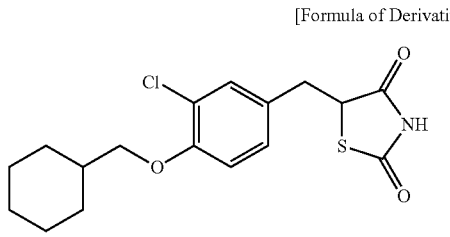

Derivative 125 having the above formula, 5-(3-chloro-4-(cyclohexylpropoxy)benzyl)thiazolidine-2,4-dione, was obtained in accordance with the same method as described in Example 120, except that $CoCl_2.6H_2O$ (4.17 mg, 0.014 mmol) and dimethylglyoxime (64.99 mg, 0.56 mmol) were used, and $NaBH_4$ (356.6 mg, 9.52 mmol) was added to obtain the mixture, to which 5-(3-chloro-4-(cyclohexylpropoxy)benzylidene)thiazolidine-2,4-dione (1 g, 2.8 mmol) in 15 ml of THF-DMF (2:1) was added over 20 minutes (0.83 g, yield: 82.5%).

$^1$H NMR (300 MHz, CDCl3) δ 7.891 (s, 1H), 7.238 (s, 1H), 7.072 (d, J=8.4 Hz, 1H), 6.858 (d, J=8.4 Hz, 1H), 4.521 (dd, J=3.6, 3.9 Hz, 1H), 3.807 (d, J=6.3 Hz, 2H), 3.444 (dd, J=3.6, 4.2 Hz, 1H), 3.129 (dd, J=9.0, 9.6 Hz, 1H), 1.693-1.917 (m, 6H), 1.057-1.376 (m, 5H)

Example 126

Preparation of Derivative 126 According to the Present Invention

Derivative 126 having the following formula was prepared as follows.

[Formula of Derivative 126]

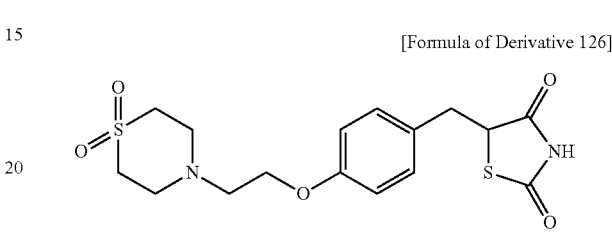

Derivative 126 having the above formula, 5-(4-(2-thiomorpholine-1,1-Dioxideethoxy)benzyl)-2,4-thiazolidinedione, was obtained in accordance with the same method as described in Example 120, except that $CoCl_2.6H_2O$ (3.87 mg, 0.013 mmol) and dimethylglyoxime (60.35 mg, 0.52 mmol) were used, $NaBH_4$ (331.1 mg, 8.84 mmol) was added to obtain the mixture, to which 5-(4-(2-thiomorpholine 1,1-Dioxideethoxy)benzylidene)-2,4-thiazolidinedione (1 g, 2.6 mmol) in 15 ml of THF-DMF (2:1) was added over 20 minutes (0.78 g, yield: 77.6%).

$^1$H NMR (300 MHz, CDCl3) δ 7.728 (s, 1H), 7.238 (s, 1H), 7.568 (d, J=9.3 Hz, 2H), 6.893 (d, J=9.3 Hz, 2H), 4.887 (dd, J=4.2, 4.2 Hz, 1H), 4.163 (t, J=11.4 Hz, 2H), 4.069 (t, J=11.4 Hz, 2H), 3.095 (m, 8H), 2.957 (m, 2H)

Example 127

Preparation of Derivative 127 According to the Present Invention

Derivative 127 having the following formula was prepared as follows.

[Formula of Derivative 127]

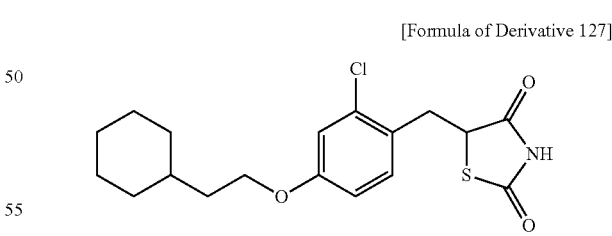

Derivative 127 having the above formula, 5-(2-chloro-4-(2-cyclohexylethoxy)benzyl)thiazolidine-2,4-dione, was obtained in accordance with the same method as described in Example 120, except that $CoCl_2.6H_2O$ (4.17 mg, 0.014 mmol) and dimethylglyoxime (64.99 mg, 0.56 mmol) were used, and $NaBH_4$ (356.6 mg, 9.52 mmol) was added to obtain the mixture, to which 5-(2-chloro-4-(2-cyclohexylethoxy)benzylidene)thiazolidine-2,4-dione (1 g, 2.7 mmol) in 15 ml of THF-DMF (2:1) was added over 20 minutes (0.82 g, yield: 81.6%).

$^1$H NMR (300 MHz, CDCl3) δ 7.891 (s, 1H), 7.249 (s, 1H), 7.106 (d, J=8.7 Hz, 1H), 6.958 (d, J=8.7 Hz, 1H), 4.531 (dd, J=3.6, 3.9 Hz, 1H), 3.917 (t, J=6.6 Hz, 2H), 3.354 (dd, J=3.6, 4.2 Hz, 1H), 3.239 (dd, J=9.0, 9.6 Hz, 1H), 2.062-2.149 (m, 2H), 1.793-1.827 (m, 6H), 1.052-1.216 (m, 5H)

Example 128

Preparation of Derivative 128 According to the Present Invention

Derivative 128 having the following formula was prepared as follows.

[Formula of Derivative 128]

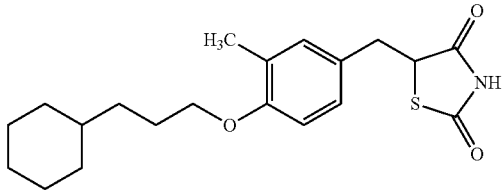

Derivative 128 having the above formula, 5-(4-(2-cyclohexylpropoxy)-3-methylbenzyl)thiazolidine-2,4-dione, was obtained in accordance with the same method as described in Example 120, except that CoCl$_2$.6H$_2$O (4.17 mg, 0.014 mmol) and dimethylglyoxime (64.99 mg, 0.56 mmol) were used, and NaBH$_4$ (356.6 mg, 9.52 mmol) was added to obtain the mixture, to which 5-(4-(2-cyclohexylpropoxy)-3-methylbenzylidene)thiazolidine-2,4-dione (1 g, 2.8 mmol) in 15 ml of THF-DMF (2:1) was added over 20 minutes (0.80 g, yield: 79.8%).

$^1$H NMR (300 MHz, CDCl3) δ 7.902 (s, 1H), 7.346 (s, 1H), 7.144 (d, J=8.7 Hz, 1H), 7.016 (d, J=8.7 Hz, 1H), 4.643 (dd, J=3.9, 3.9 Hz, 1H), 4.368 (t, J=13.5 Hz, 2H), 3.542 (dd, J=4.2, 4.2 Hz, 1H), 3.164 (dd, J=9.6, 9.6 Hz, 1H), 2.186 (s, 3H), 1.588-1.653 (m, 6H), 1.486-1.528 (m, 2H), 1.262-1.318 (m, 4H), 0.748-0.877 (m, 3H)

Example 129

Preparation of Derivative 129 According to the Present Invention

Derivative 129 having the following formula was prepared as follows.

[Formula of Derivative 129]

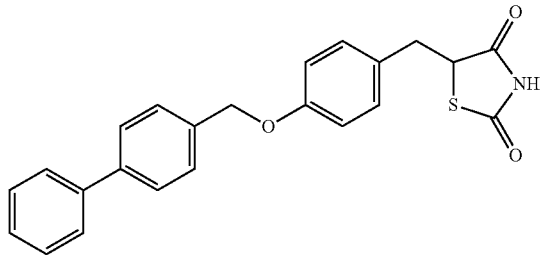

Derivative 129 having the above formula, 5-(4-(biphenyl-4-ylmethoxy)benzyl)thiazolidine-2,4-dione, was obtained in accordance with the same method as described in Example 120, except that CoCl$_2$.6H$_2$O (3.87 mg, 0.013 mmol) and dimethylglyoxime (60.35 mg, 0.52 mmol) were used, and NaBH$_4$ (331.1 mg, 8.84 mmol) was added to obtain the mixture, to which 5-(4-(biphenyl-4-ylmethoxy)benzylidene)thiazolidine-2,4-dione (1 g, 2.6 mmol) in 15 ml of THF-DMF (2:1) was added over 20 minutes (0.81 g, yield: 80.5%).

$^1$H NMR (300 MHz, CDCl3) δ 7.727 (s, 1H), 7.661-7.703 (m, 4H), 7.435-7.578 (m, 4H), 7.205-7.359 (m, 1H), 7.205 (d, J=8.7 Hz, 2H), 6.952 (d, J=8.7 Hz, 2H), 5.112 (s, 2H), 4.894 (dd, J=4.2, 4.2 Hz, 1H), 3.381 (dd, J=4.2, 4.2 Hz, 1H), 3.089 (dd, J=8.7, 9.3 Hz, 1H)

Example 130

Preparation of Derivative 130 According to the Present Invention

Derivative 130 having the following formula was prepared as follows.

[Formula of Derivative 130]

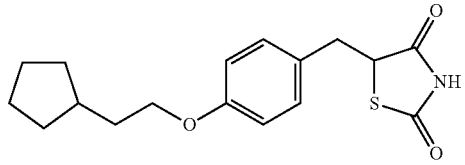

Derivative 130 having the above formula, 5-(4-(2-cyclopentylethoxy)benzyl)thiazolidine-2,4-dione, was obtained in accordance with the same method as described in Example 120, except that CoCl$_2$.6H$_2$O (4.77 mg, 0.016 mmol) and dimethylglyoxime (74.29 mg, 0.64 mmol) were used, and NaBH$_4$ (407.5 mg, 10.88 mmol) was added to obtain the mixture, to which 5-(4-(2-cyclopentylethoxy)benzylidene)thiazolidine-2,4-dione (1 g, 3.2 mmol) in 15 ml of THF-DMF (2:1) was added over 20 minutes (0.82 g, yield: 81.6%).

$^1$H NMR (300 MHz, CDCl3) δ 7.926 (s, 1H), 7.148 (d, J=8.4 Hz, 2H), 6.86 (d, J=8.4 Hz, 2H), 4.529 (dd, J=3.6, 4.2 Hz, 1H), 3.98 (t, J=13.5 Hz, 2H), 3.485 (dd, J=3.9, 3.9 Hz, 1H), 3.143 (dd, J=9.6, 9.3 Hz, 1H), 1.810-1.845 (m, 1H), 1.764-1.787 (m, 4H), 1.510-1.623 (m, 4H), 1.125-1.192 (m, 2H)

Experimental Example 1

Analysis of 15-PGDH Inhibitory Activity of the Derivatives According to the Present Invention <1-1> Expression and Purification of 15-PGDH In order to identify 15-PGDH inhibitory activities of the derivatives prepared in Example 1 to 130, 15-PGDH was purified first as follows:

A 15-PGDH cDNA plasmid containing BamHI and EcoRI sites of the pGES-2T expression vector was used to transform Escherichia coli BL-21 lysS in accordance with the ordinarily used in the art. The transformed cells were grown in 500 mL LB medium containing 50 μg/mL ampicillin at 37° C. while being stirred at 220 rpm until the OD$_{600}$ reached 0.6. Isopropyl β-D-thiogalactoside (1 mM) was added and the cells were allowed to grow for 12 hours at 25° C. Then, the pellets were harvested by centrifugation at 4000×g for 30 minutes at 4° C. The cell pallets were resuspended in 20 mL cell lysis buffer (1×PBS buffer (pH 7.4) containing 1 mM EDTA and 0.1 mM DTT) and sonicated (14×10 s at 4° C.). The disrupted cells were centrifuged at 4000×g for 20 minutes at 4° C. The supernatant was loaded slowly on a glutathione-sepharose 4B column, which was equilibrated at 4° C. with a cell lysis buffer (1×PBS buffer (pH 7.4) containing 1 mM EDTA and 0.1 mM DTT). The column was washed with the lysis buffer until $OD_{280}$ reached below 0.005. Then, 15-PGDH was eluted from the glutathione-sepharose 4B column at room temperature for 5 minutes by using the elution buffer (50 mM Tris-HCl (pH 8.0) containing 10 mM reduced glutathione, 1 mM EDTA and 0.1 mM DTT). The concentration and the purity of the purified enzyme were determined by SDS-PAGE.

<1-2> Assay for the Activities of 15-PGDH Inhibitors

In order to confirm whether the derivatives according to the present invention produce inhibitory activities against 15-PGDH, assay for inhibitory activities of the derivatives according to the present invention synthesized in Examples 1 to 130 against 15-PGDH purified in Experimental Example 1 was performed by measuring the formation of NADH at 340 nm with a fluorescence spectrophotometer. Specifically, 2 ml (in total) of the solution containing 50 mM Tris-HCl (pH 7.5), 0.1 mM DTT, 0.25 mM NAD+, 10 µg of purified 15-PGDH enzyme, 21 µM $PGE_2$ and various concentrations (0.0001 µM to 64 µM) of the derivatives according to the present invention was added to each cell. The absorbance of the reaction mixture was recorded at 340 nm so that the activities of the derivatives according to the present invention as 15-PGDH inhibitors were determined from a standard curve prepared from the absorbance of various concentrations of NADH at 340 nm. The results of determining the 15-PGDH inhibitory activities of the derivatives of the present invention are presented in Table 1 below, in which $IC_{50}$ means the concentration of the derivative for inhibiting 50% of the 15-PGDH activity.

As shown in Table 1 below, it was found that all of the derivatives according to the present invention produce 15-PGDH inhibitory activities. Especially, the derivatives having halogen as $R_1$ of benzylidene, which is connected to 5-position of thiazoline ring, were found to exhibit remarkably superior 15-PGDH inhibitory activities.

TABLE 1

| No | Formula | $IC_{50}$ (µM) | M. W. |
|---|---|---|---|
| 1 | | 0.9614 | 307.37 |
| 2 | | 0.5148 | 334.40 |
| 3 | | 0.0959 | 331.41 |
| 4 | | 0.1485 | 331.41 |
| 5 | | 1.3734 | 382.46 |
| 6 | | 0.5922 | 326.38 |

TABLE 1-continued
| No | Formula | IC$_{50}$ (μM) | M. W. |
|---|---|---|---|
| 7 | 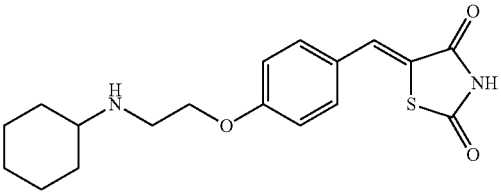 | 2.6149 | 346.45 |
| 8 | 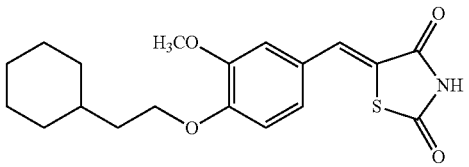 | 0.0230 | 361.46 |
| 9 | 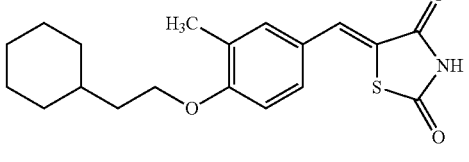 | 0.0550 | 345.46 |
| 10 |  | 0.0945 | 391.49 |
| 11 | 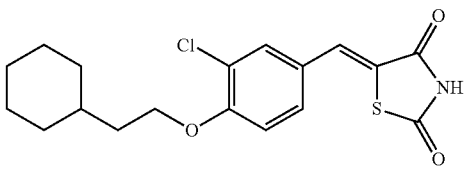 | 0.0072 | 365.88 |
| 12 | 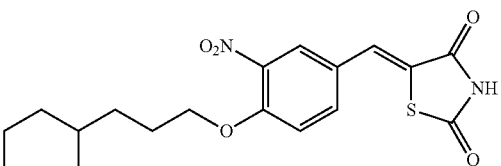 | 0.3267 | 390.46 |
| 13 | 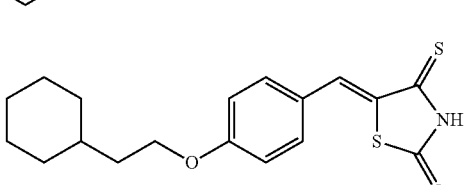 | 0.6894 | 347.50 |
| 14 | 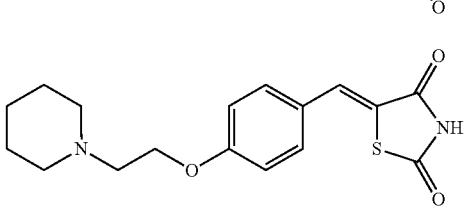 | 1.4251 | 332.42 |

TABLE 1-continued

| No | Formula | IC$_{50}$ (μM) | M. W. |
|---|---|---|---|
| 15 | | 0.0066 | 410.33 |
| 16 | | 0.0719 | 399.44 |
| 17 | | 0.3079 | 416.91 |
| 18 | | 0.0196 | 365.88 |
| 19 | | 1.1702 | 346.43 |
| 20 | | 0.0508 | 349.43 |
| 21 | | 3.0415 | 396.49 |
| 22 | | 0.2508 | 317.39 |

TABLE 1-continued

| No | Formula | IC$_{50}$ (μM) | M. W. |
|----|---------|----------------|-------|
| 23 | | 0.3917 | 317.39 |
| 24 | | 0.1146 | 317.41 |
| 25 | | 1.8762 | 301.32 |
| 26 | | 3.6402 | 312.35 |
| 27 | | 0.2549 | 325.39 |
| 28 | | 0.7279 | 341.39 |
| 29 | | 0.3101 | 355.37 |
| 30 | | 0.0489 | 337.83 |

TABLE 1-continued
| No | Formula | IC$_{50}$ (μM) | M. W. |
|---|---|---|---|
| 31 | 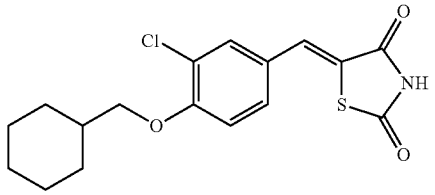 | 0.0269 | 351.85 |
| 32 | 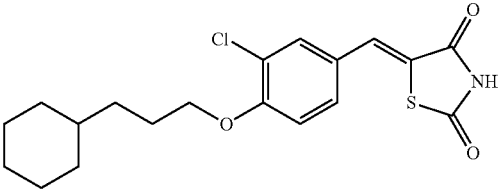 | 0.0103 | 379.91 |
| 33 | 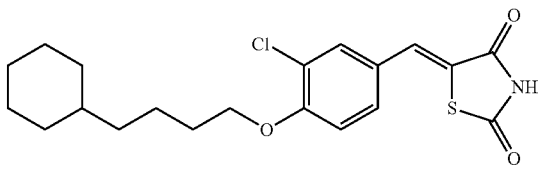 | 0.0263 | 393.94 |
| 34 | 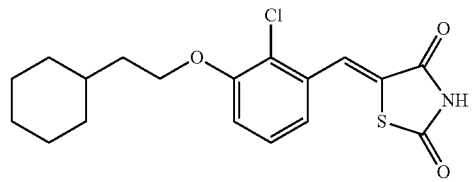 | 0.0179 | 365.88 |
| 35 | 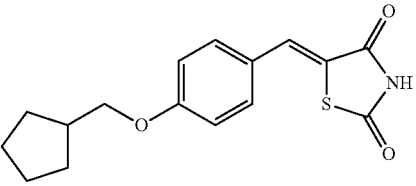 | 0.0425 | 303.38 |
| 36 | 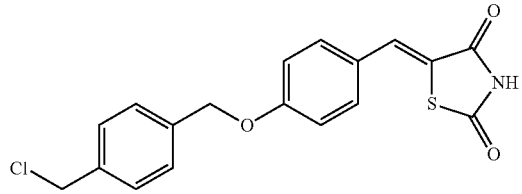 | 0.1245 | 359.83 |
| 37 | 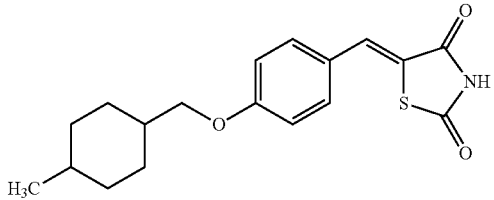 | 0.0664 | 331.44 |

TABLE 1-continued
| No | Formula | IC$_{50}$ (μM) | M. W. |
|---|---|---|---|
| 38 | 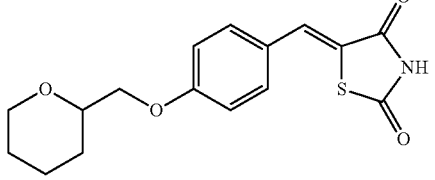 | 0.7504 | 319.38 |
| 39 | 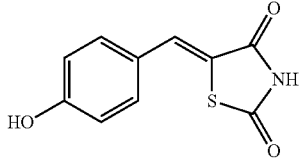 | 10.0581 | 221.24 |
| 40 | 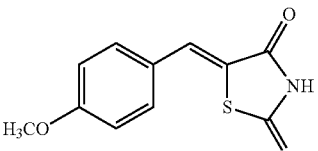 | 5.6669 | 235.26 |
| 41 | 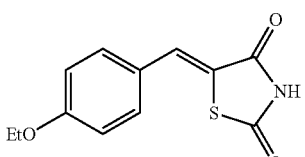 | 5.8204 | 249.29 |
| 42 | 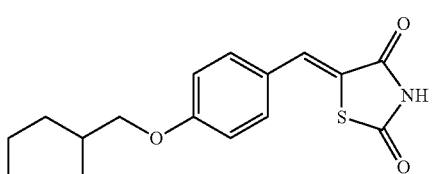 | 0.2172 | 317.41 |
| 43 | 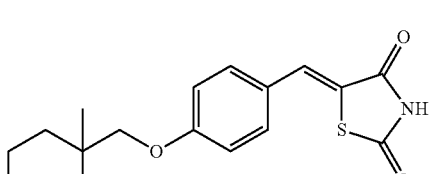 | 0.5466 | 331.44 |
| 44 | 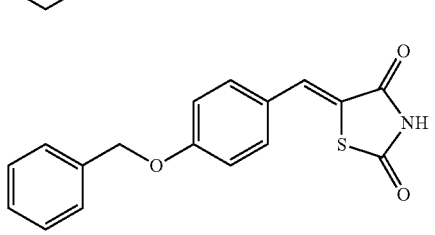 | 1.0439 | 311.36 |
| 45 | 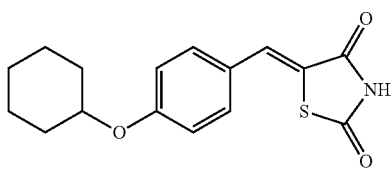 | 0.8216 | 303.38 |

TABLE 1-continued
| No | Formula | IC$_{50}$ (μM) | M. W. |
|---|---|---|---|
| 46 | 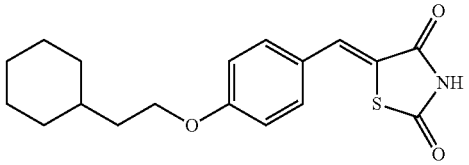 | 0.0509 | 331.44 |
| 47 | 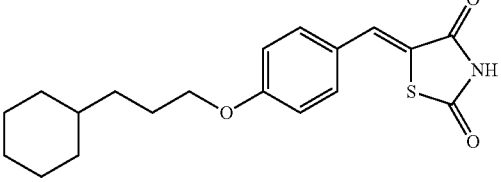 | 0.0622 | 345.46 |
| 48 | 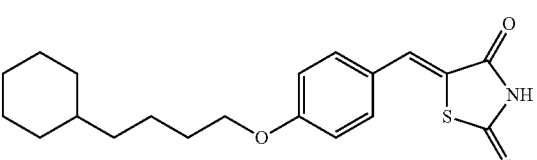 | 6.0146 | 359.49 |
| 49 | 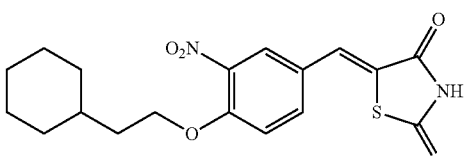 | 0.0595 | 376.43 |
| 50 | 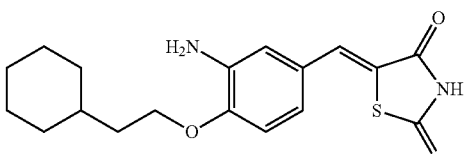 | 0.2855 | 346.45 |
| 51 | 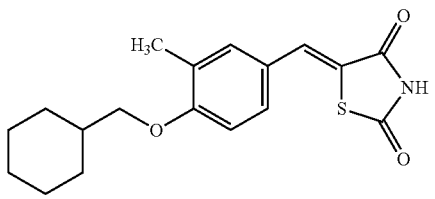 | 0.0498 | 331.44 |
| 52 | 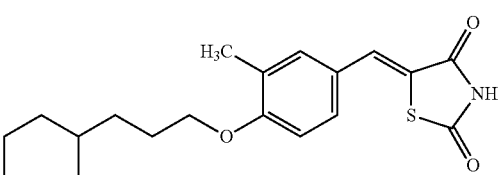 | 0.1043 | 359.49 |
| 53 | 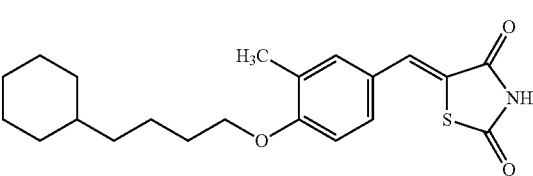 | 0.3993 | 373.52 |

TABLE 1-continued

| No | Formula | IC$_{50}$ (μM) | M. W. |
|---|---|---|---|
| 54 | | >20 | 297.33 |
| 55 | | 0.1170 | 325.39 |
| 56 | | 0.186 | 339.42 |
| 57 | | 0.225 | 353.44 |
| 58 | | 0.5260 | 375.49 |
| 59 | | 0.2589 | 375.48 |
| 60 | | 3.5622 | 361.46 |
| 61 | | 0.2187 | 347.43 |

TABLE 1-continued

| No | Formula | IC$_{50}$ (μM) | M. W. |
|----|---------|----------------|-------|
| 62 | | 0.1724 | 369.39 |
| 63 | | 0.0576 | 351.85 |
| 64 | | 0.059 | 379.90 |
| 65 | | 0.0314 | 399.48 |
| 66 | | 0.0204 | 375.44 |
| 67 | | 1.157 | 361.46 |
| 68 | | 0.0475 | 345.80 |

TABLE 1-continued
| No | Formula | IC$_{50}$ (μM) | M. W. |
|----|---------|----------------|-------|
| 69 | 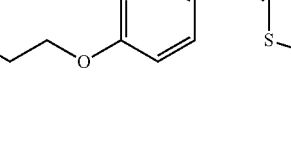 | 0.0198 | 359.83 |
| 70 | 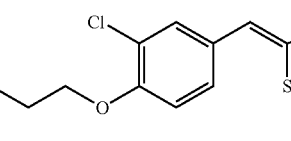 | 0.0381 | 373.85 |
| 71 | 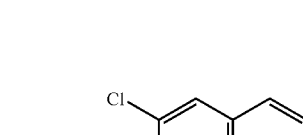 | 0.0475 | 387.89 |
| 72 | 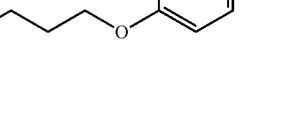 | 0.257 | 345.80 |
| 73 | 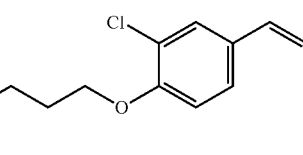 | 0.1222 | 359.83 |
| 74 | 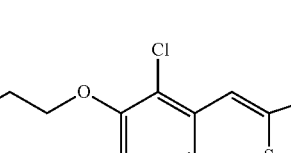 | 0.0543 | 387.89 |
| 75 | 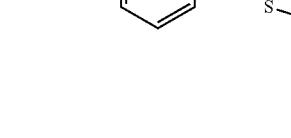 | 0.0449 | 373.85 |

TABLE 1-continued
| No | Formula | IC$_{50}$ (μM) | M. W. |
|---|---|---|---|
| 76 | 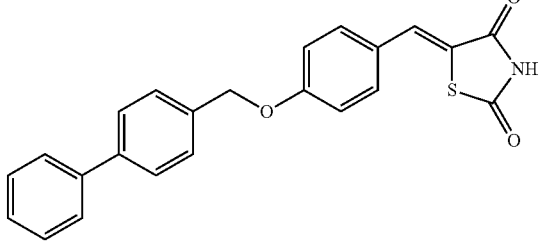 | 0.8142 | 387.45 |
| 77 | 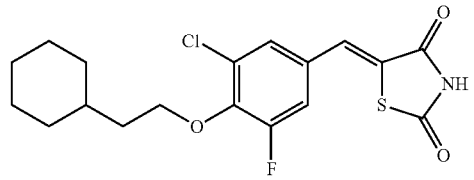 | 0.1772 | 383.87 |
| 78 | 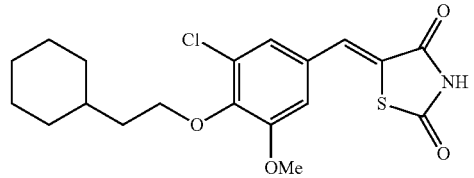 | 0.0506 | 395.91 |
| 79 | 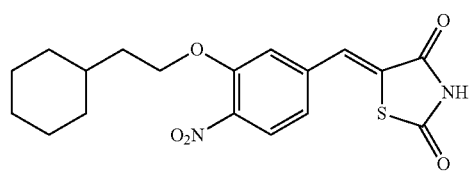 | 2.82 | 376.43 |
| 80 | 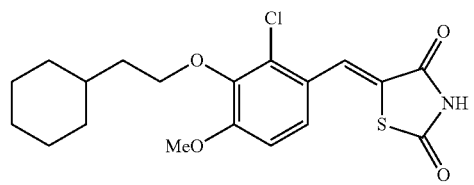 | 0.1098 | 395.91 |
| 81 | 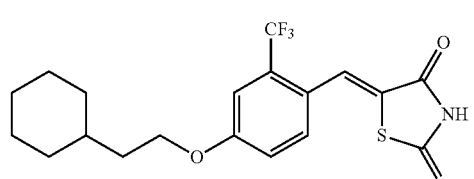 | 0.1365 | 399.48 |
| 82 | 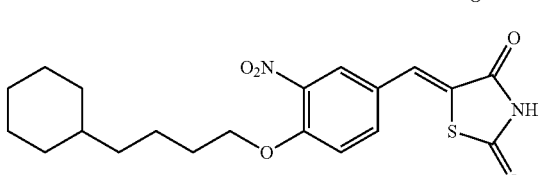 | 1.082 | 404.49 |
| 83 | 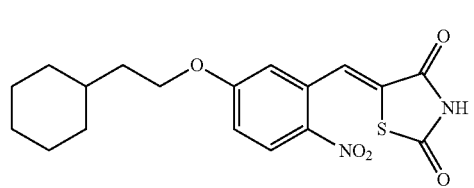 | 6.2762 | 376.43 |

TABLE 1-continued
| No | Formula | IC$_{50}$ (μM) | M. W. |
|---|---|---|---|
| 84 | 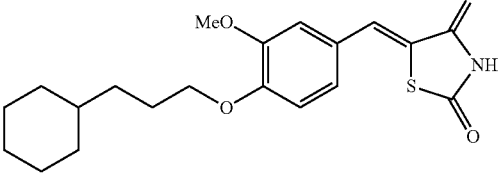 | 0.0221 | 375.49 |
| 85 | 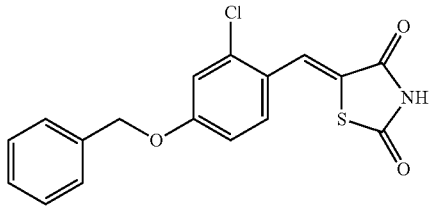 | 0.487 | 345.81 |
| 86 | 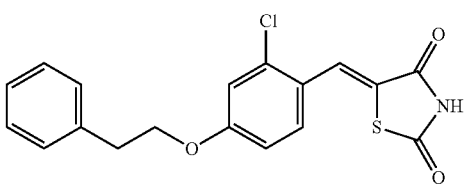 | 0.178 | 359.83 |
| 87 | 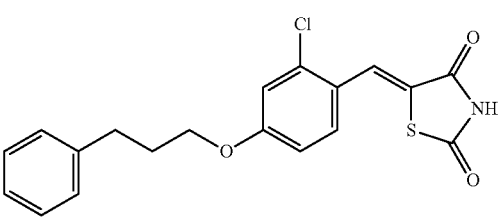 | 0.052 | 373.86 |
| 88 | 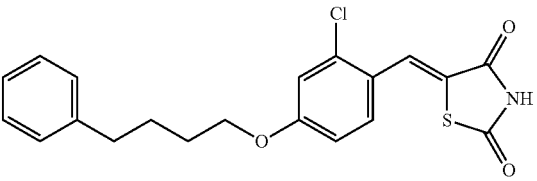 | 0.0810 | 387.89 |
| 89 | 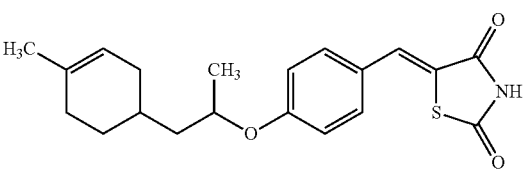 | 0.0284 | 365.88 |
| 90 | 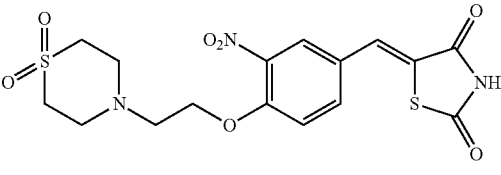 | 2.449 | 427.46 |
| 91 | 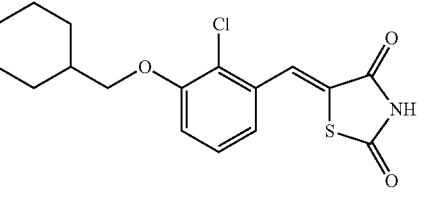 | 0.135 | 357.48 |

TABLE 1-continued

| No | Formula | IC$_{50}$ (μM) | M.W. |
|---|---|---|---|
| 92 | | 0.1728 | 341.81 |
| 93 | | 10.3012 | 360.81 |
| 94 | | 2.7375 | 341.81 |
| 95 | | 0.233 | 337.83 |
| 96 | | 2.449 | 351.85 |
| 97 | | 0.284 | 379.9 |
| 98 | | 1.645 | 393.93 |

TABLE 1-continued

| No | Formula | IC$_{50}$ (μM) | M. W. |
|---|---|---|---|
| 99 | | 0.2118 | 337.83 |
| 100 | | 0.0945 | 393.94 |
| 101 | | 0.0841 | 365.86 |
| 102 | | 0.6817 | 361.44 |
| 103 | | 1.6712 | 361.44 |
| 104 | | 8.9147 | 360.82 |
| 105 | | 1.0936 | 380.87 |
| 106 | | 5.1648 | 380.87 |

TABLE 1-continued
| No | Formula | IC$_{50}$ (μM) | M. W. |
|---|---|---|---|
| 107 | 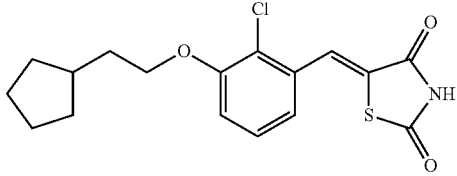 | 0.1539 | 351.85 |
| 108 | 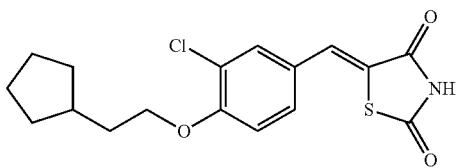 | 0.0993 | 351.85 |
| 109 | 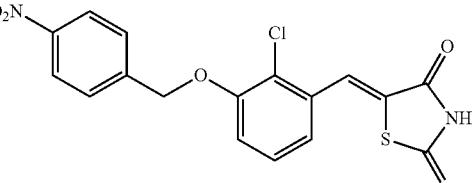 | 11.70 | 390.8 |
| 110 | 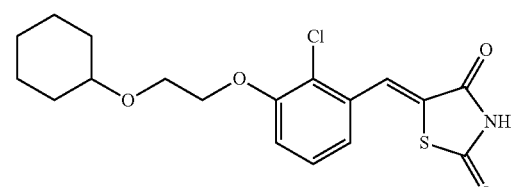 | 0.233 | 381.83 |
| 111 | 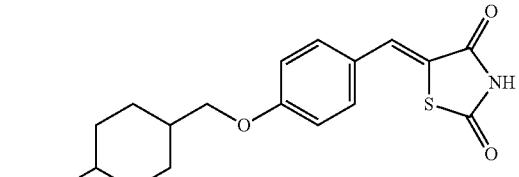 | 9.3267 | 361.42 |
| 112 | 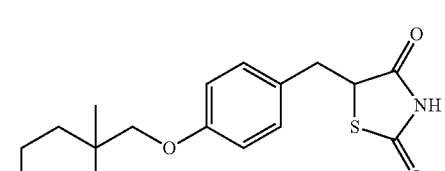 | 1.7391 | 333.45 |
| 113 | 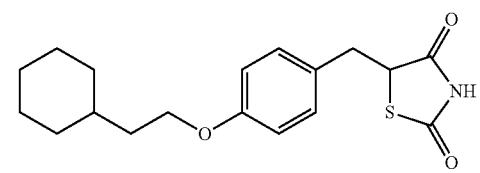 | 0.9770 | 333.45 |
| 114 | 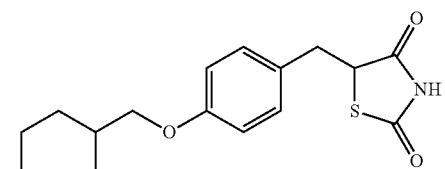 | 4.0622 | 319.43 |

TABLE 1-continued
| No | Formula | IC$_{50}$ (μM) | M. W. |
|----|---------|----------------|-------|
| 115 | 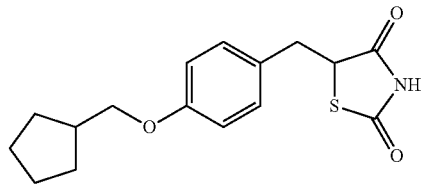 | 0.8539 | 305.39 |
| 116 | 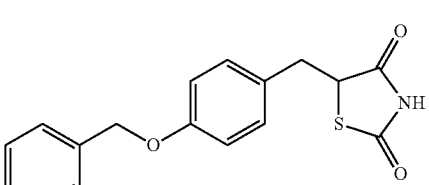 | 5.2516 | 313.37 |
| 117 | 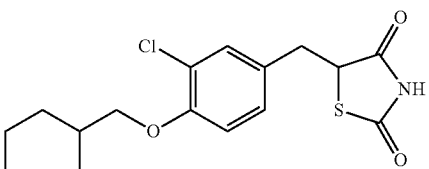 | 0.5263 | 353.86 |
| 118 | 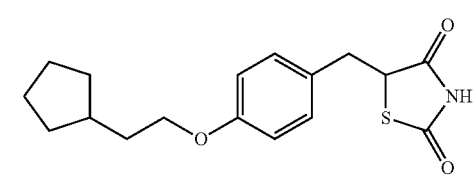 [SMILES: O=C1NC(=O)C(Cc2ccc(OCCC3CCCC3)cc2)S1] | 2.2097 | 353.90 |
| 119 | 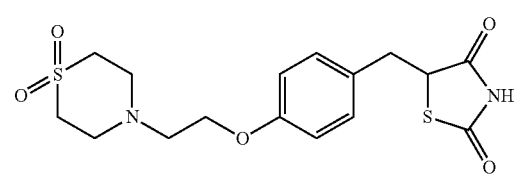 [SMILES: O=C1NC(=O)C(Cc2ccc(OCCN3CCS(=O)(=O)CC3)cc2)S1] | 5.2136 | 384.47 |
| 120 | 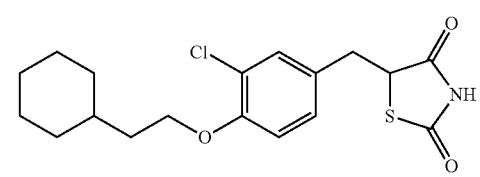 [SMILES: O=C1NC(=O)C(Cc2ccc(OCCC3CCCCC3)c(Cl)c2)S1] | 0.1729 | 367.90 |
| 121 | 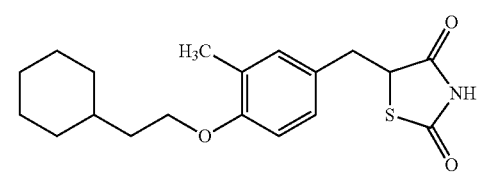 [SMILES: Cc1cc(CC2SC(=O)NC2=O)ccc1OCCC1CCCCC1] | 0.3974 | 347.47 |
| 122 | 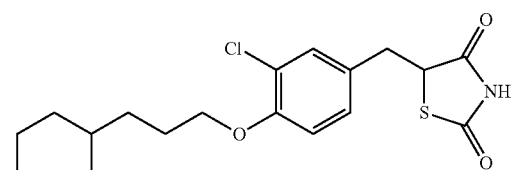 | 0.1428 | 381.92 |

TABLE 1-continued
| No | Formula | IC$_{50}$ (μM) | M. W. |
|----|---------|----------------|-------|
| 123 | 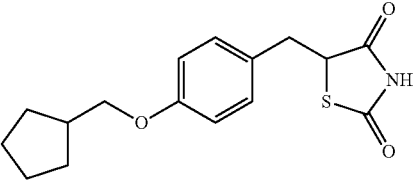 [SMILES: O=C1NC(=O)C(Cc2ccc(OCC3CCCC3)cc2)S1] | 0.2048 | 305.39 |
| 124 | 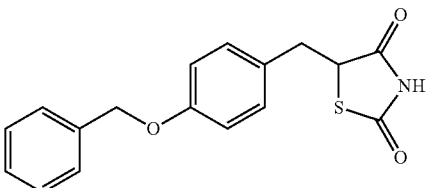 | 1.2571 | 313.37 |
| 125 | 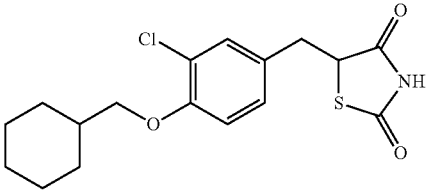 [SMILES: O=C1NC(=O)C(Cc2ccc(OCC3CCCCC3)c(Cl)c2)S1] | 0.1251 | 353.86 |
| 126 | 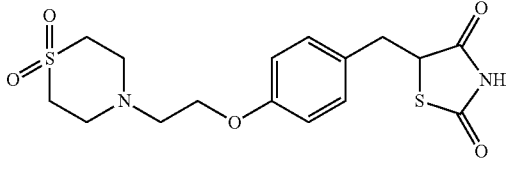 [SMILES: O=C1NC(=O)C(Cc2ccc(OCCN3CCS(=O)(=O)CC3)cc2)S1] | 1.3945 | 384.47 |
| 127 | 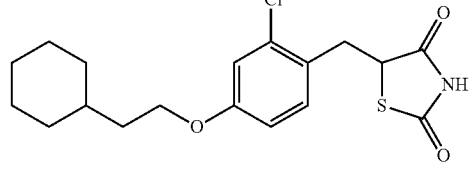 | 0.1578 | 367.89 |
| 128 | 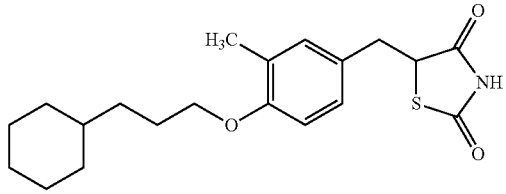 [SMILES: Cc1cc(CC2SC(=O)NC2=O)ccc1OCCCC1CCCCC1] | 0.6674 | 361.50 |
| 129 | 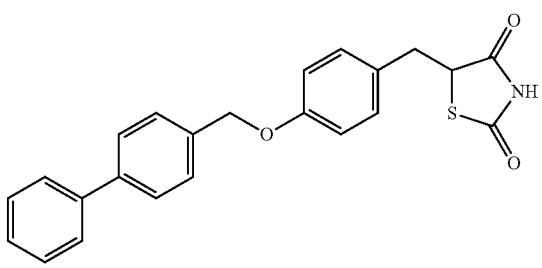 [SMILES: O=C1NC(=O)C(Cc2ccc(OCc3ccc(-c4ccccc4)cc3)cc2)S1] | 1.0798 | 389.48 |

TABLE 1-continued

| No | Formula | IC$_{50}$ (μM) | M. W. |
|---|---|---|---|
| 130 | 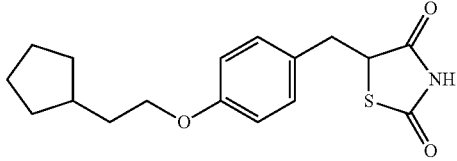 [SMILES: O=C1NC(=O)C(Cc2ccc(OCCC3CCCC3)cc2)S1] | 0.7769 | 319.43 |

While the invention has been shown and described with respect to the preferred embodiments, it will be understood by those skilled in the art that various changes and modifications may be made without departing from the spirit and scope of the invention as defined in the following claims.

What is claimed is:

1. A thiazolidinedione derivative having a formula selected from the group consisting of

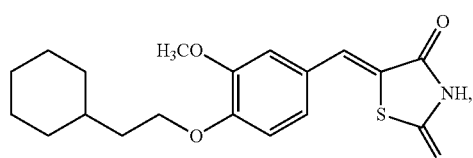

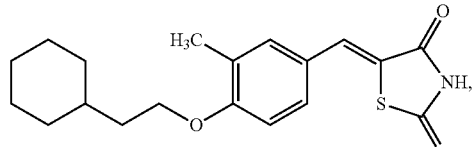

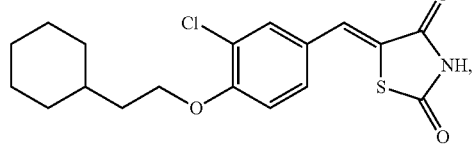

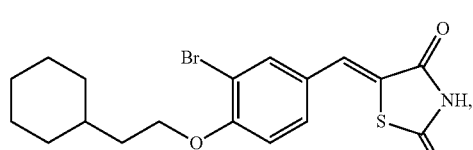

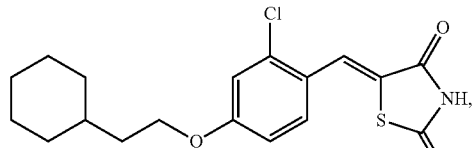

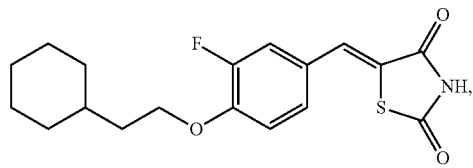

-continued

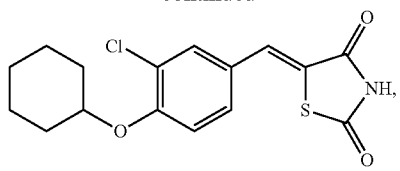

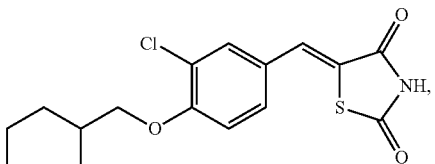

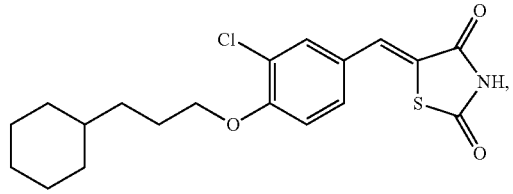

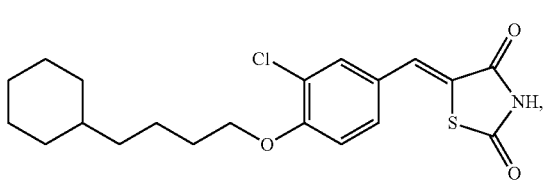

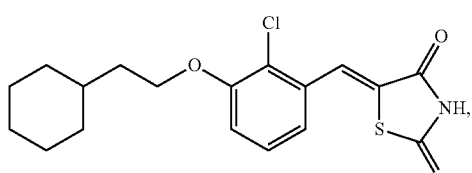

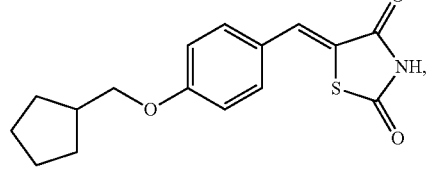

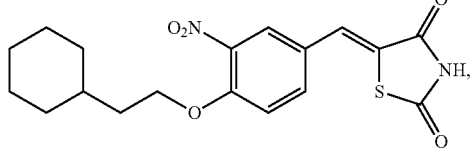

-continued

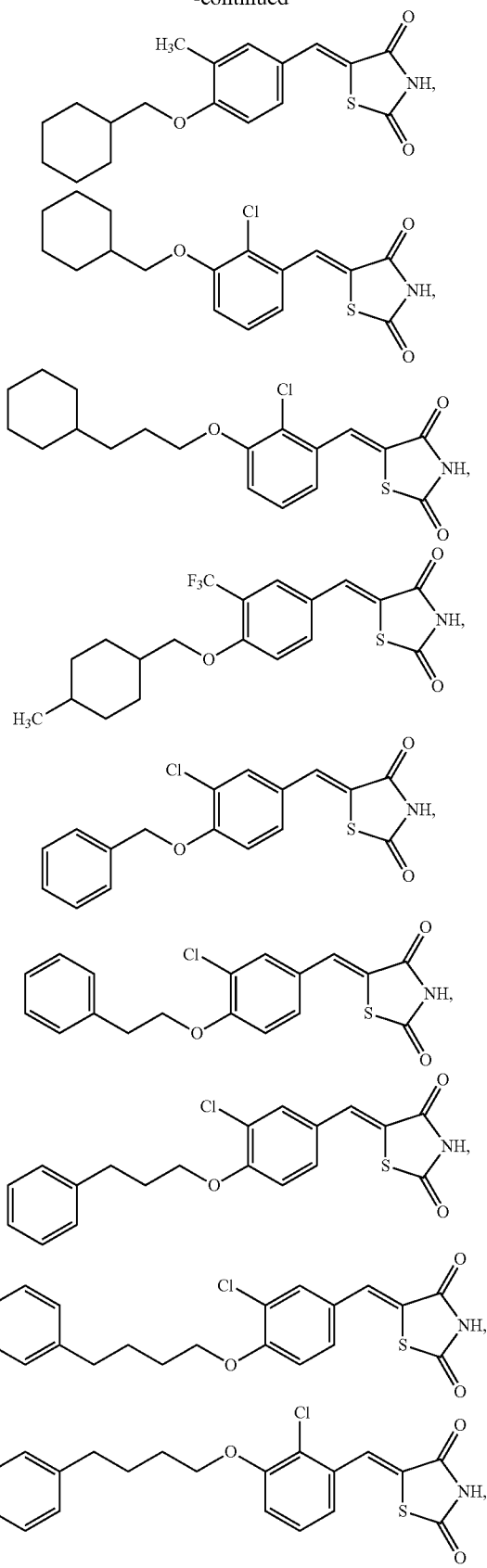

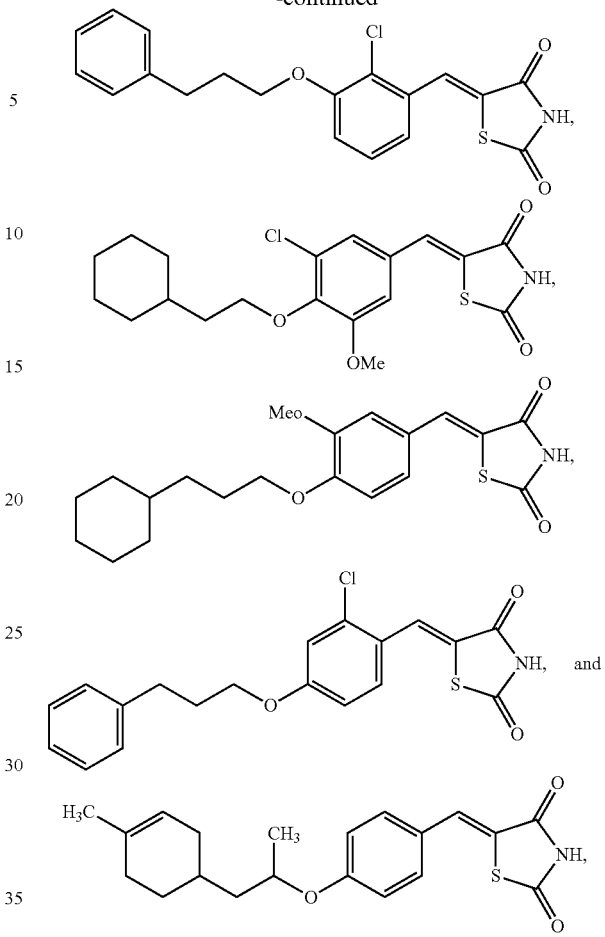

or a pharmaceutically acceptable salt thereof.

2. A method for treating alopecia in a subject comprising administering to the subject a composition comprising the derivative according to claim 1, or a pharmaceutically acceptable salt thereof as an active ingredient.

3. A method for treating a cardiovascular disease in a subject comprising administering to the subject a composition comprising the derivative according to claim 1, or a pharmaceutically acceptable salt thereof as an active ingredient.

4. A method for treating a gastrointestinal disease in a subject comprising administering to the subject a composition comprising the derivative according to claim 1, or a pharmaceutically acceptable salt thereof as an active ingredient.

5. A method for treating a renal disease in a subject comprising administering to the subject a composition comprising the derivative according to claim 1, or a pharmaceutically acceptable salt thereof as an active ingredient.

6. A method for promoting osteogenesis in a subject comprising administering to the subject a composition comprising the derivative according to claim 1, or a pharmaceutically acceptable salt thereof as an active ingredient.

7. A method for wound healing in a subject comprising administering to the subject a composition comprising the derivative according to claim 1, or a pharmaceutically acceptable salt thereof as an active ingredient.

* * * * *